United States Patent
Tallarida et al.

(10) Patent No.: US 7,604,641 B2
(45) Date of Patent: *Oct. 20, 2009

(54) SYSTEM AND METHOD FOR JOINT RESURFACE REPAIR

(75) Inventors: Steven J. Tallarida, Mansfield, MA (US); Steven W. Ek, Bolton, MA (US)

(73) Assignee: Arthrosurface Incorporated, Franklin, MA (US)

( * ) Notice: Subject to any disclaimer, the term of this patent is extended or adjusted under 35 U.S.C. 154(b) by 65 days.

This patent is subject to a terminal disclaimer.

(21) Appl. No.: 11/379,151

(22) Filed: Apr. 18, 2006

(65) Prior Publication Data

US 2006/0190002 A1    Aug. 24, 2006

Related U.S. Application Data

(60) Continuation of application No. 10/360,228, filed on Feb. 6, 2003, now Pat. No. 7,029,479, which is a division of application No. 09/846,657, filed on May 1, 2001, now Pat. No. 6,520,964.

(60) Provisional application No. 60/201,049, filed on May 1, 2000.

(51) Int. Cl.
*A61B 17/58* (2006.01)
*A61B 17/60* (2006.01)

(52) U.S. Cl. .................................. 606/102; 606/79

(58) Field of Classification Search ............... 623/20.3, 623/20.34, 20.36, 20.14, 20.15, 20.24, 20.28, 623/19.14, 23.46, 23.47, 20.18; 606/102, 606/88, 85, 96, 71, 289, 298, 75, 104, 215, 606/79, 86 A See application file for complete search history.

(56) References Cited

U.S. PATENT DOCUMENTS

| 992,819 | A | 5/1911 | Springer |
| 1,451,610 | A | 4/1923 | Gestas |
| 2,267,925 | A | 12/1941 | Johnston |
| 3,840,905 | A | 10/1974 | Deane |
| 4,016,651 | A | 4/1977 | Kawahara et al. |

(Continued)

FOREIGN PATENT DOCUMENTS

AU    2001262308    12/2001

(Continued)

OTHER PUBLICATIONS

Habermeyer, Peter, Atos News, Oct. 2005, "The Artificial Limb "Eclipse"—A new draft without shank in the implantation of artificial shoulder limbs", cover page w/pp. 40-41, with English translation dated Jan. 13, 2006 (2 pgs).

(Continued)

*Primary Examiner*—Pedro Philogene
(74) *Attorney, Agent, or Firm*—Grossman Tucker Perreault & Pfleger PLLC

(57) ABSTRACT

A system for positioning an element relative to an articular surface. An embodiment of the system may include a first element having a positional reference relative to an articular surface. The system may further include a second element capable of indicating the positional reference of the first element relative to said articular surface. Of course, many alternatives, variations, and modifications are possible without departing from this embodiment.

31 Claims, 42 Drawing Sheets

U.S. PATENT DOCUMENTS

| | | | |
|---|---|---|---|
| 4,034,418 A | 7/1977 | Jackson et al. | |
| 4,044,464 A | 8/1977 | Schiess et al. | |
| 4,158,894 A | 6/1979 | Worrell | |
| 4,344,192 A | 8/1982 | Imbert | |
| 4,433,687 A | 2/1984 | Burke et al. | |
| 4,462,120 A | 7/1984 | Rambert et al. | |
| 4,474,177 A | 10/1984 | Whiteside | |
| 4,484,570 A | 11/1984 | Sutter et al. | |
| 4,531,517 A | 7/1985 | Forte et al. | |
| 4,535,768 A | 8/1985 | Hourahane et al. | |
| 4,634,720 A | 1/1987 | Dorman et al. | |
| 4,655,752 A | 4/1987 | Honkanen et al. | |
| 4,661,536 A | 4/1987 | Dorman et al. | |
| 4,662,371 A | 5/1987 | Whipple et al. | |
| 4,664,669 A | 5/1987 | Ohyabu et al. | |
| 4,673,407 A | 6/1987 | Martin | |
| 4,693,986 A | 9/1987 | Vit et al. | |
| 4,712,545 A | 12/1987 | Honkanen | |
| 4,719,908 A | 1/1988 | Averill et al. | |
| 4,729,761 A | 3/1988 | White | |
| 4,823,780 A | 4/1989 | Odensten et al. | |
| 4,842,604 A | 6/1989 | Dorman et al. | |
| 4,896,663 A | 1/1990 | Vandewalls | |
| 4,911,153 A | 3/1990 | Border | |
| 4,927,421 A | 5/1990 | Goble et al. | |
| 4,938,778 A | 7/1990 | Ohyabu et al. | |
| 4,940,467 A | 7/1990 | Tronzo | |
| 4,976,037 A | 12/1990 | Hines | |
| 4,979,957 A | 12/1990 | Hodorek | |
| 4,989,110 A | 1/1991 | Zevin et al. | |
| 4,990,163 A | 2/1991 | Ducheyne et al. | |
| 4,997,434 A | 3/1991 | Seedhom et al. | |
| 4,998,938 A | 3/1991 | Ghajar et al. | |
| 5,007,930 A | 4/1991 | Dorman et al. | |
| 5,019,104 A | 5/1991 | Whiteside et al. | |
| 5,100,405 A | 3/1992 | McLaren | |
| 5,127,920 A | 7/1992 | MacArthur | |
| 5,192,291 A | 3/1993 | Pannek, Jr. | |
| 5,201,881 A | 4/1993 | Evans | |
| 5,211,647 A | 5/1993 | Schmieding | |
| 5,224,945 A | 7/1993 | Pannek, Jr. | |
| 5,255,838 A | 10/1993 | Gladdish, Jr. et al. | |
| 5,263,498 A | 11/1993 | Caspari et al. | |
| 5,263,987 A | 11/1993 | Shah | |
| 5,282,863 A | 2/1994 | Burton | |
| 5,290,313 A * | 3/1994 | Heldreth | 623/20.15 |
| 5,312,411 A | 5/1994 | Steele | |
| 5,314,478 A | 5/1994 | Oka et al. | |
| 5,314,482 A | 5/1994 | Goodfellow et al. | |
| 5,336,224 A | 8/1994 | Selman | |
| 5,354,300 A | 10/1994 | Goble et al. | |
| 5,358,525 A | 10/1994 | Fox et al. | |
| 5,360,446 A | 11/1994 | Kennedy | |
| 5,374,270 A * | 12/1994 | McGuire et al. | 606/80 |
| 5,383,937 A | 1/1995 | Mikhail | |
| 5,387,218 A | 2/1995 | Meswania | |
| 5,395,401 A | 3/1995 | Bahler | |
| 5,409,494 A | 4/1995 | Morgan | |
| 5,413,608 A | 5/1995 | Keller | |
| 5,423,822 A | 6/1995 | Hershberger | |
| 5,458,643 A | 10/1995 | Oka et al. | |
| 5,480,443 A | 1/1996 | Elias | |
| 5,486,178 A | 1/1996 | Hodge | |
| 5,509,918 A | 4/1996 | Romano | |
| 5,520,695 A | 5/1996 | Luckman | |
| 5,522,900 A | 6/1996 | Hollister | |
| 5,534,031 A | 7/1996 | Matsuzaki et al. | |
| 5,540,696 A | 7/1996 | Booth, Jr. et al. | |
| 5,580,353 A * | 12/1996 | Mendes et al. | 623/20.18 |
| 5,593,450 A | 1/1997 | Scott et al. | |
| 5,595,193 A | 1/1997 | Walus et al. | |
| 5,601,550 A | 2/1997 | Esser | |
| 5,616,146 A | 4/1997 | Murray | |
| 5,620,055 A | 4/1997 | Javerlhac | |
| 5,624,463 A | 4/1997 | Stone et al. | |
| 5,632,745 A * | 5/1997 | Schwartz | 606/75 |
| 5,645,598 A | 7/1997 | Brosnahan, III | |
| 5,681,311 A | 10/1997 | Foley et al. | |
| 5,682,886 A | 11/1997 | Delp et al. | |
| 5,683,400 A | 11/1997 | McGuire | |
| 5,683,465 A | 11/1997 | Shinn et al. | |
| 5,683,466 A * | 11/1997 | Vitale | 623/21.15 |
| 5,700,264 A | 12/1997 | Zucherman et al. | |
| 5,700,265 A | 12/1997 | Romano | |
| 5,702,401 A | 12/1997 | Shaffer | |
| 5,702,465 A | 12/1997 | Burkinshaw | |
| 5,702,467 A | 12/1997 | Gabriel et al. | |
| 5,741,266 A | 4/1998 | Moran et al. | |
| 5,769,855 A | 6/1998 | Bertin et al. | |
| 5,771,310 A | 6/1998 | Vannah | |
| 5,772,866 A | 6/1998 | Hart et al. | |
| 5,776,137 A | 7/1998 | Katz | |
| 5,782,835 A | 7/1998 | Hart et al. | |
| 5,810,851 A | 9/1998 | Yoon | |
| 5,817,095 A | 10/1998 | Smith | |
| 5,824,105 A | 10/1998 | Ries et al. | |
| 5,882,350 A | 3/1999 | Ralph et al. | |
| 5,885,297 A | 3/1999 | Matsen, III | |
| 5,885,298 A | 3/1999 | Herrington et al. | |
| 5,888,210 A | 3/1999 | Draenert | |
| 5,893,889 A | 4/1999 | Harrington | |
| 5,895,390 A | 4/1999 | Moran et al. | |
| 5,911,126 A | 6/1999 | Massen | |
| 5,918,604 A | 7/1999 | Whelan | |
| 5,919,196 A | 7/1999 | Bobic et al. | |
| 5,928,239 A | 7/1999 | Mirza | |
| 5,928,286 A | 7/1999 | Ashby et al. | |
| 5,964,752 A | 10/1999 | Stone | |
| 5,964,768 A | 10/1999 | Huebner | |
| 5,964,808 A | 10/1999 | Blaha et al. | |
| 5,968,050 A | 10/1999 | Torrie | |
| 5,989,269 A | 11/1999 | Vibe-Hansen et al. | |
| 5,990,382 A | 11/1999 | Fox | |
| 5,997,543 A | 12/1999 | Truscott | |
| 6,004,323 A | 12/1999 | Park et al. | |
| 6,010,502 A | 1/2000 | Bagby | |
| 6,015,411 A | 1/2000 | Ohkoshi et al. | |
| 6,017,348 A | 1/2000 | Hart et al. | |
| 6,019,767 A | 2/2000 | Howell | |
| 6,045,564 A | 4/2000 | Walen | |
| 6,052,909 A | 4/2000 | Gardner | |
| 6,059,831 A | 5/2000 | Braslow | |
| 6,071,310 A | 6/2000 | Picha et al. | |
| 6,081,741 A | 6/2000 | Hollis | |
| 6,086,593 A | 7/2000 | Bonutti | |
| 6,102,948 A | 8/2000 | Brosnahan, III | |
| 6,120,542 A | 9/2000 | Camino et al. | |
| 6,132,433 A | 10/2000 | Whelan | |
| 6,146,385 A | 11/2000 | Torrie et al. | |
| 6,149,654 A | 11/2000 | Johnson | |
| 6,159,216 A | 12/2000 | Burkinshaw et al. | |
| 6,165,223 A * | 12/2000 | Metzger et al. | 623/20.27 |
| 6,168,626 B1 | 1/2001 | Hyon et al. | |
| 6,171,340 B1 | 1/2001 | McDowell | |
| 6,193,724 B1 | 2/2001 | Chan | |
| 6,206,885 B1 | 3/2001 | Ghahremani et al. | |
| 6,217,549 B1 | 4/2001 | Selmon et al. | |
| 6,217,619 B1 * | 4/2001 | Keller | 623/20.34 |
| 6,235,060 B1 | 5/2001 | Kubein-Meesenburg et al. | |
| 6,251,143 B1 | 6/2001 | Schwartz et al. | |
| 6,280,474 B1 | 8/2001 | Cassidy et al. | |
| 6,299,645 B1 | 10/2001 | Ogden | |
| 6,299,648 B1 | 10/2001 | Doubler et al. | |
| 6,306,142 B1 | 10/2001 | Johanson et al. | |

| | | | | | | |
|---|---|---|---|---|---|---|
| 6,315,798 | B1 | 11/2001 | Ashby et al. | 2003/0225457 A1 | 12/2003 | Justin et al. |
| 6,322,500 | B1 | 11/2001 | Sikora et al. | 2004/0015170 A1 | 1/2004 | Tallarida et al. |
| 6,328,752 | B1 | 12/2001 | Sjostrom et al. | 2004/0034359 A1 | 2/2004 | Schmieding et al. |
| 6,342,075 | B1 | 1/2002 | MacArthur | 2004/0034437 A1 | 2/2004 | Schmieding |
| 6,358,251 | B1 | 3/2002 | Mirza | 2004/0082906 A1 | 4/2004 | Tallarida et al. |
| 6,358,253 | B1 | 3/2002 | Torrie et al. | 2004/0106928 A1 | 6/2004 | Ek |
| 6,375,658 | B1 | 4/2002 | Hangody et al. | 2004/0133276 A1 | 7/2004 | Lang et al. |
| 6,383,188 | B2 | 5/2002 | Kuslich | 2004/0138754 A1 | 7/2004 | Lang et al. |
| 6,415,516 | B1 | 7/2002 | Tirado et al. | 2004/0138758 A1 | 7/2004 | Evans et al. |
| 6,443,954 | B1 | 9/2002 | Bramlet et al. | 2004/0148030 A1 | 7/2004 | Ek |
| 6,461,373 | B2 | 10/2002 | Wyman et al. | 2004/0153087 A1 | 8/2004 | Sanford et al. |
| 6,468,309 | B1 | 10/2002 | Lieberman | 2004/0193281 A1 | 9/2004 | Grimes |
| 6,478,178 | B2 | 11/2002 | Ralph et al. | 2004/0199166 A1 | 10/2004 | Schmieding et al. |
| 6,478,801 | B1 | 11/2002 | Ralph et al. | 2004/0230315 A1 | 11/2004 | Ek |
| 6,482,210 | B1 | 11/2002 | Skiba et al. | 2004/0260303 A1 | 12/2004 | Carrison |
| 6,494,914 | B2 | 12/2002 | Brown | 2005/0015153 A1 | 1/2005 | Gobel et al. |
| 6,520,964 | B2 | 2/2003 | Tallarida et al. | 2005/0043808 A1 | 2/2005 | Felt et al. |
| 6,527,754 | B1 | 3/2003 | Tallarida et al. | 2005/0065612 A1 | 3/2005 | Winslow |
| 6,530,956 | B1 | 3/2003 | Mansmann | 2005/0075642 A1 | 4/2005 | Felt |
| 6,537,274 | B1 | 3/2003 | Katz | 2005/0143731 A1 | 6/2005 | Justin et al. |
| 6,540,786 | B2 | 4/2003 | Chibrac et al. | 2005/0143745 A1 | 6/2005 | Hodorek et al. |
| 6,551,322 | B1 | 4/2003 | Lieberman | 2005/0143831 A1 | 6/2005 | Justin et al. |
| 6,575,982 | B1 | 6/2003 | Bonutti | 2005/0154398 A1 | 7/2005 | Miniaci et al. |
| 6,585,666 | B2 | 7/2003 | Suh et al. | 2005/0229323 A1 | 10/2005 | Mills et al. |
| 6,591,581 | B2 | 7/2003 | Schmieding | 2005/0287187 A1 | 12/2005 | Mansmann |
| 6,599,321 | B2 | 7/2003 | Hyde et al. | 2006/0004461 A1 | 1/2006 | Justin et al. |
| 6,607,561 | B2 | 8/2003 | Brannon | 2006/0020343 A1 | 1/2006 | Ek |
| 6,610,067 | B2 | 8/2003 | Tallarida | 2006/0052878 A1 | 3/2006 | Schmieding |
| 6,679,917 | B2 | 1/2004 | Ek | 2006/0058744 A1 | 3/2006 | Tallarida et al. |
| 6,746,451 | B2 | 6/2004 | Middleton et al. | 2006/0085006 A1 | 4/2006 | Ek |
| 6,770,078 | B2 | 8/2004 | Bonutti | 2006/0149370 A1 | 7/2006 | Schmieding et al. |
| 6,783,550 | B2 | 8/2004 | MacArthur | 2006/0195112 A1 | 8/2006 | Ek |
| 6,783,551 | B1 | 8/2004 | Metzger | 2006/0229726 A1 | 10/2006 | Ek |
| 6,802,864 | B2 | 10/2004 | Tornier | 2007/0005143 A1 | 1/2007 | Ek |
| 6,814,735 | B1 | 11/2004 | Zirngibl | 2007/0073394 A1 | 3/2007 | Seedhom et al. |
| 6,827,722 | B1 | 12/2004 | Schoenefeld | 2007/0093842 A1 | 4/2007 | Schmieding |
| 6,860,902 | B2 | 3/2005 | Reiley | 2007/0093890 A1 | 4/2007 | Eliasen et al. |
| 6,884,246 | B1 | 4/2005 | Sonnabend et al. | 2007/0118136 A1 | 5/2007 | Ek |
| 6,923,813 | B2 | 8/2005 | Phillips et al. | 2007/0123921 A1 | 5/2007 | Ek |
| 6,926,739 | B1 | 8/2005 | O'Connor | 2007/0179608 A1 | 8/2007 | Ek |
| 6,962,577 | B2 | 11/2005 | Tallarida et al. | 2007/0233128 A1 | 10/2007 | Schmieding et al. |
| 6,969,393 | B2 | 11/2005 | Pinczewski et al. | 2007/0250067 A1 | 10/2007 | Schmieding et al. |
| 6,989,016 | B2 | 1/2006 | Tallarida et al. | 2007/0255399 A1 | 11/2007 | Eliasen et al. |
| 7,029,479 | B2 | 4/2006 | Tallarida | 2007/0265700 A1 | 11/2007 | Eliasen et al. |
| 7,063,717 | B2 | 6/2006 | St. Pierre et al. | 2007/0288031 A1 | 12/2007 | Dreyfuss et al. |
| 7,115,131 | B2 | 10/2006 | Engh et al. | 2007/0299519 A1 | 12/2007 | Schmieding |
| 7,156,880 | B2 | 1/2007 | Evans et al. | 2008/0004659 A1 | 1/2008 | Burkhart et al. |
| 7,160,305 | B2 | 1/2007 | Schmieding | 2008/0015709 A1 | 1/2008 | Evans et al. |
| 7,163,541 | B2 | 1/2007 | Ek | 2008/0027430 A1 | 1/2008 | Montgomery et al. |
| 7,166,133 | B2 | 1/2007 | Evans et al. | 2008/0033443 A1 | 2/2008 | Sikora et al. |
| 7,204,839 | B2 | 4/2007 | Dreyfuss et al. | 2008/0086139 A1 | 4/2008 | Bourke et al. |
| 7,204,854 | B2 | 4/2007 | Guederian et al. | 2008/0172125 A1 | 7/2008 | Ek |
| 7,235,107 | B2 | 6/2007 | Evans et al. | 2008/0183290 A1 | 7/2008 | Baird et al. |
| 7,241,316 | B2 | 7/2007 | Evans et al. | 2008/0188935 A1 | 8/2008 | Saylor et al. |
| 7,264,634 | B2 | 9/2007 | Schmieding | 2008/0275512 A1 | 11/2008 | Albertirio et al. |
| 7,303,577 | B1 | 12/2007 | Dean | 2008/0306483 A1 | 12/2008 | Iannarone |
| 7,311,702 | B2 | 12/2007 | Tallarida et al. | | | |
| 2001/0012967 | A1 | 8/2001 | Mosseri | FOREIGN PATENT DOCUMENTS | | |
| 2001/0039455 | A1 | 11/2001 | Simon et al. | | | |
| 2001/0056266 | A1 | 12/2001 | Tallarida et al. | AU | 2003262428 | 8/2009 |
| 2002/0055783 | A1 | 5/2002 | Tallarida et al. | DE | 2933174 | 4/1980 |
| 2002/0106393 | A1 | 8/2002 | Bianchi et al. | DE | 3516743 | 11/1986 |
| 2002/0138150 | A1 | 9/2002 | Leclercq | EP | 0350780 | 7/1989 |
| 2002/0147498 | A1 | 10/2002 | Tallarida et al. | EP | 0350780 | 1/1990 |
| 2003/0028196 | A1 | 2/2003 | Bonutti | EP | 0485678 | 5/1992 |
| 2003/0060887 | A1 | 3/2003 | Ek | EP | 0505634 | 9/1992 |
| 2003/0105465 | A1 | 6/2003 | Schmieding et al. | EP | 0903125 | 3/1999 |
| 2003/0120276 | A1 | 6/2003 | Tallarida et al. | EP | 0903127 | 3/1999 |
| 2003/0120278 | A1 | 6/2003 | Morgan et al. | EP | 0661023 | 8/2001 |
| 2003/0171756 | A1 | 9/2003 | Fallin et al. | EP | 1426013 | 9/2004 |
| 2003/0181878 | A1 | 9/2003 | Tallarida et al. | EP | 1278460 | 4/2009 |
| 2003/0204195 | A1 | 10/2003 | Keane et al. | FR | 2242068 | 3/1975 |
| 2003/0225456 | A1 | 12/2003 | Ek | FR | 2642301 | 8/1990 |

| FR | 2718014 | 10/1995 |
| FR | 2739151 | 3/1997 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2001525210 | 12/2001 |
| JP | 2003534096 | 11/2003 |
| WO | 19881003781 | 6/1988 |
| WO | 8909578 | 10/1989 |
| WO | 9427507 | 12/1994 |
| WO | 1997022306 | 6/1997 |
| WO | WO99/20192 | 4/1999 |
| WO | 0105336 | 1/2001 |
| WO | 0166021 | 9/2001 |
| WO | 0166022 | 9/2001 |
| WO | 0182677 | 11/2001 |
| WO | WO01/82677 | 11/2001 |
| WO | 0191648 | 12/2001 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 2004014261 | 2/2004 |
| WO | 2004026170 | 4/2004 |
| WO | 2004075777 | 9/2004 |
| WO | 2005051231 | 6/2005 |
| WO | 2005512331 | 6/2005 |
| WO | 2006004885 | 1/2006 |
| WO | 2006091686 | 8/2006 |

OTHER PUBLICATIONS

Gray, Henry, Anatomy of the Human Body, 1918, 6d. The Foot 1. The Tarsus, II. Osteology, cover page and 12 pgs, ww. Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
APTA | Knee,/http://www.apta.org/AM/PrinerTemplate.cfm?Section=Home&TEMPLATE=/CM/HTMLDisplay.dfg&... Jun. 25, 2007 (1page).
American Machinist, Full-radius milling cutters, http://www.americanmachinist.com/Classes/Article/ArticleDraw_P.aspx, Jun. 26, 2007 (1 page).
Chuck (engineering),Wikipedia, the free encyclopedia, http://en.wikipedia.org/w/index.php?title=Chuck_%28engineering%29&printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Makita Industrial Power Tools, Product Details Print Out, Chain Mortiser, http://www.makita.com/menu.php?pg=product_det_prn&tag=7104L, Jun. 26, 2007 (3pgs).
Milling machine, Wikipedia, the free encyclopedia, http://en.wikipedia.org/w/index.php?title=Milling_machine&printable=yes, Jun. 26, 2007 (4 pages).
Mortise and tenon, Wikipedia, the free encyclopedia, http://en.wikipedia.org/w/index.php?title=Mortise_and_tenon&printable=yes, Jun. 25, 2007 (3 pages).
The Mini Uni: A New Solution for Arthritic Knew Pain and Disability, AORI, 4 pages, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw_angle&printable=yes, Jun. 25, 2007 (1 page).
Supplementary EPO Search Report for EPO Application No. 01932833.5 mailed Aug. 30, 2004.
European Communication pursuant to Article 96(2) EPC dated Sep. 11, 2006 received in corresponding European Patent Application Serial No. 01 932 833.5 (3 pages).
English language translation of Japanese Office Action dated Aug. 14, 2007, 3 pages.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.
International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
International Search Report and Written Opinion dated Aug. 8, 2007 issued in corresponding PCT patent application No. PCT/US06/29875.
Notice of Allowance issued in corresponding U.S. Appl. No. 10/308,718 dated Sep. 11, 2006.
Office Action issued in corresponding U.S. Appl. No. 11/326,133 dated Oct. 17, 2007.
Office Action issued in corresponding U.S. Appl. No. 10/741,044 dated Oct. 26, 2005.
USPTO Office Action dated Dec. 21, 2007 issued in corresponding U.S. Appl. No. 11/169,326.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.

USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
International Preliminary Examination Report dated Nov. 5, 2002 issued in corresponding PCT patent application No. PCT/US01/14061.
US Office Action issued in related U.S. Appl. No. 10/944,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
U.S. Office Action issued in related U.S. Appl. No. 11/326,133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/25284.
International Search Report and Written Opinion dated Aug. 8, 2008 issued in related International Patent Application No. PCT/US08/53988.
U.S. Office Action issued in related U.S. Appl. No. 10/994,453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice of Allowance received in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action received in related U.S. Appl. No. 11/169,326 dated Jun. 30, 2008.
U.S. Office Action received in related U.S. Appl. No. 11/169,326 dated Jul. 27, 2007.
U.S. Office Action received in related U.S. Appl. No. 11/169,326 dated Apr. 17, 2007.
U.S. Office Action received in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/944,453 dated Sep. 3, 2008.
United States Office Action issued is related U.S. Appl. No. 10/760,965 dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
Habermeyer, "Eclipse, Schaftfreie Schulterprothese Operationsanleitung," (dated unknown).
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.

International Search Report and Written Opinion dated Oct. 9, 2008 issued in related International Patent Application No. PCT/US07/82262.

European Search Report dated Nov. 4, 2008 issued in related European Patent Application No. 04811836.8-2310.

U.S. Office Action dated Jan. 9, 2009 issued in related U.S. Appl. No. 10/373,463.

Canadian Office Action dated Dec. 9, 2008 issued in related Canadian Patent Application No. 2407440.

Supplemental European Search Report dated Nov. 6, 2008 issued in related European Patent Application No. 05791453.3-2310.

Japanese Office Action dated Dec. 19, 2008 issued in Japanese Patent Application No. 2006501193.

Japanese Office Action dated Jan. 13, 2009 issued in Japanese Patent Application No. 2003552147.

International Search Report dated Jan. 30, 2006 issued in related International Patent Application No. PCT/US04/39181.

U.S. Office Action dated Mar. 27, 2009 issued in related U.S. Appl. No. 11/169,326.

European Office Action dated Feb. 26, 2009 in related European Patent Application No. 05791453.3.

McCarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).

Bushnell, et al., "Bony Instability of the Shoulder," Arthroscopy, The Journal of Arthroscopic and related Surgery, vol. 24, No. 9; Sep. 2005 (pp. 1061-1073).

Scalise, et al., "Resurfacing Arthroplasty of the Humerus: Indications, Surgical Technique, and Clinical Results," Techniques in Shoulder and Elbow Surgery 8(3):152-160; 2007.

Davidson, et al., "Focal Anatomic Patellofemoral Inlay Resurfacing: Theoretic Basis, Surgical Technique, and Case Reports," Orthop. Clin. N. Am., 39 (2008) pp. 337-346.

Provencher, et al., "Patellofemoral Kinematics After Limited Resurfacing of the Trochlea," The Journal of Knee Surgery, vol. 22 No. 2 (2008) pp. 1-7.

Dawson, et al., "The Management of Localized Articular Cartilage Lesions of the Humeral Head in the Athlete," Operative Techniques in Sports Medicine, vol. 16, Issue 1, pp. 14-20 (2008).

Uribe, et al., "Partial Humeral Head Resurfacing for Osteonecrosis," Journal of Shoulder and Elbow Surgery, (2009) 6 pages.

Burks, "Implant Arthroplasty of the First Metatarsalphalangeal Joint," Clin. Podiatr. Med. Surg., 23 (2006) pp. 725-731.

Hasselman, et al., "Resurfacing of the First Metatarsal Head in the Treatment of Hallux Rigidus," Techniques in Foot & Ankle Surgery 7(1):31-40, 2008.

Gelenkoberflachen, et al., "Partial hemi-resurfacing of the hip joint—a new approach to treat local osteochondral defects?" Biomed Tech 2006; 51:371-376 (2006).

Sullivan, "Hallux Rigidus: MTP Implant Arthroplasty," Foot Ankle Clin. N. Am. 14 (2009) pp. 33-42.

Cook, et al., "Meta-analysis of First Metatarsophalangeal Joint Implant Arthroplasty," Journal of Foot and Ankle Surgery, vol. 48, Issue 2, pp. 180-190 ( 2009).

Derner, "Complications and Salvage of Elective Central Metatarsal Osteotomies," Clin. Podiatr. Med. Surg. 26 (2009) 23-35.

Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.

Beecher, et al. "Effects of a contoured articular prosthetic device on tibiofemoral peak contact pressure: a biomechanical study," Knee Surg Sports Traumatol Arthrosc. Jan. 2008; 16(1): 56-63.

United States Office Action dated May 13, 2009 issued in related U.S. Appl. No. 11/359,892.

United States Office Action dated May 18, 2009 issued in related U.S. Appl. No. 11/209,170.

United States Office Action dated May 1, 2009 issued in related U.S. Appl. No. 11/461,240.

Australian Office Action dated Jan. 29, 2009 issued in related Australian Patent Application No. 2004216106.

European Search Report dated Apr. 22, 2009 issued in related European Patent Application No. 09002088.4.

U.S. Office Action dated Aug. 30, 2006 issued in related U.S. Appl. No. 10/618,887.

U.S. Office Action dated Jan. 15, 2008 issued in related U.S. Appl. No. 10/618,887.

U.S. Office Action dated May 18, 2009 issued in related U.S. Appl. No. 11/209,170.

U.S. Office Action dated May 28, 2009 issued in related U.S. Appl. No. 11/359,891.

U.S. Office Action dated May 13, 2009 issued in related U.S. Appl. No. 11/359,892.

International Search Report and Written Opinion dated Jun. 1, 2009 issued in related International Patent Application No. PCT/US2009/035889.

International Preliminary Report and Patentability dated May 7, 2009 issued in related International Patent Application No. PCT/US2007/082262.

Supplemental European Search Report dated May 28, 2009 issued in related International European Patent Application No. 01997077.1.

Supplemental European Search Report dated May 11, 2009 issued in related International European Patent Application No. 02805182.9.

Notice of Allowance dated Feb. 20, 2009 issued in related U.S. Appl. No. 10/618,887.

Notice of Reasons for Rejection issued in related Japanese Patent Application No. 2003-394702 mailed Jul. 21, 2009.

Notice of Reasons for Rejection issued in related Japanese Patent Application No. 20-541615 mailed May 26, 2009.

International Preliminary Report on Patentability issued in related International Patent Application No. PCT/US/2007/025284 dated Jun. 25, 2009.

Office Action issued in related Australian Patent Application No. 2007216648 dated Jul. 28, 2009.

European Search Report dated Jul. 10, 2009 issued in related European Patent Application No. 09002088.4.

International Preliminary Report on Patentability dated Aug. 20, 2009 issued in related International Patent Application No. 2008053194.

Notice of Allowance dated Aug. 27, 2009 issued in related U.S. Appl. No. 10/760,965.

* cited by examiner

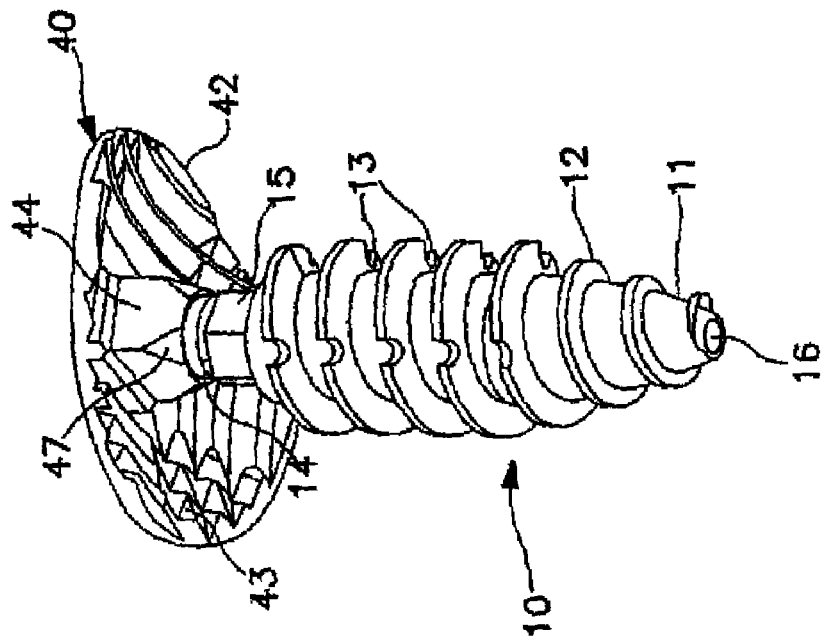
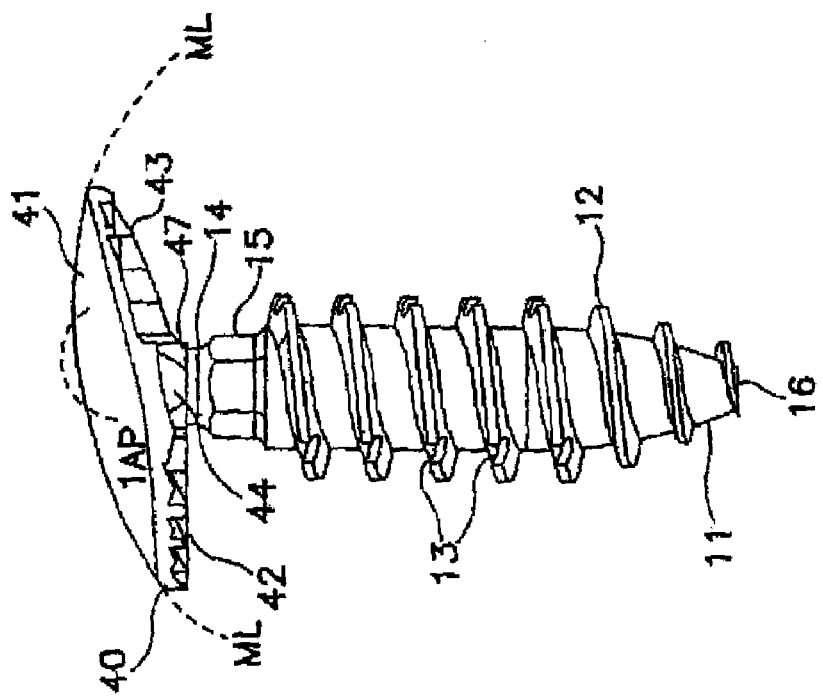

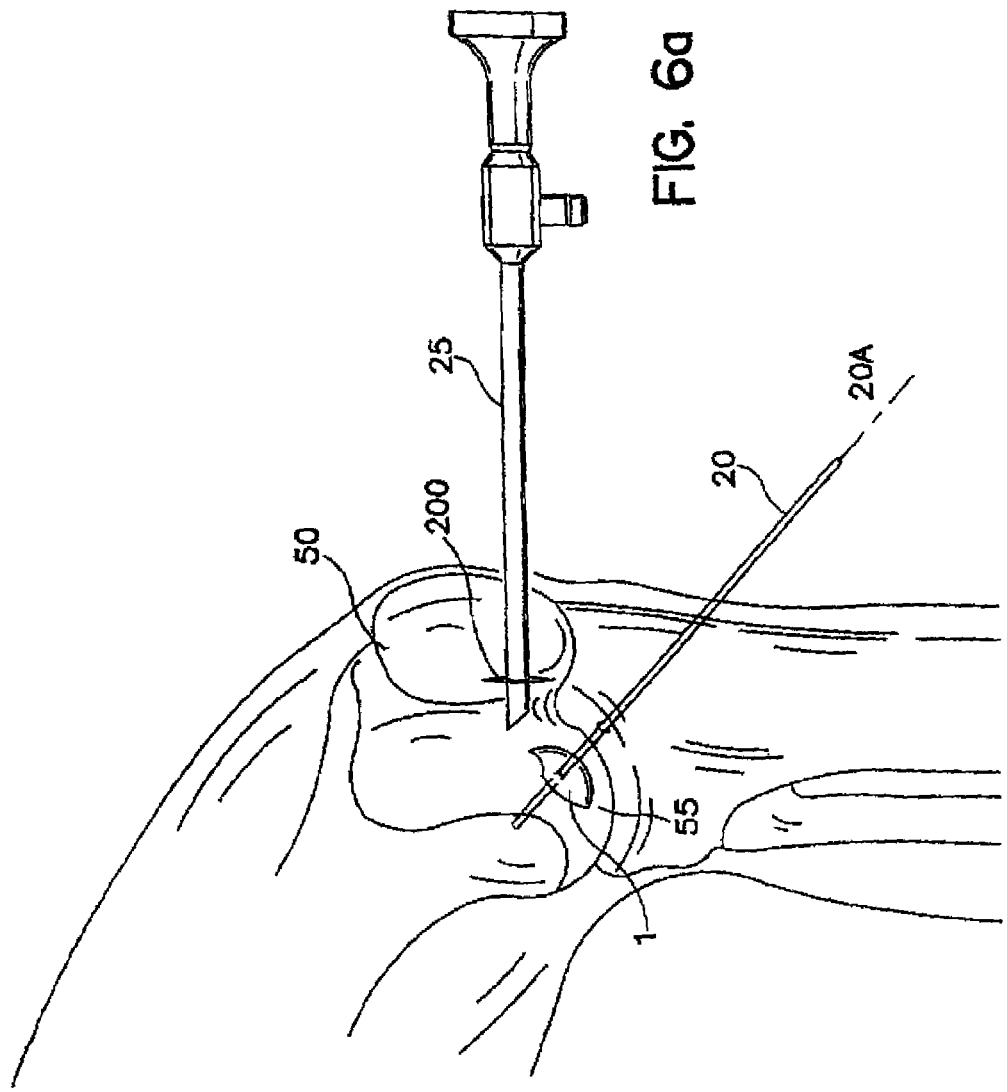

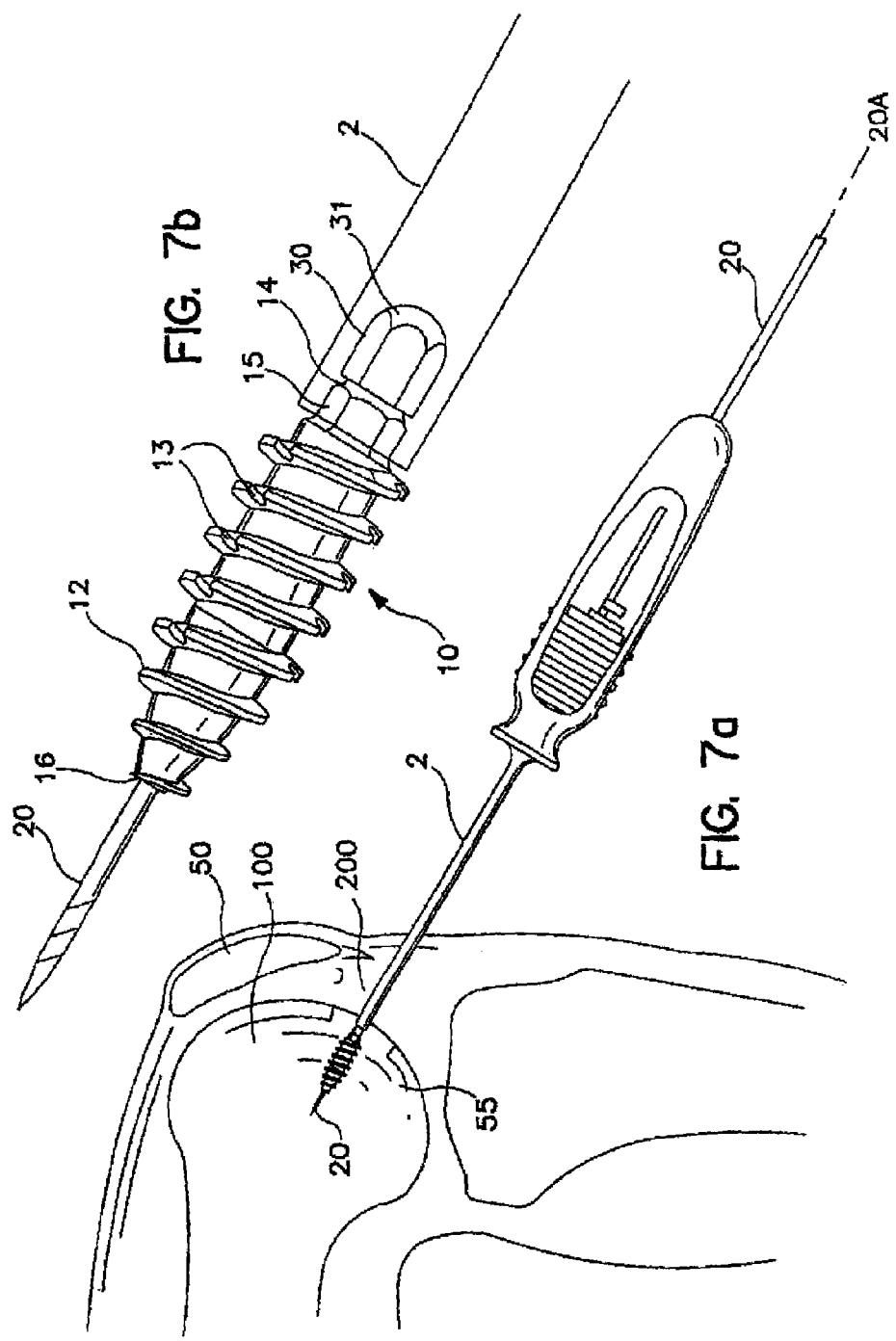

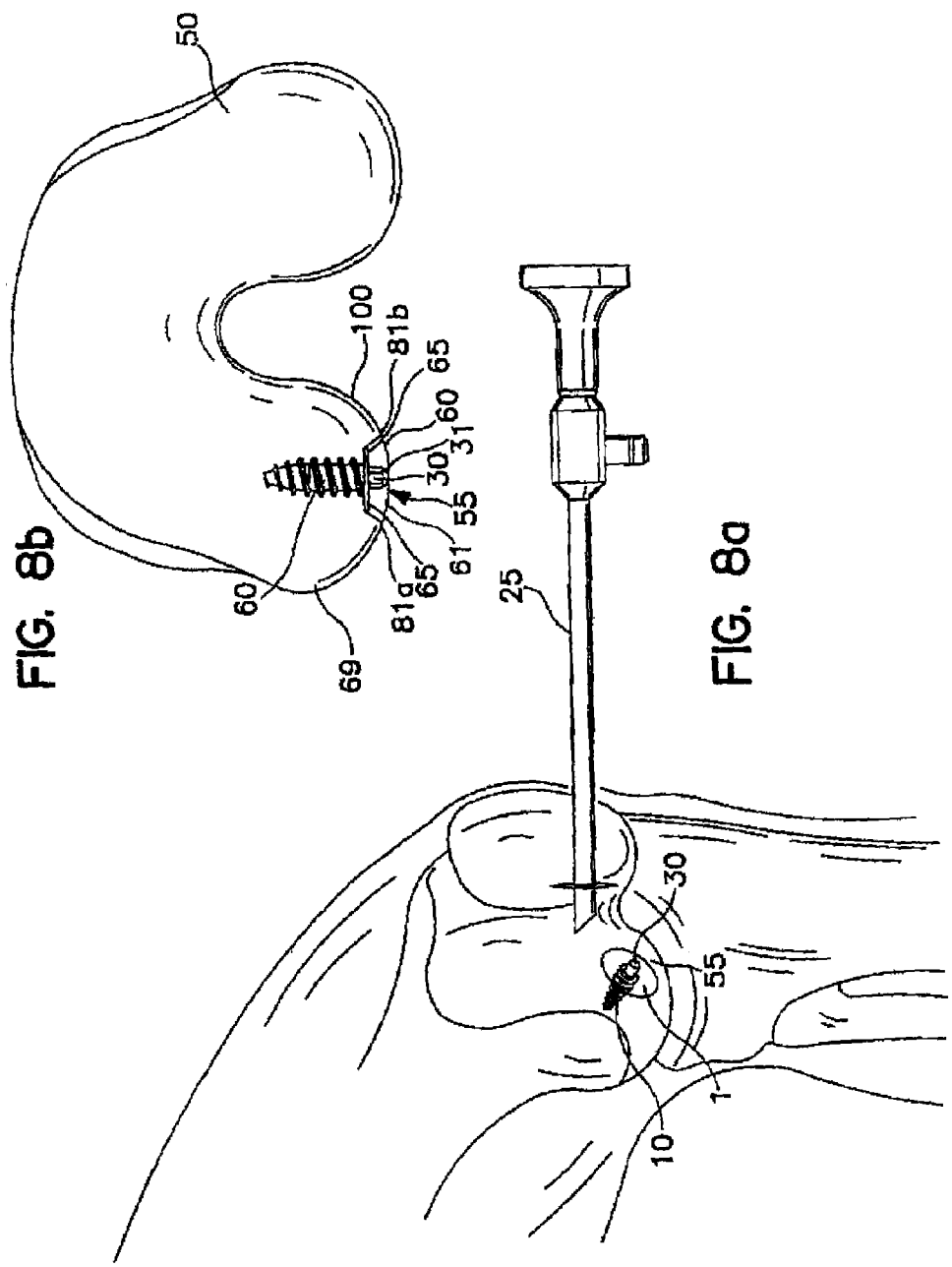

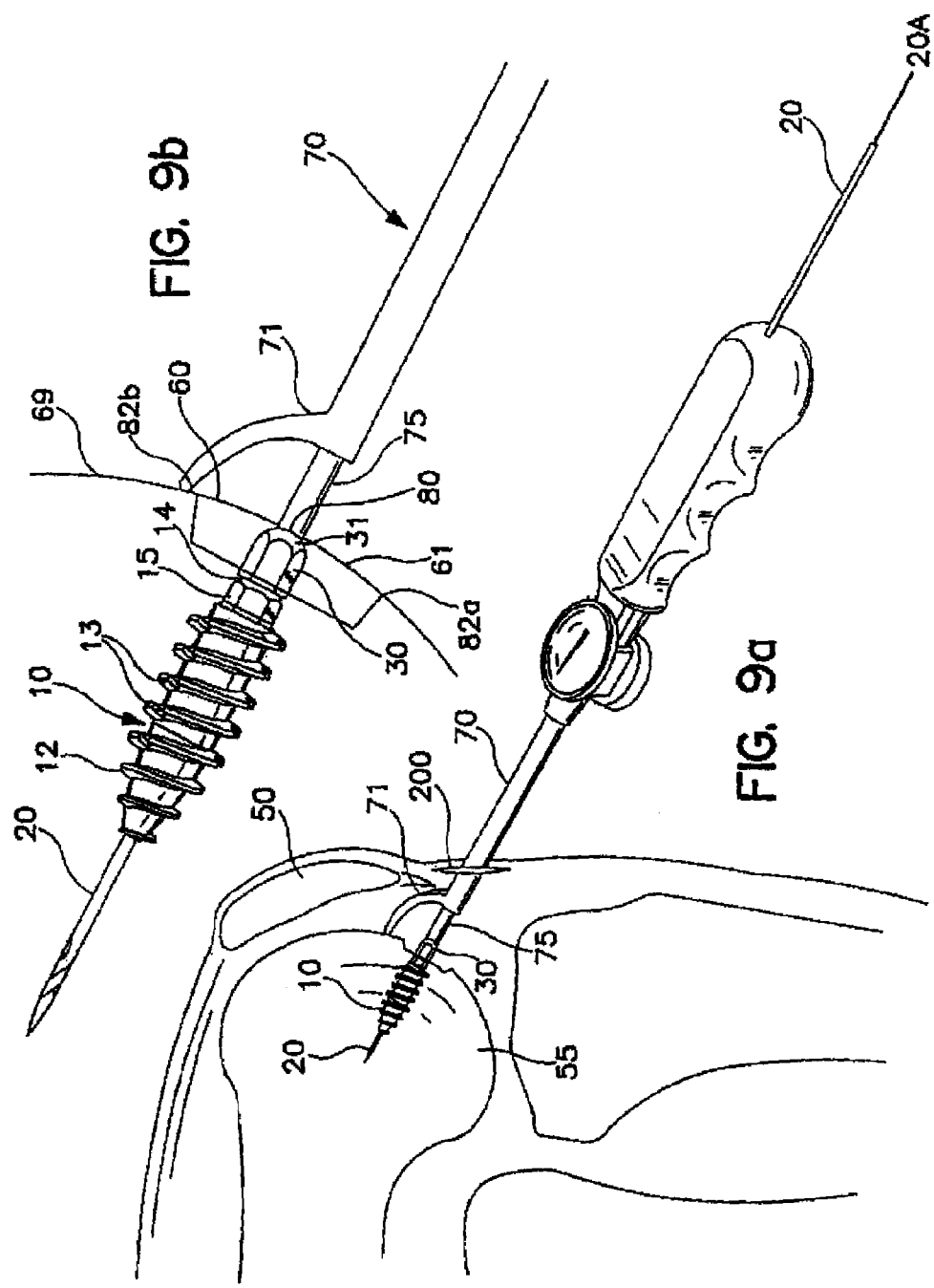

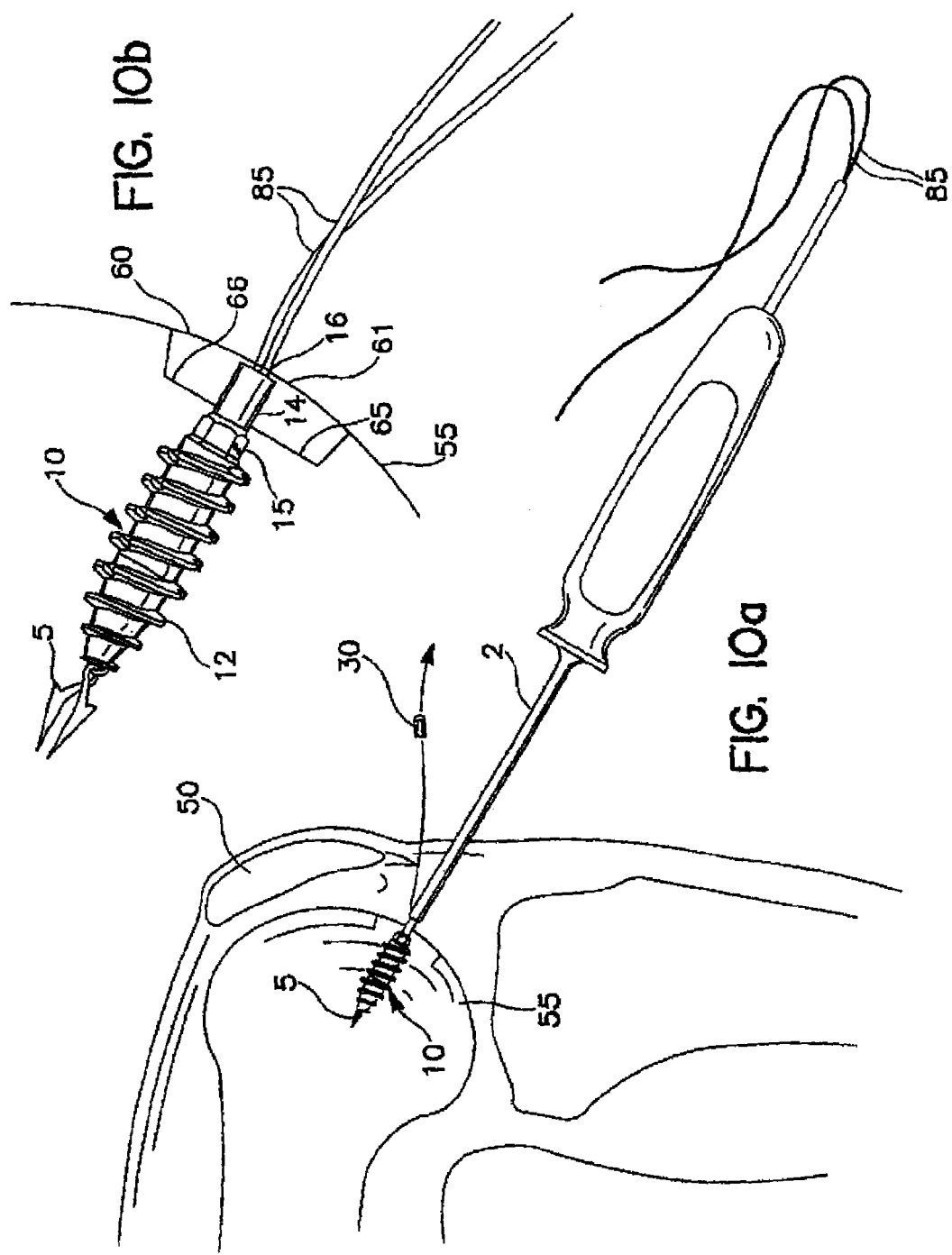

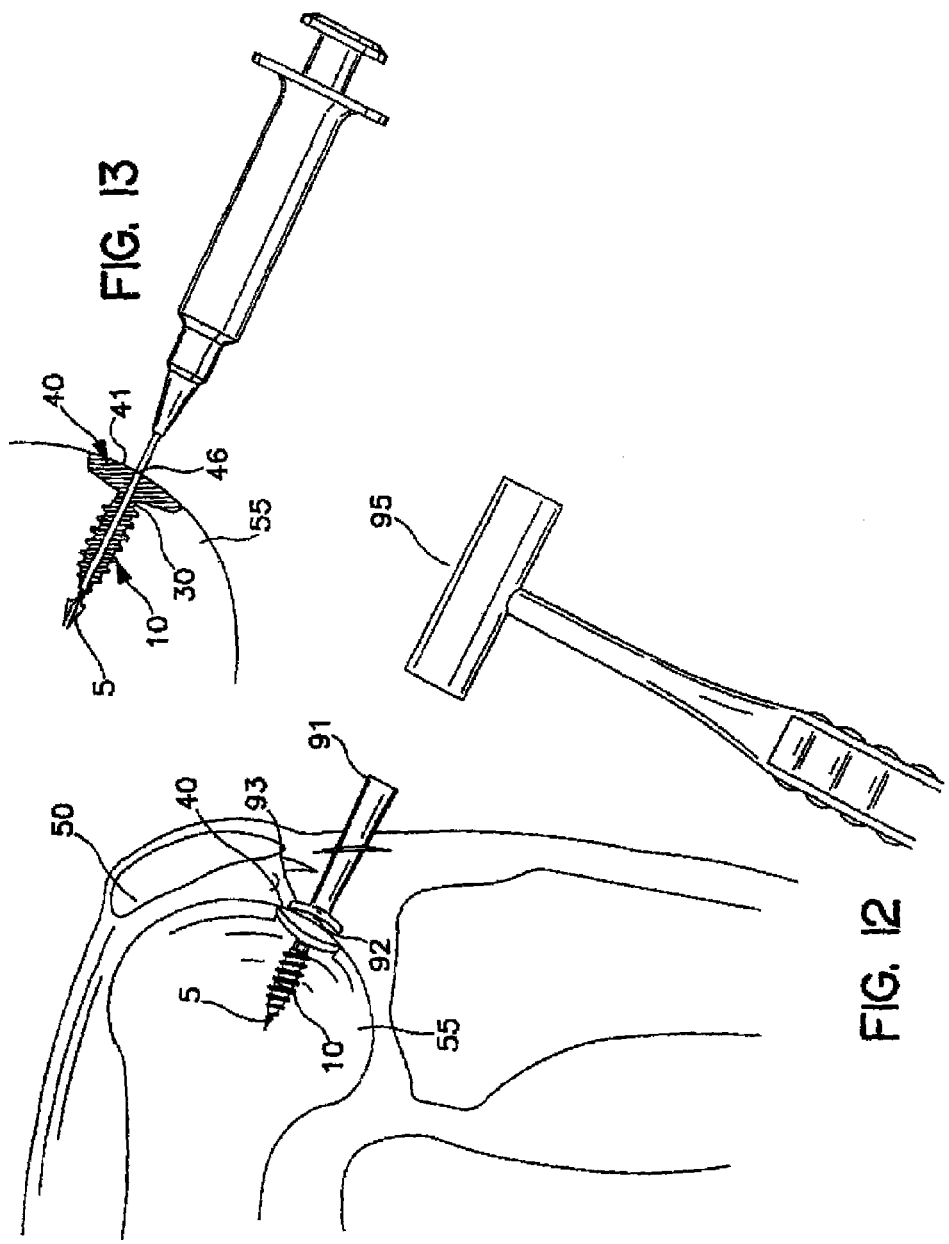

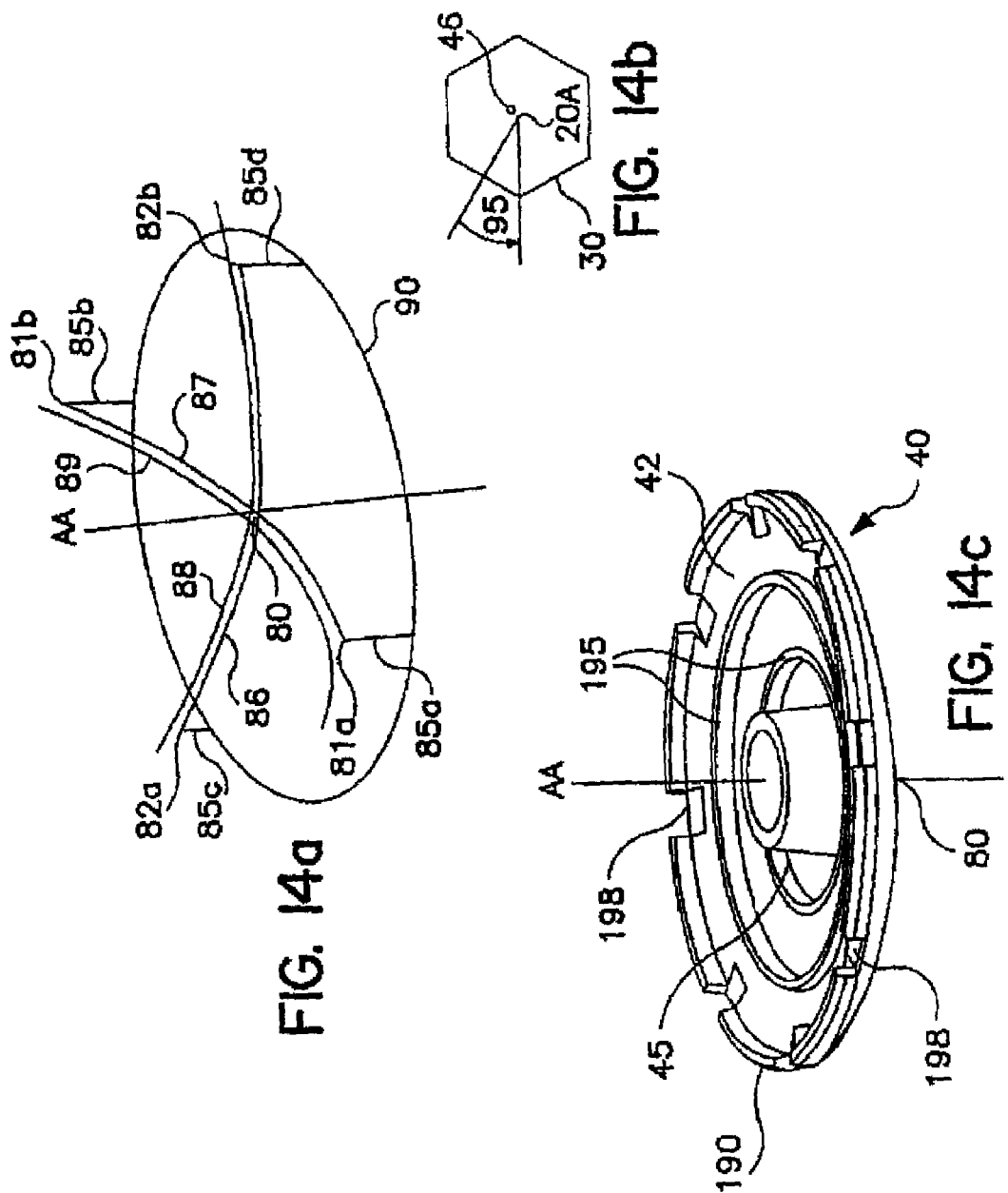

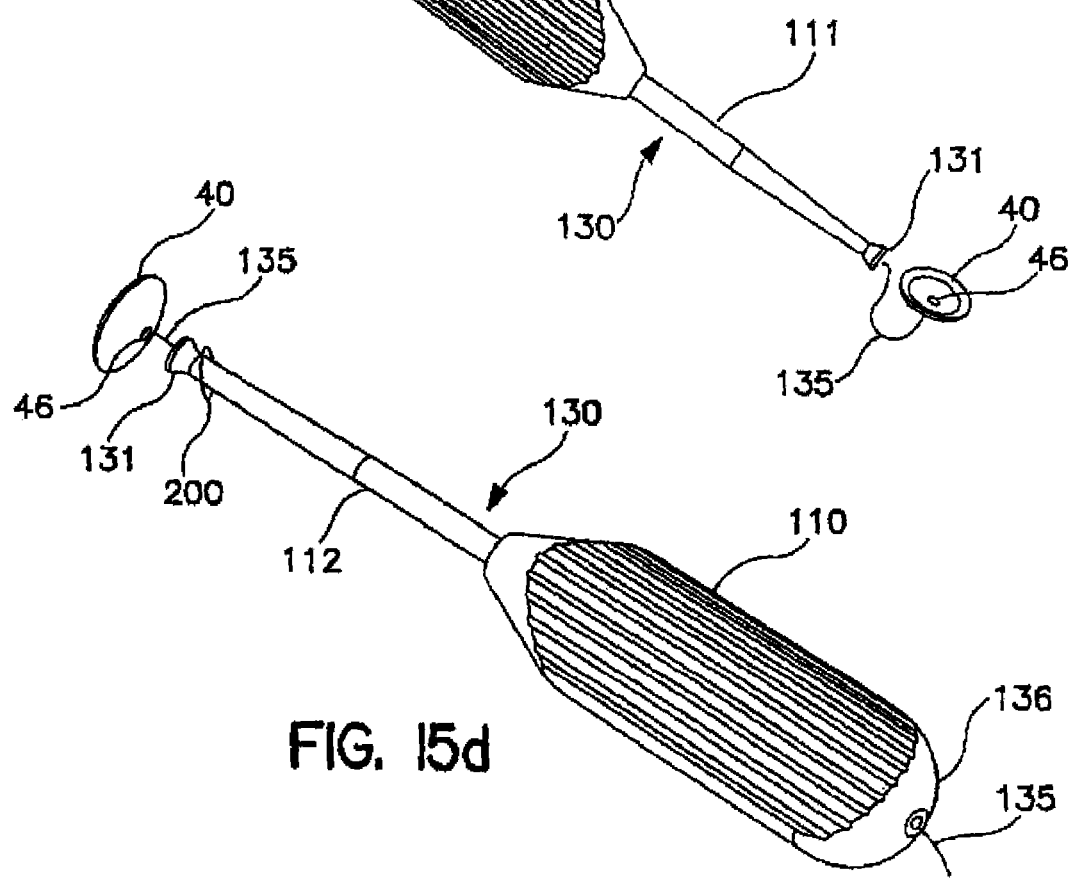

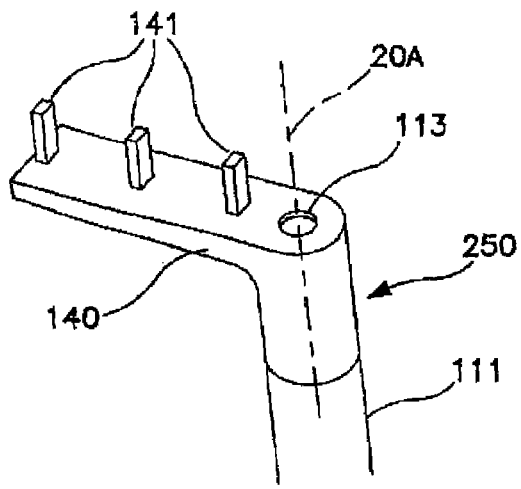
FIG. 18a
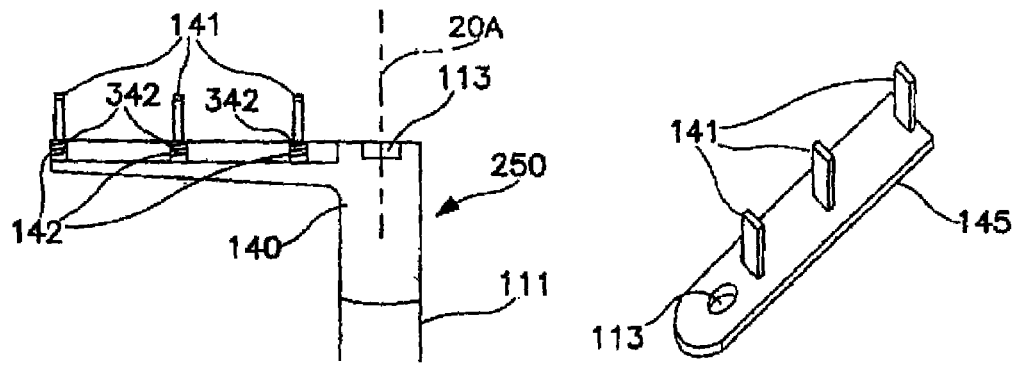
FIG. 18b
FIG. 18c
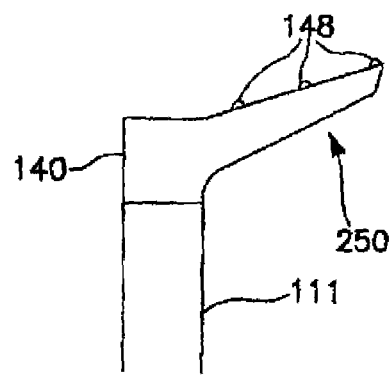
FIG. 18d

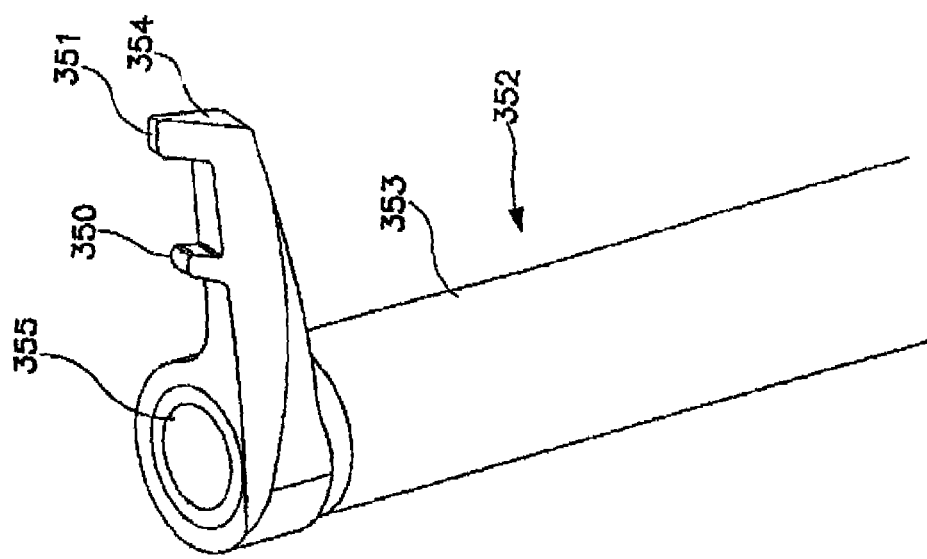

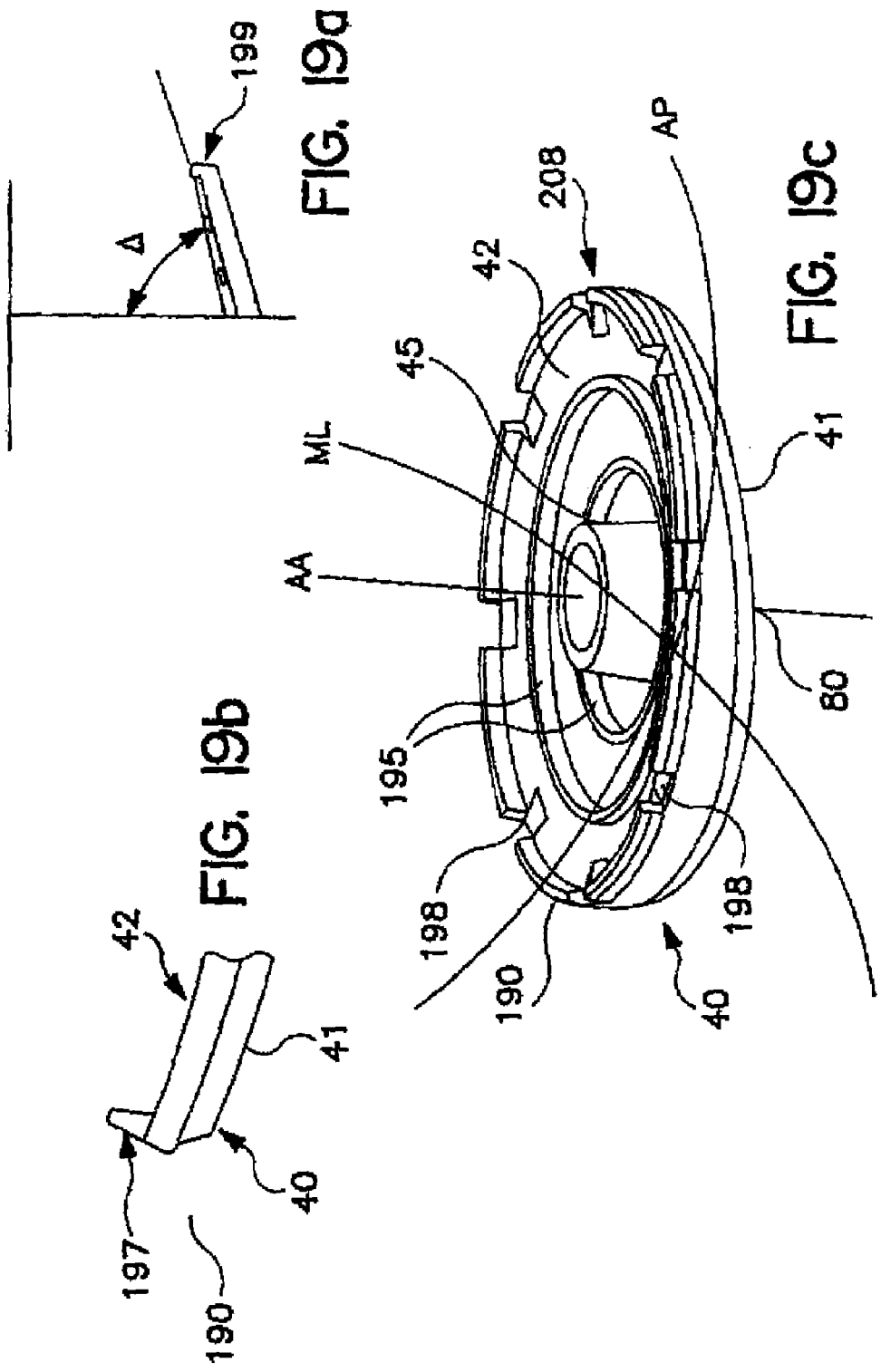

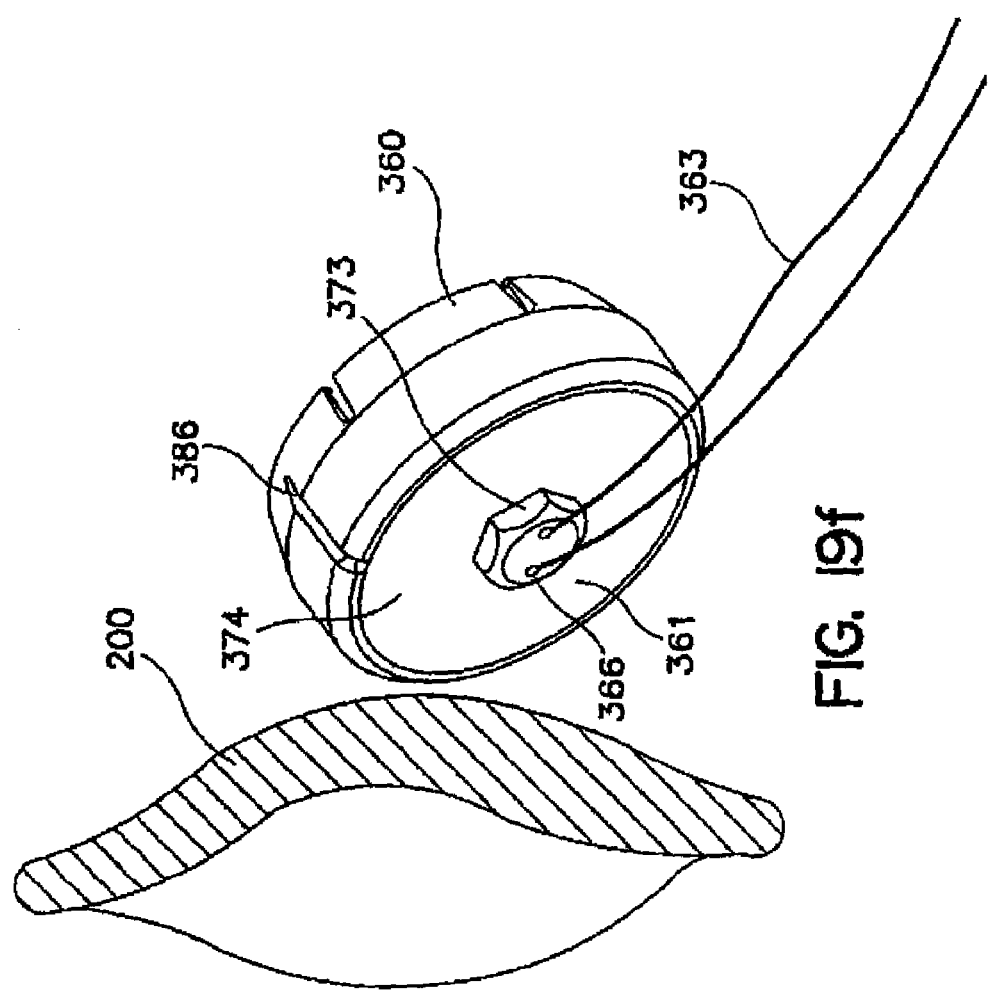

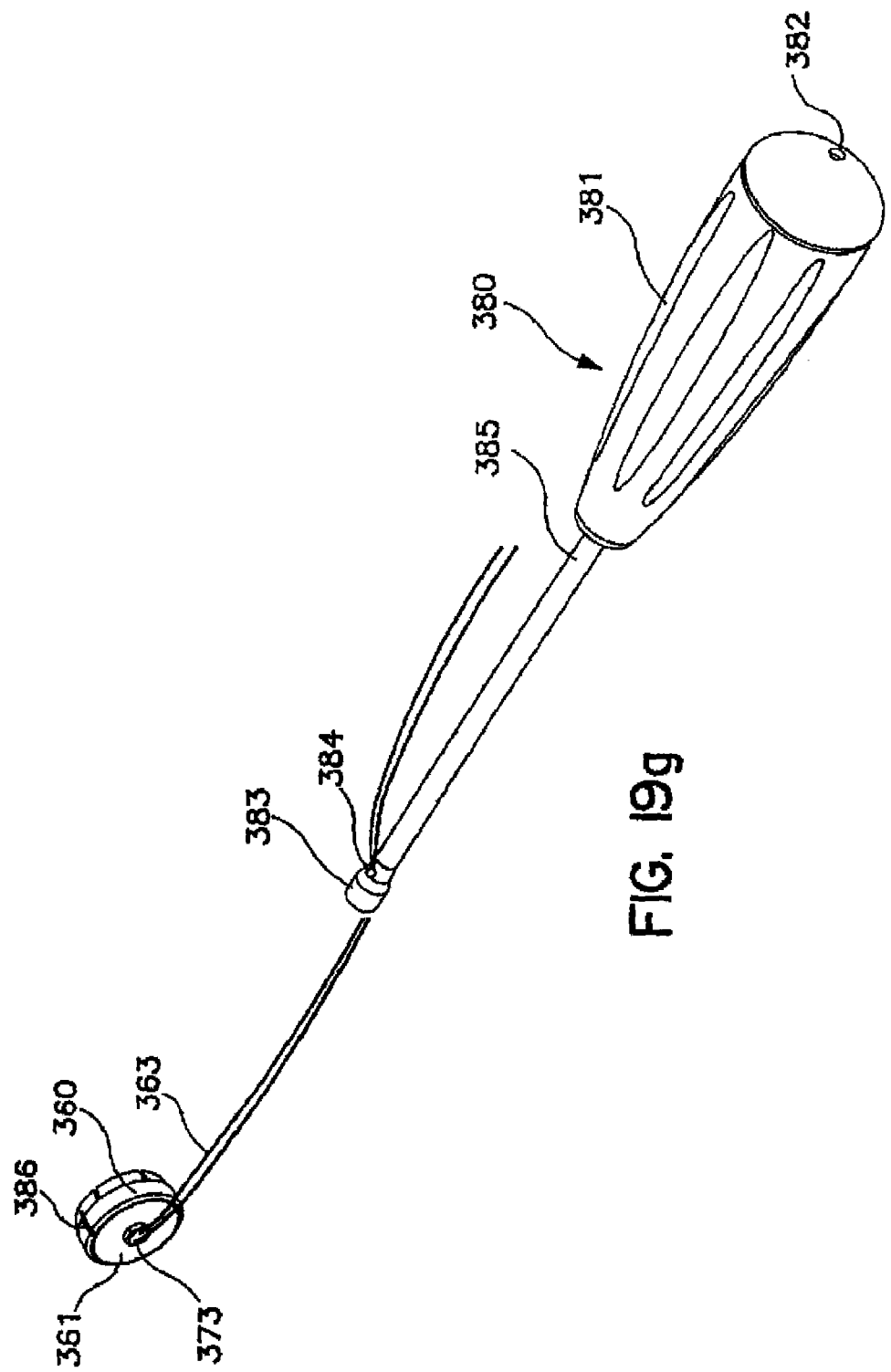

SYSTEM AND METHOD FOR JOINT RESURFACE REPAIR

CROSS-REFERENCE TO RELATED APPLICATIONS

This application is a continuation of U.S. patent application Ser. No. 10/360,228, filed Feb. 6, 2003, now U.S. Pat. No. 7,029,479, which is a divisional of U.S. patent application Ser. No. 09/846,657, now U.S. Pat. No. 6,520,964, filed May 1, 2001, which claims benefit of U.S. provisional application Ser. No. 60/201,049, filed May 1, 2000.

FIELD OF THE INVENTION

This invention relates to devices and methods for the repair of defects that occur in articular cartilage on the surface of bones, particularly the knee.

BACKGROUND OF THE INVENTION

Articular cartilage, found at the ends of articulating bone in the body, is typically composed of hyaline cartilage, which has many unique properties that allow it to function effectively as a smooth and lubricious load-bearing surface. However, when injured, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

Hyaline cartilage problems, particularly in knee and hip joints, are generally caused by disease such as occurs with rheumatoid arthritis or wear and tear (osteoarthritis), or secondary to an injury, either acute (sudden), or recurrent and chronic (ongoing). Such cartilage disease or deterioration can compromise the articular surface causing pain and further deterioration of joint function. As a result, various methods have been developed to treat and repair damaged or destroyed articular cartilage.

For smaller defects, traditional options for this type of problem include non-operative therapies (e.g., oral medication or medication by injection into the joint), or performing a surgical procedure called abrasion arthroplasty or abrasion chondralplasty. The principle behind this procedure is to attempt to stimulate natural healing. At the defect site, the bone surface is abraded, removing approximately 1 mm. or less using a high-speed rotary burr or shaving device. This creates an exposed subchondral bone bed that will bleed and will initiate a fibrocartilage healing response. Although this procedure has been widely used over the past two decades and can provide good short term results, (1-3 years), the resulting fibrocartilage surface is seldom able to support long-term weight bearing, particularly in high-activity patients, and is prone to wear.

Another procedure, referred to as the "microfracture" technique, incorporates similar concepts of creating exposed subchondral bone. During the procedure, the cartilage layer of the chondral defect is removed. Several pathways or "microfractures" are created to the subchondral bleeding bone bed by impacting a metal pick or surgical awl at a minimum number of locations within the lesion. By establishing bleeding in the lesion and by creating a pathway to the subchondral bone, a fibrocartilage healing response is initiated, forming a replacement surface. Results for this technique are generally similar to abrasion chondralplasty.

Another known option to treat damaged articular cartilage is a cartilage transplant, referred to as a Mosaicplasty or osteoarticular transfer system (OATS) technique. This involves using a series of dowel cutting instruments to harvest a plug of articular cartilage and subchondral bone from a donor site, which can then be implanted into a core made into the defect site. By repeating this process, transferring a series of plugs, and by placing them in close proximity to one another, in mosaic-like fashion, a new grafted hyaline cartilage surface can be established. The result is a hyaline-like surface interposed with a fibrocartilage healing response between each graft.

This procedure is technically difficult, as all grafts must be taken with the axis of the harvesting coring drill being kept perpendicular to the articular surface at the point of harvest. Also, all graft placement sites must be drilled with the axis of a similar coring tool being kept perpendicular to the articular surface at the point of implantation. Further, all grafts must be placed so that the articular surface portion of these cartilage and bone plugs is delivered to the implantation site and seated at the same level as the surrounding articular surface. If these plugs are not properly placed in relation to the surrounding articular surface, the procedure can have a very detrimental effect on the mating articular surface. If the plugs are placed too far below the level of the surrounding articular surface, no benefit from the procedure will be gained. Further, based on the requirement of perpendicularity on all harvesting and placement sites, the procedure requires many access and approach angles that typically require an open field surgical procedure. Finally, this procedure requires a lengthy post-operative non-weight bearing course.

Transplantation of previously harvested hyaline cartilage cells from the same patient has been utilized in recent years. After the cartilage is removed or harvested, it is cultured in the lab to obtain an increase in the number of cells. These cells are later injected back into the focal defect site and retained by sewing a patch of periosteal tissue over the top of the defect to contain the cells while they heal and mature. The disadvantages of this procedure are its enormous expense, technical complexity, and the need for an open knee surgery. Further, this technique is still considered somewhat experimental and long-term results are unknown. Some early studies have concluded that this approach offers no significant improvement in outcomes over traditional abrasion and microfracture techniques.

U.S. Pat. No. 5,782,835 to Hart et al. discloses an apparatus and method for repair of articular cartilage including a bone plug removal tool, and a bone plug emplacement tool. The method of repairing defective articular cartilage includes the steps of removing the defective cartilage and forming a hole of sufficient depth at the site. A bone plug comprising intact bone and cartilage adhering thereto is removed from a bone lacking defective cartilage is placed in the hole at the site of the damage.

U.S. Pat. No. 5,413,608 to Keller discloses a knee joint endoprosthesis for replacing the articular surfaces of the tibia comprising a bearing part which is anchored on the bone having an upper bearing surface and a rotatable plateau secured on the bearing surface and forming a part of the articular surface to be replaced. A journal rises from the bearing surface and cooperates with a bore in the plateau to provide lateral support.

U.S. Pat. No. 5,632,745 to Schwartz describes a method of surgically implanting into a site a bio-absorbable cartilage repair assembly. The assembly includes a bio-absorbable polygonal T-shaped delivery unit having radial ribs to be mounted in the removed area and a porous bio-absorbable insert supported by and in the delivery unit. The method comprises the steps of preparing the site to receive the assembly by removing a portion of the damaged cartilage and preparing the site to receive the assembly by drilling and countersinking the bone. The assembly is inserted and seated using an impactor in the drilled and countersunk hole in the bone until the assembly is flush with the surrounding articular surface.

U.S. Pat. No. 5,683,466 to Vitale illustrates an articular joint surface replacement system having two opposing components. Each component has a tapered head piece for covering the end of a bone and for acting as an articular surface, an integrally formed screw stem of sufficient length to extend into the bone and inwardly angled bone grips on the underside of the head piece to allow fixation to the bone by compression fit. The partially spherical convex shaped exterior of the first component complements the partially spherical concave shaped exterior of the second component.

U.S. Pat. No. 5,702,401 to Shaffer discloses an intra-articular measuring device including a hollow handle defining a first passageway and a hollow tube having a second passageway extending from the handle, the hollow tube carrying a projection at its distal end for seating on a fixed site and a probe disposed at the distal end of the hollow tube which may be directed to a second site, to enable measurement of the distance between the first and second sites.

U.S. Pat. No. 5,771,310 to Vannah describes a method of mapping the three-dimensional topography of the surface of an object by generating digital data points at a plurality of sample points on said surface, each digital data point including a property value and a position value corresponding to a particular point representing the properties of the surface of the object. A 3-D transducer probe (e.g., a digitizer) is moved on or over the surface along a random path, and the sample points are digitized to generate a real-time topography or map on a computer screen of selected properties of the object, including without limitation, surface elevation, indentation stiffness, elevation of sub-surface layers and temperature.

Prosthetics for total knee replacement (TKR), whereby the entire knee joint or a single compartment of the knee joint is replaced can be a common eventuality for the patient with a large focal defect. Although these patients are also managed with anti-inflammatory medications, eventual erosion of the remaining articular cartilage results in effusion, pain, and loss of mobility and/or activity for the patient. Problems encountered after implanting such prostheses are usually caused by the eventual loosening of the prosthetic due to osteolysis, wear, or deterioration of the cements used to attach the device to the host bones. Further, some prostheses used are actually much larger than the degenerated tissue that needs to be replaced, so that extensive portions of healthy bone are typically removed to accommodate the prostheses. Patients who undergo TKR often face a long and difficult rehabilitation period, and the life span of the TKR is accepted to be approximately 20 years. Accordingly, efforts are made to forgo the TKR procedure for as long as possible.

Accordingly, there is a need for an improved joint surface replacement system that would be effective in restoring a smooth and continuous articulating surface and that would also be as durable as the former hyaline cartilage surface, within the context of a minimally invasive procedure that allows for a nearly immediate return to activity, restoration of lifestyle, and pain relief.

SUMMARY OF THE INVENTION

The present invention provides tools and methods for mapping and measuring the articular surface of a joint (or of any bony surface) and for fabricating a prosthetic device based on this recorded data.

In one method consistent with the invention, once the defect of the chondral surface has been identified, a guide pin is inserted arthroscopically. A fixation screw having a tapered distal tip and an aggressive distal end thread form is then driven into the subchondral bone in relation to a reference axis that is approximately central to the defect. The fixation device also serves to define a tangent point to the surrounding articular surface. The screw is driven by a socket type driver that engages a hex-shaped proximal extension. A further cylindrical proximal extension of the screw (or other mating feature, e.g., a recess in the screw) that eventually serves as a fixation element for the surface prosthetic is at this time concealed with a cover (or other mating feature corresponding to the mating feature of the screw, e.g., a plug for mating with a screw having a recess as its mating feature) having a radiused proximal end. One or more milled slots run the length of the uniform diameter portion of the screw.

Under arthroscopic view, the screw depth is adjusted so that the radiused cover surface is positioned tangent to the radius that defines the existing articular surface. At this time, the guide pin is removed and the knee is articulated. The depth positioning of the radiused cover establishes an origin or reference point for all future measuring, cutting, and prosthetic machining operations. Arthroscopic examination is carried out to confirm positioning.

A measuring tool is inserted on the reference axis. A central element of the measuring tool is a static post that establishes the axial location of origin. By rotating the outer arm or outrigger of the measuring tool relative to the static post while also maintaining contact with the articular surface, an axial displacement or Z dimension can be established relative to the origin for any point along the known radial sweep of the outrigger to determine the final geometry of the prosthetic surface which fits within the defect. These Z dimensions can be recorded in real time with conventional dial gauge indicators, or with digital recording devices, or by using marking techniques. Although numerous points may be taken, ideally a minimum number of points are taken to accurately define the target articular surface.

Locating surfaces or features created on the screw, (or alternatively, on the radius cover, as described in alternative embodiments herein), correlate to some surface or feature on the measuring tool and allow the measurement of the rotational position of the points about the axis with respect to the locating surfaces. Data recorded during the mapping procedure can then be entered into parametric engineering design software or similar algorithm to define a three dimensional surface matched to the bearing surface geometry to be implanted and reproduce the anatomic contours mapped.

An alternative measuring device for obtaining the articular surface dimension includes an outer marking element and an inner recording element. The marking element includes a sharp indenting mechanism which when pressed by the surgeon creates a depression or mark in the relatively soft surface of the recording element, which deforms at these marked points so that they can be utilized as patient data. The recording element also includes a surface that corresponds to the surface of the proximal extension of the fixation screw. During the mapping procedure, data points are established of the rotational position of the mapped articular surface relative to the screw. These data points are translated to the implant geometry so that the accurate rotational location of the implant relative to the screw is maintained.

In order to secure the implant to the fixation screw, a precision taper (or other component of a mating feature) is machined into a protrusion (or other component of a mating feature) on the back of the device. The implant may be constructed of cobalt chromium, or other materials. The implant may also include a slight outward taper or protrusion along the diametrical surface to enhance load bearing or load transfer properties of the implant to surrounding bone. Additionally, a series of radial cuts may create surfaces that increase resistance of the implant to rotational forces. These features may be located around the outer diameter of the implant.

In another aspect, the invention includes a compass instrument for measurement and surface preparation of the implant target site subsequent sizing of the implant. This compass instrument is configured so that it can be delivered to the site arthroscopically, and when coupled to the axis defined by the guide pin it can be used for measuring and cutting operations.

In another embodiment, the compass instrument consists of a handle, a cannulated shaft that extends through the handle, and a cannulated distal offset arm configured to serve as a linearly adjustable mounting tool for a series of cutting blades, boring blades, or measuring probes.

With the guide pin advanced through the instrument shaft, when fitted with a blade, a fixed length from the rotational or reference axis to the cutting blade's cutting surface is established. This defines the radius that is effected as the instrument is rotated around the guide pin, and corresponds to the overall diameter of the implant. This sharp cutting blade is used to circumscribe and cleanly cut the surrounding articular cartilage.

In another aspect, the invention features a bone cutting or scoring instrument whereby the bone-cutting instrument is positioned on the guide pin reference axis and is used to prepare the target site to match in configuration and dimension the contacting surface of the implant. The matching fit between the bone surfaces of the prepared target site and the bone contacting surfaces of the implant can advantageously ensure long term clinical results with the implant, as poor quality of fit between bone surfaces and bone contacting surfaces of traditional orthopedic prosthetic devices has been noted to contribute to early clinical failures.

Following fabrication of the implant, a second surgical procedure is performed. The radiused cover is removed exposing a precision taper (or, alternatively, the cover may be removed during the first procedure). A pin with a distally mounted element is placed through the central lumen of the fixation screw so that the distally mounted element is secured into the screw. This element carries one or more suture strands that now trail from the fixation screw. The sutures are then threaded through the implant and a knot or bead may be created proximal to the implant. By continuing to manipulate and tension the suture strands, the implant can be brought coaxial to the fixation screw. Once coaxial, the implant is aligned via engagement of the keyed elements and driven into place with a plastic driving rod and mallet. Finally, through the guide aperture on the surface of the implant, bone cement may be injected to enhance the contact surface between the implant and the subchondral bone.

In another aspect, the invention further features a driver whereby the implant is connected to the driver via a holder and a tether element, such as a suture or wire. The implant and the driver are then inserted arthroscopically. Tension is then applied to the tether element so that the implant is drawn back and seated on the driver. The implant can then be controllably delivered to the prepared target site. The seat portion of the driver may comprise a material that may be impacted to seat the implant without damaging the implant surface.

DESCRIPTION OF THE DRAWINGS

FIG. 5a is a side view of an exemplary assembled fixation device and implant in one embodiment of the present invention;

FIG. 5b is a perspective view of an assembled fixation device and implant in one embodiment of the present invention;

FIG. 6a is a sectional view of a knee having damaged articular cartilage, showing an exemplary guide pin drilled into the central portion of the defect and an arthroscope being disposed adjacent thereto, in a surgical procedure consistent with one embodiment of the present invention;

FIG. 7a is a sectional view of a knee having damaged articular cartilage, showing an exemplary fixation screw being driven into the defect by an exemplary socket type driver arranged on the guide pin, in a surgical procedure consistent with one embodiment of the present invention;

FIG. 7b is a side view of the exemplary fixation screw, socket type driver and guide pin of FIG. 7a, illustrating the hex shaped proximal extension in a cross-sectional view, in a surgical procedure consistent with one embodiment of the present invention;

FIG. 8a is a perspective view of a knee having damaged articular cartilage, showing an exemplary fixation screw and hex-shaped proximal extension implanted in the defect after removal of an exemplary socket type driver and guide pin, in a surgical procedure consistent with one embodiment of the present invention;

FIG. 8b is a sagital view of the exemplary fixation screw and hex-shaped proximal extension of FIG. 8a implanted in the defect after removal of an exemplary socket type driver and guide pin, in a surgical procedure consistent with one embodiment of the present invention;

FIG. 9a is a sectional view of an exemplary fixation screw and hex-shaped proximal extension implanted in the defect with the exemplary guide pin replaced and an exemplary measuring tool arranged thereon, in a surgical procedure consistent with one embodiment of the present invention;

FIG. 9b is a side partial cross-sectional view of the exemplary fixation screw and hex-shaped proximal extension of FIG. 9a implanted in the defect with the exemplary guide pin replaced and an exemplary measuring tool arranged thereon, in a surgical procedure consistent with one embodiment of the present invention;

FIG. 10a is a sectional view of an exemplary fixation screw and hex-shaped proximal extension implanted in the defect, after removal of the hex-shaped proximal extension, with an exemplary pin and suture strands placed therethrough, in a surgical procedure consistent with one embodiment of the present invention;

FIG. 10b is a side partial cross-sectional view of the exemplary fixation screw and hex-shaped proximal extension of FIG. 10a, implanted in the defect, with an exemplary pin and suture strands placed therethrough, in a surgical procedure consistent with one embodiment of the present invention;

FIG. 11a is a sectional view of an exemplary fixation screw implanted in the defect, with an exemplary pin and suture strands placed therethrough, showing the implanted fixation screw with the implant being tensioned on the suture strands, in a surgical procedure consistent with one embodiment of the present invention;

FIG. 11b is a partial cross-sectional view of the exemplary fixation screw of FIG. 9a implanted in the defect, showing the implant positioned in the interchondular notch, in a surgical procedure consistent with one embodiment of the present invention;

FIG. 12 is a sectional view of an exemplary fixation screw implanted in the defect, wherein, after placement of the implant and removal of the suture strands, the implant is driven into place with an impactor and hammer, in a surgical procedure consistent with one embodiment of the present invention;

FIG. 13 is a side cross-sectional view of an exemplary fixation screw implanted in the defect, after placement of the implant, wherein, after removal of the impactor and hammer, cement is injected between the implant and the bone, in a surgical procedure consistent with one embodiment of the present invention;

FIG. 14a is a schematic representation of the two datum curves used to define a patient-specific three-dimensional surface for construction of the articular or lower surface of an implant in one embodiment of the present invention;

FIG. 14b is a top view of an exemplary hex-shaped proximal extension in one embodiment of the present invention;

FIG. 14c is a perspective view of the bone-contacting or upper surface of an exemplary implant, in one embodiment of the present invention;

FIG. 15c is a perspective view of an exemplary driver, showing an exemplary implant on an exemplary tether element, in one embodiment of the present invention;

FIG. 15d is a perspective view of an exemplary driver, showing an exemplary implant tensioned on an exemplary tether element, in one embodiment of the present invention;

FIG. 18a is a perspective view of an exemplary site preparation and cutting device, in one embodiment of the present invention;

FIG. 18b is a cross sectional view of the exemplary site preparation and cutting device of FIG. 18a, in one embodiment of the present invention;

FIG. 18c is a perspective view of another exemplary site preparation and cutting device, in one embodiment of the present invention;

FIG. 18d is a side view of another exemplary site preparation and cutting device, in one embodiment of the present invention;

FIG. 18e is a perspective view of another exemplary site preparation and cutting device, in one embodiment of the present invention;

FIG. 19a is a sectional view of the upper surface of an exemplary implant, in one embodiment of the present invention;

FIG. 19b is a side view of a portion of the exemplary implant of FIG. 19a, in one embodiment of the present invention;

FIG. 19c is a perspective view of the upper surface of the exemplary implant of FIG. 19a, in one embodiment of the present invention;

FIG. 19f is a bottom perspective view of the exemplary implant of FIG. 19d seated in the taper lock ring, with washer and suture, disposed within an incision near the defect site, in one embodiment of the present invention;

FIG. 19g is a perspective view of the exemplary implant of FIG. 19d seated in the taper lock ring, with washer and suture, wherein the suture is threaded through an aperture at the distal end of a seating tool, at a first point in time during the process of seating the implant into the defect site, in one embodiment of the present invention;

DETAILED DESCRIPTION OF THE EMBODIMENTS

Figure 1:
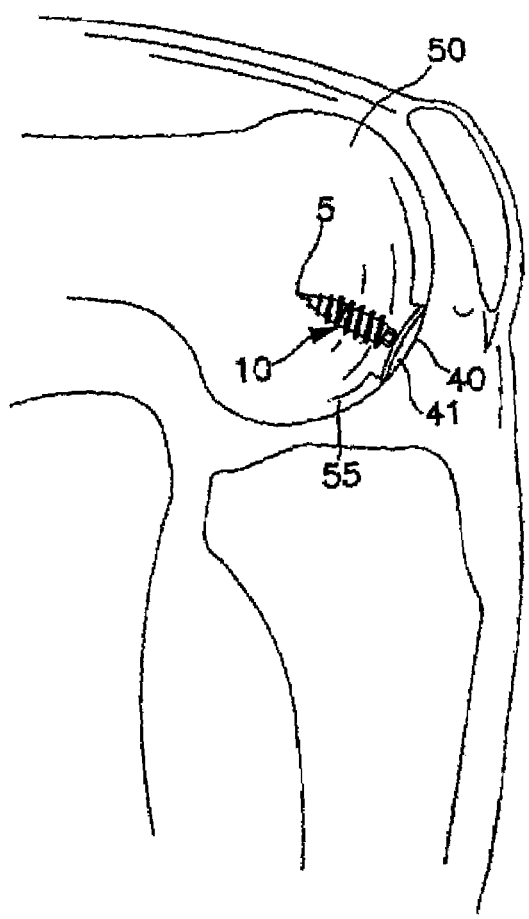
FIG. 1 is a fragmentary side view of a knee having therein an exemplary assembled fixation device and implant of the joint surface repair system surgically implanted by the method in one embodiment of the present invention.

As an overview, FIG. 1 shows a surgically implanted articular joint surface repair system consistent with the present invention. As shown, the assembled fixation device includes fixation screw 10, implant 40, and anchoring pin 5, implanted in the defect in the medial femoral chondral surface 55 of knee 50. Implant 40 is configured so that bearing or bottom surface 41 of the implant reproduces the anatomic contours of the surrounding articular surface of the knee 50.

Figure 2A:
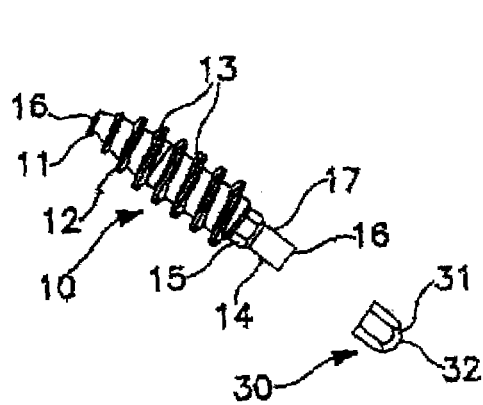
FIG. 2a is an exploded side view of an exemplary fixation screw and hex-shaped proximal extension in one embodiment of the present invention.
Figure 2B:
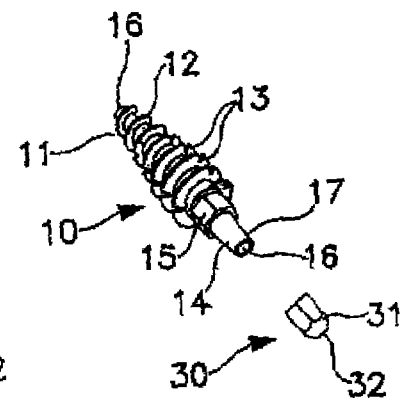
FIG. 2b is an exploded perspective view of an exemplary fixation screw and hex-shaped proximal extension in one embodiment of the present invention.
Figure 3A:
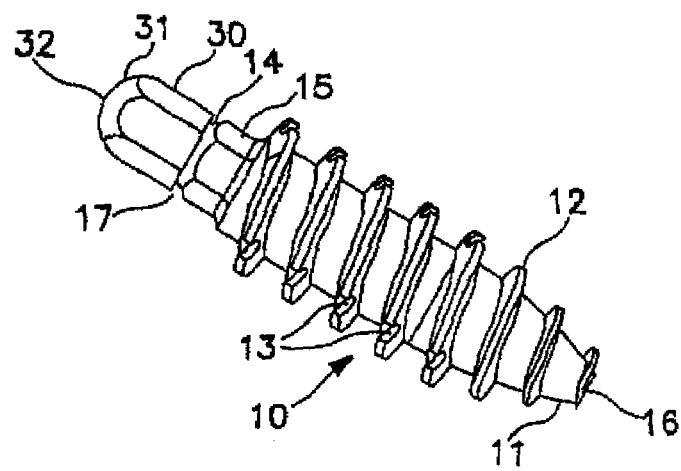
FIG. 3a is a side view of an exemplary assembled fixation screw and hex shaped extension in one embodiment of the present invention.

As illustrated in FIGS. 2*a*, 2*b* and 3*a*, fixation screw 10 comprises threads 12 running the length of the screw from tapered distal tip 11 to hex-shaped drive 15. In the embodiment shown, the screw includes a tapered distal end 11, and aggressive distal threads 12, so that, as screw 10 is driven into the subchondral bone 100 (as shown in FIG. 7*a*) the screw dilates open and radially compress the subchondral bone, increasing its local density and thereby increasing the fixation strength of the screw. The screw 10 may taper down to the distal end 11, and the diameter of the screw may become greater and more uniform at the center thereof, so that adjustment of the depth of the screw 10 with respect to the subchondral bone 100 does not significantly further increase or decrease the compression of the subchondral bone.

Figure 8C:
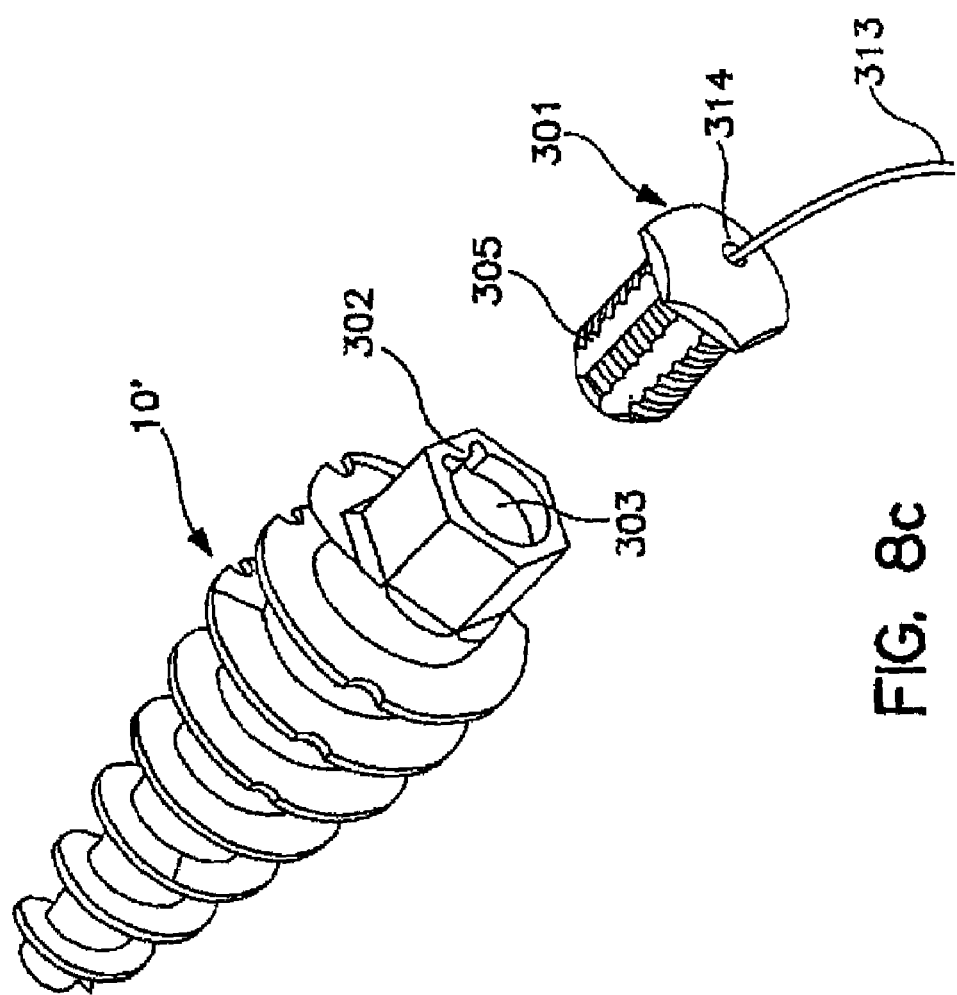
FIG. 8c is a perspective view of an exemplary fixation screw, proximal extension and cover, in one embodiment of the present invention.

One or more milled slots 13 run the length of the uniform diameter portion of the screw 10. Slots 13 ensure that as healing or tissue in-growth begins, migrational or rotational movement of the screw is inhibited. The screw 10 is configured to be driven by a female or socket type driver 2 as shown in FIG. 7*b*, which engages a hex-shaped drive 15 located toward the proximal end 17 of the screw. A cylindrical proximal extension 14 (which may, alternatively, be a recess 303 which mates with a plug or other protrusion on the implant surface, as shown in FIG. 8*c*) extends from hex-shaped drive 15, which eventually serves as a fixation element for surface prosthetic implant 40. Through hole 16 runs through the central axis of the screw. Hex-shaped cover 30 (which may, alternatively, be a plug 301, for mating with a fixation element 302 having a recess, as shown, e.g., in FIGS. 3*b*, 8*c*, and 9*c*, and described in the following paragraph) is configured to engage the cylindrical proximal extension 14 of the screw 10 to prevent exposure of the cylindrical extension from inadvertent contact or damage. The hex-shaped cover 30 is finished with a radiused proximal end 31 that assists in the visual determination of the correct depth setting of the screw. Through hole 32 in the hex-shaped cover 30 corresponds with through hole 16 in the fixation screw 10.

Figure 3B:
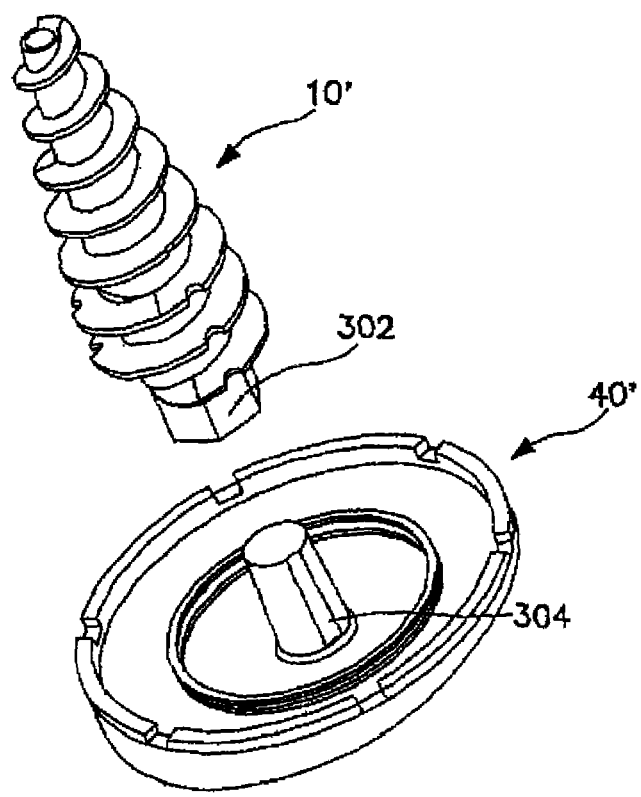
FIG. 3b is an exploded perspective view of another exemplary fixation screw and implant in one embodiment of the present invention.
Figure 9C:
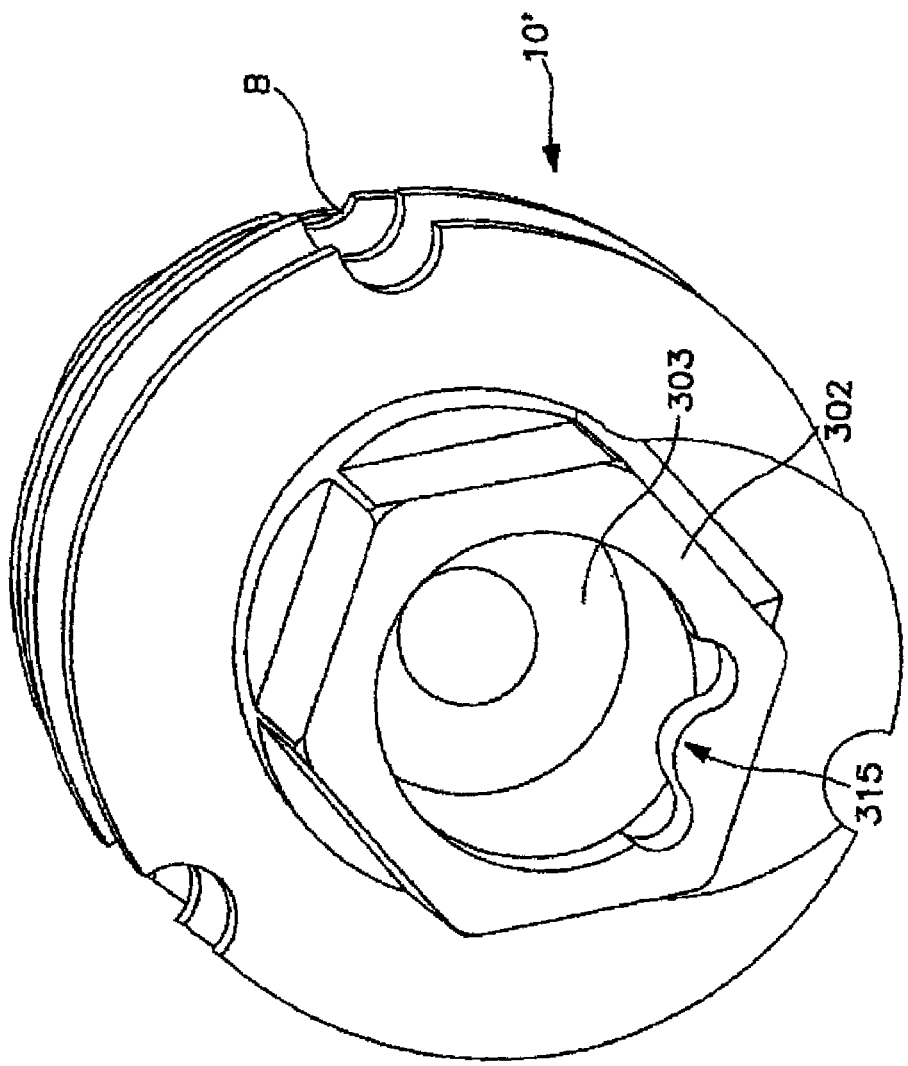
FIG. 9c is a perspective view of an exemplary fixation screw and proximal extension, with the cover removed, in one embodiment of the present invention.
Figure 1B:
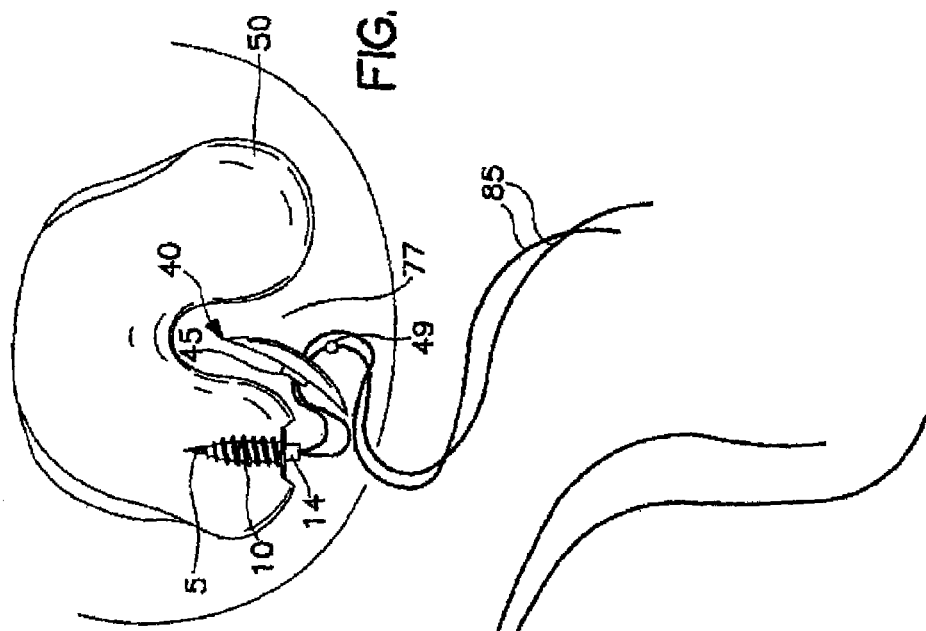
Figure 1A:
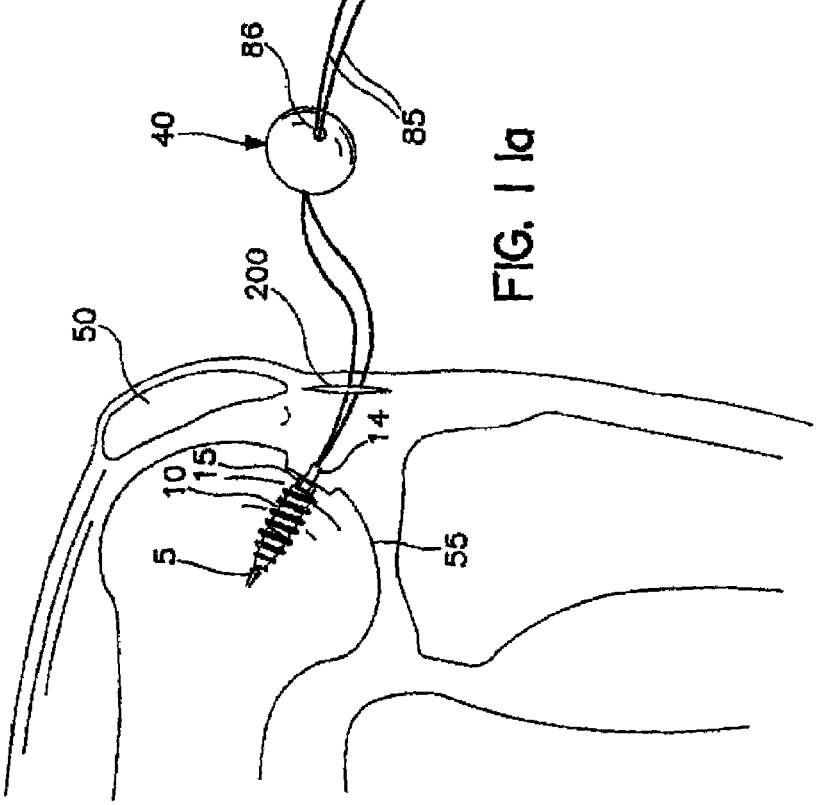

Alternatively, as shown in FIGS. 3*b*, 8*c*, and 9*c*, the female-shaped cover may instead be a plug 301 having a male-shaped mating component 305, for mating with a fixation element 302 of a screw 10' having a recess 303. Additionally, the shape of the cover and plug, or other recessed, protruding, or mating components may be other than hexagonal, and those in the art will recognize that one of any number of shapes or configurations for such components may be employed in a device or method consistent with the invention.

Also, while many of the components described herein are cannulated, having guide apertures, through holes, and/or central lumina along their length, for disposing such components about a guide rod for proper location of the components with respect to the articular surface, it should be recognized that a suture 313 or other flexible element, or other guide feature may be used in place of a guide rod, or a guide rod or wire may be eliminated altogether from one or more steps consistent with the invention described herein. As shown in FIG. 8*c*, the suture 313 may be fixedly or removably attached to the plug 301.

Figure 4A:
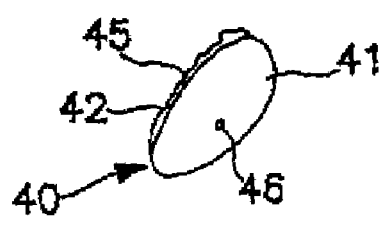
FIG. 4a is a perspective view of the upper surface of an exemplary implant in one embodiment of the present invention.
Figure 4B:
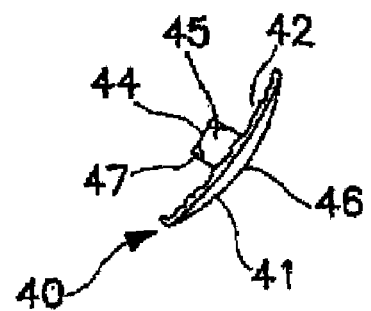
FIG. 4b is a side view of an exemplary implant in one embodiment of the present invention.
Figure 4C:
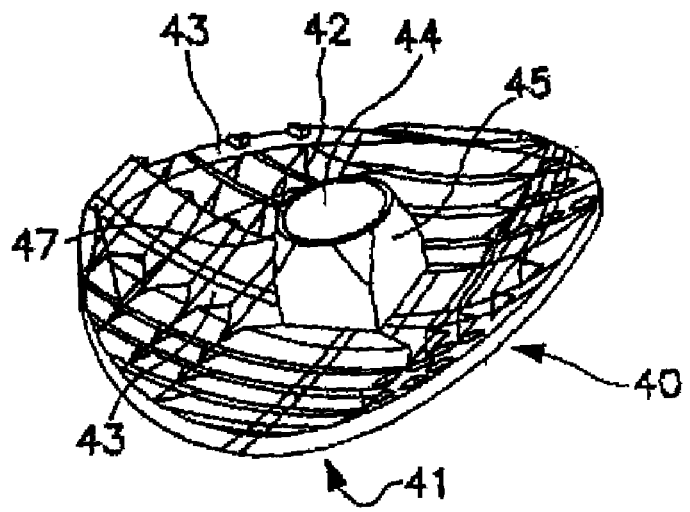
FIG. 4c is a perspective view of the lower surface of an exemplary implant in one embodiment of the present invention.

As shown in FIGS. 4*a*, 4*b* and 4*c*, implant 40 comprises lower bearing surface 41, top surface 42 and protrusion 45 located centrally on the bottom surface. As the top surface 42 of the implant 40 is not a bearing surface, and instead is fixed into subchondral bone 100, a series of stepped machine cuts 43 following the contours of the defect are created. By creating stepped machine cuts 43 a contoured contact surface matching the defect in the subchondral bone 100 is created. This contact surface results in an increased surface area that should enhance resistance to loosening of the implant 40 via rotational or translational loading. In the illustrated embodiment, the stepped cuts are shown as square cross-section cuts, but the cuts may be circular, triangular, or another configuration.

In order to secure the implant 40 to the fixation screw 10, precision taper 44 is machined into or onto a protrusion 45 on the top surface 42 of the implant. The precision taper 44 is configured to engage the cylindrical proximal extension 14 of the screw 10, once the hex-shaped cover 30 has been removed therefrom. Taper 44 may be mated with extension 14 so that a friction fit is provided between these surfaces. The assembled fixation device is shown in FIGS. 5a and 5b. Alternatively, other engagement mechanisms such as snap-fits, press-fits, threads, or coupling elements, for example, may also be used. In one embodiment, leading pin 47 arranged on the protrusion 45 assists penetration into subchondral bone. Also, in one embodiment, guide aperture 46 passes through the top 42 and bottom 41 surfaces of the implant 40, just slightly off center of the reference axis 20A. Alternatively, guide aperture 46 may be located in the center of the implant 40 and corresponds to through hole 16 running through the central lumen in the fixation screw 10. Bone cement may be injected through guide aperture 46 on the surface of the implant 40 and through hole 16 in the fixation screw 10, to enhance the contact surface between the device and the subchondral bone. In one embodiment, the implant is constructed of cobalt chromium, although other materials may be used, including implantable plastics. Additionally, biologically active coatings or surface treatments (e.g., to enhance bone ingrowth or improve wear properties) may be utilized or combined as laminates, particularly with respect to the bearing surfaces and bone contacting surfaces. Further exemplary materials that may be used in fabricating an implant consistent with the invention are described hereinbelow.

As shown in FIG. 3b, it is noted that precision taper 44 may be a male-shaped component 304 instead of the above-described female component 44. In this configuration, the male-shaped component 304 of the implant 40' is configured for mating with a fixation element 302 of the screw 10' having a recess 303 adapted to receive the male-shaped component 304.

By way of example, FIGS. 6a-13 depict one exemplary joint surface methodology of the present invention. FIG. 6a shows a focal defect 1 of the articular surface 55 of the femoral chondyle bone of the knee 50. This defect is identified by arthroscope 25 inserted in the area of the defect 1 during a diagnostic arthroscopy or surgical arthroscopy. The disclosed surgical intervention begins by drilling a guide pin 20 defining reference axis 20A into the central portion of the defect 1 via an incision 200 typical of arthroscopic procedures. Placement of this pin may be done using visual, freehand techniques, or may be located centrally by using outer element 71 of a measuring tool 70 (as shown in FIGS. 9a and 9b), or other aiming device or technique, to define a center. This reference axis 20A serves to establish a working axis located central to the defect 1 for the procedures that follow, and arthroscope 25 may be used to view the joint for purposes of establishing a reference axis 20A generally perpendicular to and bisecting the existing articular surface 55 defined by radii 60 and 61, as shown in FIG. 8b. Referring to FIG. 7a, 7b, 8a and 8b, fixation screw 10 and hex-shaped cover 30 are driven into the defect 1 in the subchondral bone 100 by socket-type driver 2 mounted over (i.e., about) guide pin 20 located on reference axis 20A. Under arthroscopic view, the depth of fixation screw 10 may be adjusted by driver 2 so that the bottom of the radiused surface 31 of the hex-shaped cover 30 is positioned tangent to the radii 60 and 61 that define the existing articular surface 55. The guide pin 20 is removed and the knee 50 is articulated through its range of motion to ensure that the height of the radiused surface 31 of the hex-shaped cover 30 is proper, since the prosthetic surface 41 of the implant 40 is created also to be tangent to this radiused surface 31. The depth positioning of the radiused surface 31 of the hex-shaped cover 30 establishes a point of origin or a reference point for all future measuring and machining operations. Arthroscopic examination may be carried out from multiple arthroscopic views to confirm positioning.

Figure 6B:
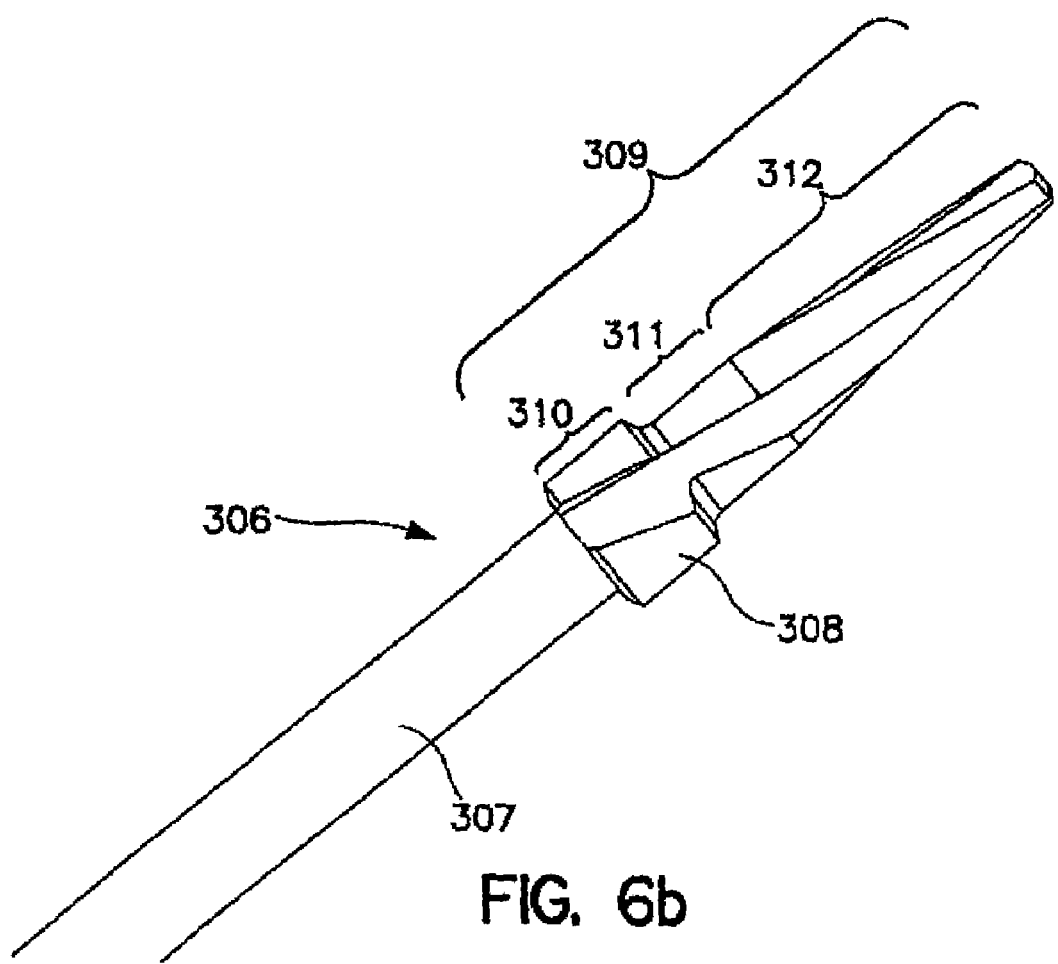
FIG. 6b is a side view of the distal tip of an exemplary drill device for boring a pilot hole to receive an exemplary fixation screw, in one embodiment of the present invention.

A drill mechanism 306, as illustrated in FIG. 6b, may be used to bore a pilot hole for receiving a fixation screw 10 (as shown, e.g., in FIGS. 2a, 2b and 3a). As shown, the drill may have a shank portion 307 and a bit portion 308. The bit portion 308 may include a spiral or parabolic fluted tip 309 having proximal 310, medial 311, and distal 312 portions. The root diameter at the medial portion 311 is substantially equal to the diameter of the fixation screw 10, and the diameter decreases as the distal portion 312 tapers away from the shank 307. The proximal portion 310 of the bit 308 may be used as a visual indicator during drilling, to determine the point at which the proper bore depth has been attained. The drill mechanism may have a central lumen (not shown) having a diameter slightly greater than the diameter of the guide pin 20 (as illustrated in FIG. 6a) running along its length, so that, with the guide pin 20 in place, the drill 306 may be disposed about the guide pin 20 during drilling to ensure proper location of the pilot hole with respect to the articular surface 55. Alternatively, a self-drilling or self-tapping screw, may be used, as those skilled in the art will recognize.

For surface preparation and accurate measurement of the implant site and the subsequent sizing of the implant, instrument 120 is provided. The compass instrument 120 may be configured to serve as a mounting tool for a number of functional blades or tips and when located about the axis 20A, via guide rod 20, may be used for measuring and cutting operations. In the embodiment shown in FIG. 15a, compass instrument 120 includes handle 110, a cannulated shaft 111 that extends through the handle, and a cannulated distal offset arm 112. The instrument may be rigid in construction and may be a durable reusable and resterilizable instrument. The distal offset arm 112 is configured so that it can be introduced into a site through an incision 200 typical of an arthroscopic procedure. Once the distal offset arm 112 has fully penetrated the incision and enters the site, shaft 111 can be angularly repositioned so that it becomes more coaxial to the reference axis 20A and advanced in-line with the reference axis 20A towards the implant target site. While performing this maneuver to position the compass instrument 120, the guide pin 20 should be removed from its position in the defect 1. When compass 120 is in its proper position at or near the implant target site, the guide pin 20 is delivered through the instrument cannulation 113, re-establishing the working (reference) axis 20A used to define the implant geometry.

Figures 15A, 15B:
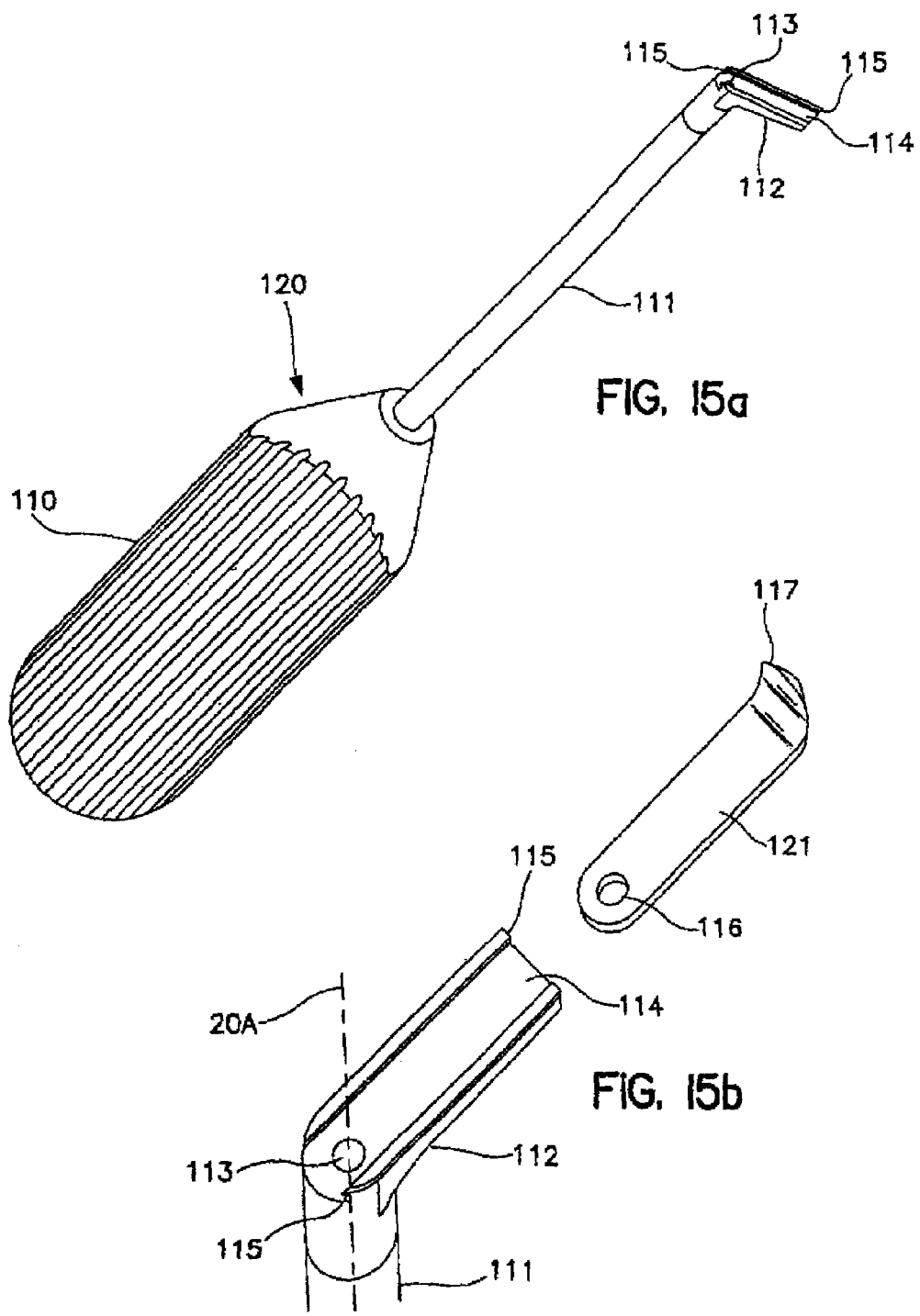
FIG. 15a is a perspective view of an exemplary compass instrument, in one embodiment of the present invention.
FIG. 15b is a perspective view of the distal offset arm of an exemplary compass instrument and cutting blade to be mounted thereon, in one embodiment of the present invention.

Referring to FIG. 15b, within offset arm 112 is a slotted surface 114 for engaging a series of cutting blades 121, boring blades 124, or measuring probes 122. The slots 115 are configured so that said series of cutting blades 121, boring blades 124 (FIG. 17c), measuring probes 122, 123 (FIGS. 17a, 17b), or like elements may be partially constrained or fixed in position such that they may be adjusted linearly along the length of the slotted surface 114 over a defined distance of travel. Intersecting the plane of travel defined by slotted surface 114 and slots 115, is the cannulation 113.

Figure 16:
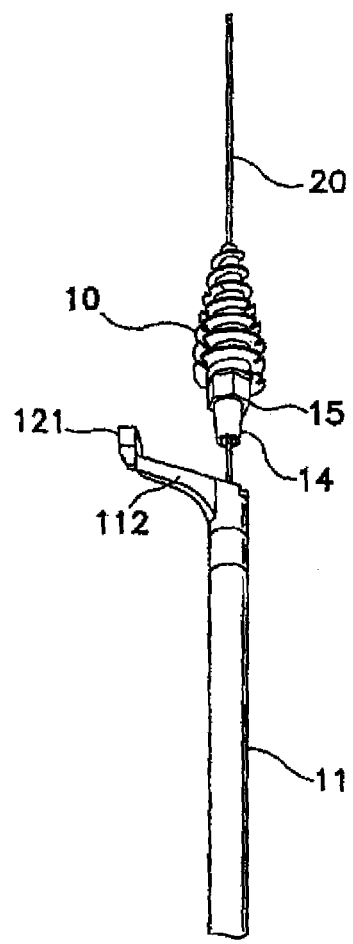
FIG. 16 is a perspective view of an exemplary compass instrument and cutting blade mounted on an exemplary guide pin, in one embodiment of the present invention.

As illustrated in FIG. 16, when fitted with a cutting blade 121, and with the guide pin 20 advanced through the shaft 113 of instrument 120, so that the guide pin passes through a closely sized hole 116 in the cutting blade, the blade's position becomes fully constrained. When constrained in this fashion, a fixed length from the rotational or reference axis 20A to the cutting surface 117 of cutting blade 121 is established. This defines the radius that is effected as the instrument 120 is rotated around the guide pin 20, and corresponds to the overall diameter of the implant 40 that is delivered to the fully prepared site. The cutting blade 121 is used to circumscribe and cleanly cut the surrounding articular cartilage.

Figure 17A:
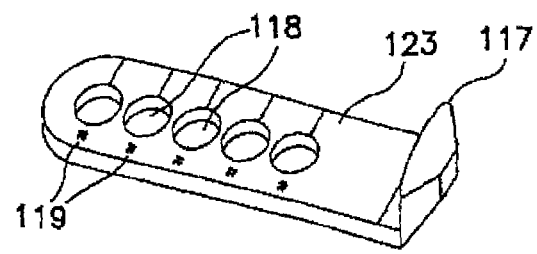
FIG. 17a is a perspective view of another exemplary cutting blade, in one embodiment of the present invention.
Figure 17B:
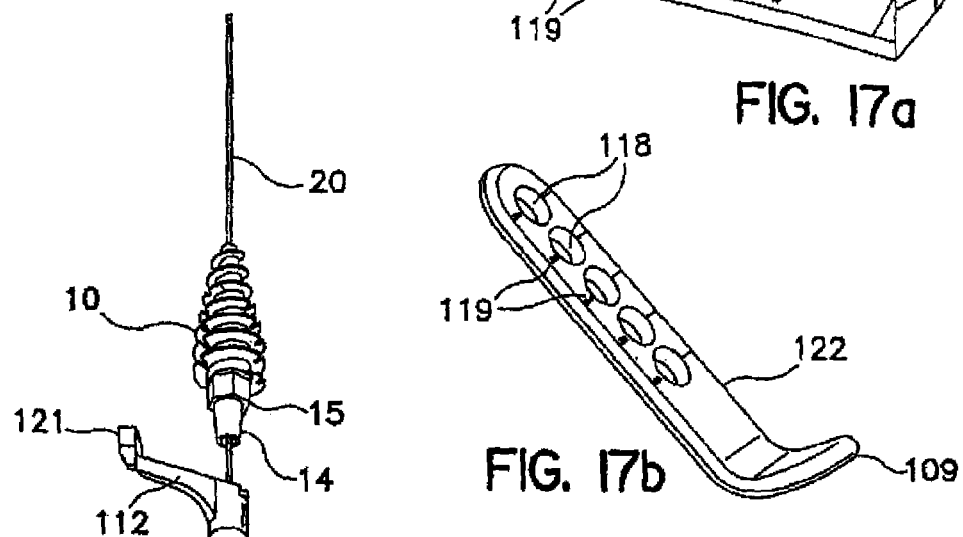
FIG. 17b is a perspective view of an exemplary measuring probe, in one embodiment of the present invention.
Figure 17C:
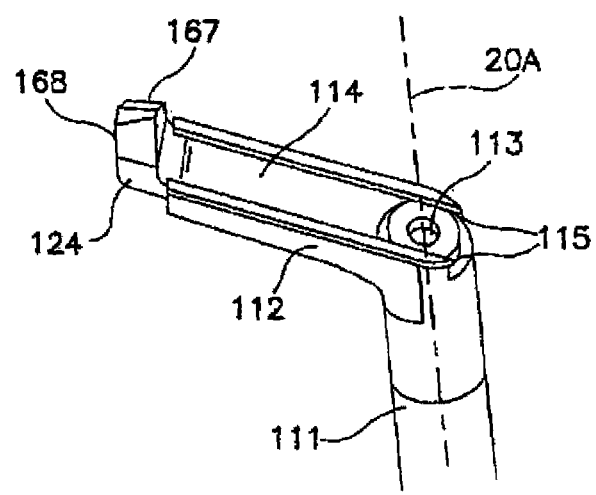
FIG. 17c is a perspective view of an exemplary multi-faced blade mounted in the distal offset arm of an exemplary compass instrument, in one embodiment of the present invention.

In an alternative embodiment, as shown in FIGS. 17a and 17b, blade 123 and measuring probe 122, respectively, may have multiple holes 118 that defines that probe/blade's functional diameter. In addition, the blades may be specifically configured so that staged or sequential cuts of varying depths and diameters can be performed within the procedure. Also, such a blade can be configured by providing a readable scale 119 corresponding to the hole 118 pattern, so that the surgeon may determine and set the appropriate diameter as needed by positioning the guide pin 20 in the corresponding hole. As the readable scale 119 may be located on the blade 123 with respect to the blade's cutting surface 117, a high degree of positional accuracy may be achieved as the scale may be defined specifically for each type of blade. This approach creates an inexpensive means of providing sharp blades of varying diameters and varying blade types without a large inventory of size- and type-specific blades. Referring to FIG. 17b, rounded tip 109 of measuring probe 122 can be used to determine the appropriate diameter and can be similarly sized and secured in the compass instrument 120. The tip 109 may be rounded to prevent marring of the articular surface. FIG. 17c shows a boring bit or bone cutting blade 124 with multiple cutting surfaces 107 and 108 configured in this fashion.

Turning now to FIGS. 9a and 9b, with the guide pin 20 replaced, a measuring tool 70 is inserted so that the reference axis 20A is utilized. A central element of the measuring tool 70 is a post 75 that is static, establishes the axial location of the point of origin 80, and mates with a rotational location feature within the screw 14. By rotating the outer arm or outrigger 71 of the measuring tool 70 relative to the static post 75 while also maintaining contact with the articular surface 55, an axial displacement or Z dimension can be established relative to the point of origin 80 for any point along the sweep of the outrigger. Each such Z dimension may be recorded in real time with conventional dial gauge indicators 72 or with a digital recording device, such as disclosed in U.S. Pat. No. 5,771,310 to Vannah, or by using other known marking techniques. Although numerous points may be taken, ideally a minimum number of points are taken to define accurately the target articular surface. In other embodiments, multiple outriggers that embody different diameters or an adjustable outrigger may be used to map larger defects, and also to determine the final diameter of the prosthetic surface that fits within the defect. It is noted that the measuring tool may comprise a spring or other tensioning device (not shown), for urging the outrigger distally with respect to the handle of the tool. In this aspect, the outrigger is manually pressed against the articular cartilage, so as to maximally compress the articular cartilage upon recording data points, so that the data points taken are of a maximally "loaded" or "compressed" dimension.

Figure 20A:
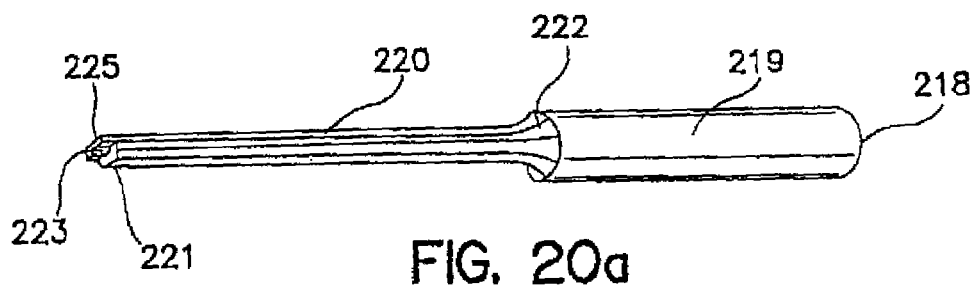
FIG. 20*a* is a perspective view of an exemplary inner recording element of an exemplary measuring device, in one embodiment of the present invention.
Figure 20B:
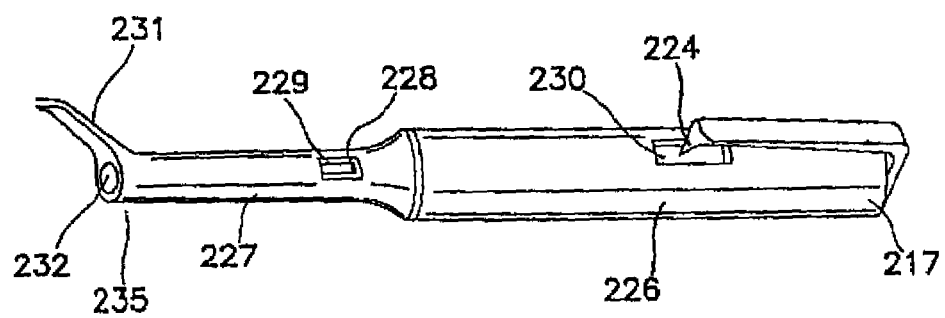
FIG. 20*b* is a perspective view of an exemplary outer marking element of an exemplary measuring device, in one embodiment of the present invention.
Figure 20C:
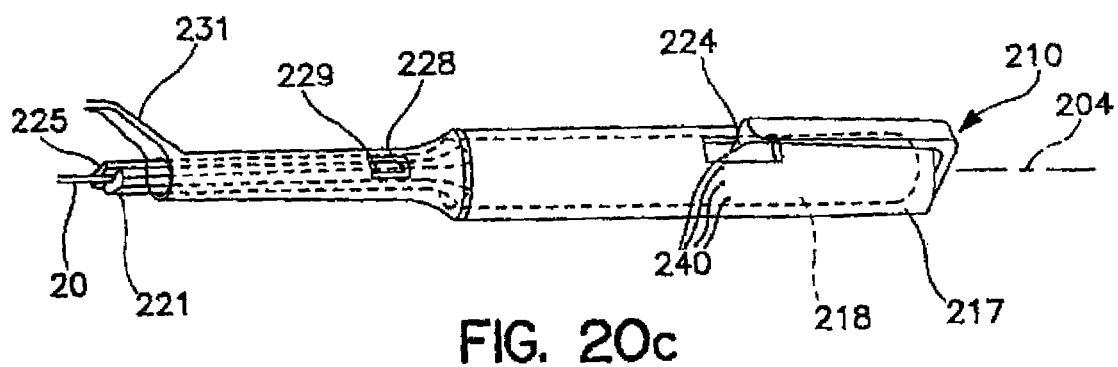
FIG. 20*c* is a cross-sectional perspective view of an exemplary measuring device showing an exemplary inner recording element and an exemplary outer marking element, in one embodiment of the present invention.
Figure 20D:
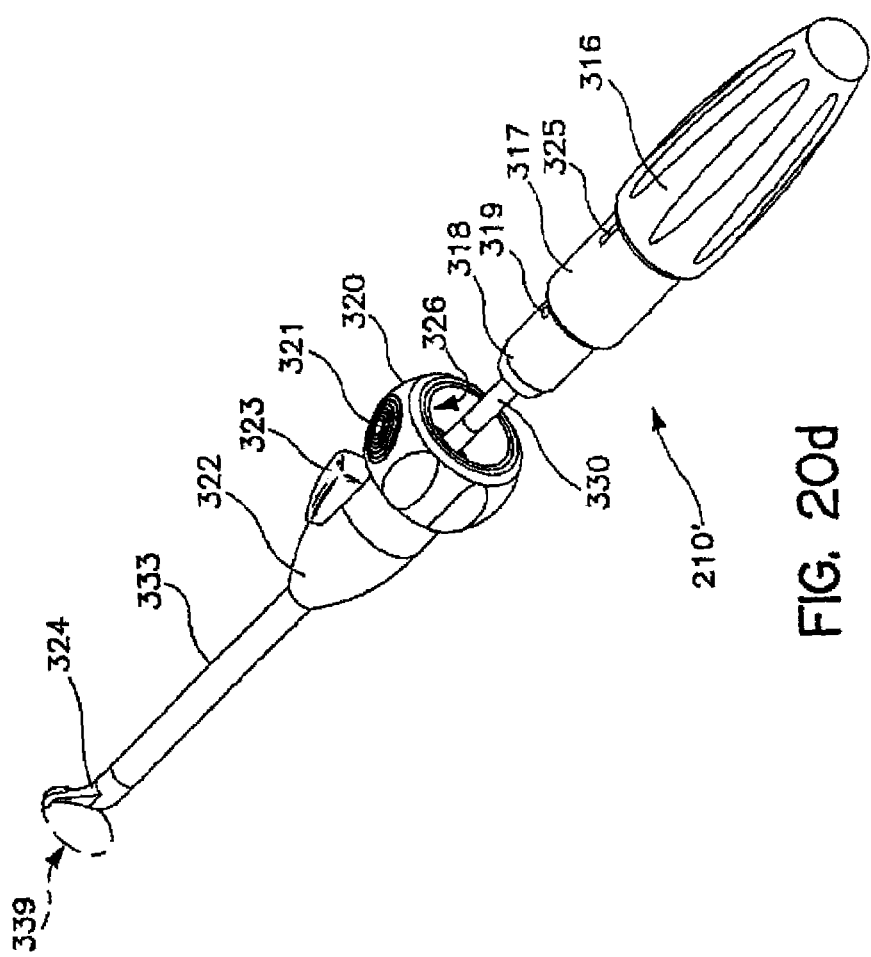
FIG. 20*d* is an exploded perspective view of another exemplary measuring device, in one embodiment of the present invention.

FIGS. 20a, 20b and 20c show an alternative measuring and mapping device 210 for obtaining the articular surface dimension, comprising housing 217 and a recording element 218. As shown in FIG. 20a, recording element 218 includes upper portion 219, flange 222 and calibrated lower portion 220. Key-shaped surface 221 located at distal end 225 of recording element 218 is configured to engage a reciprocal key-shaped surface in the proximal extension 14 of fixation screw 10, or, for example, a key shaped cover arranged on the proximal end of the screw (not shown). The upper portion 219 of recording element 218 may be constructed of a relatively soft or other deformable material that can be marked with patient data. Cannulated shaft 223 runs through the central lumen of the recording element 218. As shown in FIG. 20b, housing 217 includes a marking mechanism 224 located on the upper portion 226 of the housing, at or within window or aperture 230. An indexing indicator 228 is located on the lower portion 227 of the housing 217, at window or opening 229.

Turning to FIG. 20c, recording element 218 is inserted in housing 217 of measuring and mapping device 210, so that the distal end 225 of recording element 218 appears through opening 232. Tensioning means (not shown) in the device 210, enables recording element 218 to move longitudinally within housing 218. With the guide pin 20 replaced, the measuring device 210 is inserted on the guide pin on reference axis 20A so that key-shaped surface 221 engages the corresponding keyed surface of the screw and is maintained in static position thereby. These key-shaped surfaces establish the rotational position of the articular surface points to be mapped relative to the screw. During the measuring and mapping procedure, the surgeon rotates housing 217 and outer arm or outrigger 231 located at the distal end 235 of housing. By depressing marking mechanism 224, a series of depressions or marked points 240 is established in the relatively soft surface of the upper portion 219 of the recording element 218, which deforms at these marked points so that they can be utilized as patient data. Indexing indicator 228 and calibrated lower portion 220 of recording element 217 allow for controlled rotational movement between housing 217 and recording element 218. In this way, the rotational position of the mapped articular surface points 235 relative to the screw 10 as appreciated by outer arm of outrigger 231, is translated to the implant geometry as a feature so that the accurate rotational location of the implant 40 relative to the screw 10 is maintained.

For example, as shown in FIGS. 8b and 9b, to accurately reproduce the two radii 60 and 61 that locally define the articular surface 55, four points, 81a and 81b, and 82a and 82b, and the point of origin 80 are recorded. As any three points in a single plane define a curve, by recording points 81a and 81b and the point of origin 80, radius 60 defining the medial-lateral aspect 68 of the chondyle can be determined. By recording points 82a and 82b and the point of origin 80, the radius 61 defining the anterior-posterior aspect 69 of the chondyle can be determined. In the example provided, in order to maintain the relationship between these two defined radii, 60 and 61, the measuring tool 70 is constructed so that it can be accurately indexed from a fixed starting point along 90 degree intervals to capture or map said four points 81a, 81b, 82a and 82b, over the course of its revolution.

Locating surfaces or features created on the radius cover 30, or along some length of the fixation screw 10, hex-shaped drive surface of the screw 14 or on the cylindrical proximal extension (or recess) of the screw 14, correlate to some surface or feature on the measuring tool 70 and allow the measurement of the rotational position of the four measured points 81a, 81b, 82 and 82b, about the reference axis 20A with respect to said locating surfaces. This data becomes important in configuring the implant 40 with respect to the fixation screw 10 so that the proper orientation of said measured points to fabricated geometry is maintained. Of course, such measuring tool can be configured to measure any number of points at any interval desired.

While the measurements are illustrated in FIGS. 9a and 9b as being taken from the bottom of the radiused surface 31 of the hex-shaped cover 30 of the screw, the measurements may alternatively be taken from the top of the screw 10' itself, as shown in FIG. 9c. As shown, in this embodiment, a key 315 or other alignment feature may be provided, to indicate the starting point for taking measurements. In this configuration, the measuring tool used, as well as the implant manufactured, both have a mating feature matching the key 315, for properly locating the starting point of the measurements taken and thereby subsequently properly aligning the implant with respect to the defect.

Other embodiments of measuring and recording tools are possible. One such embodiment of a measuring and recording tool 210' is shown in FIGS. 20d-20i. As shown, measuring tool 210' comprises a handle 316, outer shaft 333, inner shaft 330, scroll 317, a tactile feedback portion 318, ring 320 having a button 321 in communication with a sharp marking point 326 thereunder, a rotating portion 322 having a rotational lock 323 which prevents rotation of the rotating portion 322 when engaged, and an outrigger portion 324. The handle 316 remains fixed during rotation and does not move while the tool 210' is used for measuring. Instead, the rotating portion 322 is rotated to a start position and the rotational lock is engaged, securing the rotating portion 322 to the tactile feedback portion 318 and thereby preventing its rotation. The scroll 317 is configured with a notch 325 or similar mating feature to align with a corresponding mating feature (not shown) of the handle 316, such that the scroll can only align at one rotational point, at 0 degrees, with respect to the handle 316 upon loading into the tool 210', e.g., by "snapping" into place. The sharp marking point 326 located inside the ring 320 under the sharp marking point 326, marks a point of depression into the scroll 317 while first button 321 is being depressed. Instead of marking by making depressions on a scroll or spool, marking could alternatively be made upon nearly any surface, e.g., using ink to record on a paper spool, or by digital means.

Figure 20E:
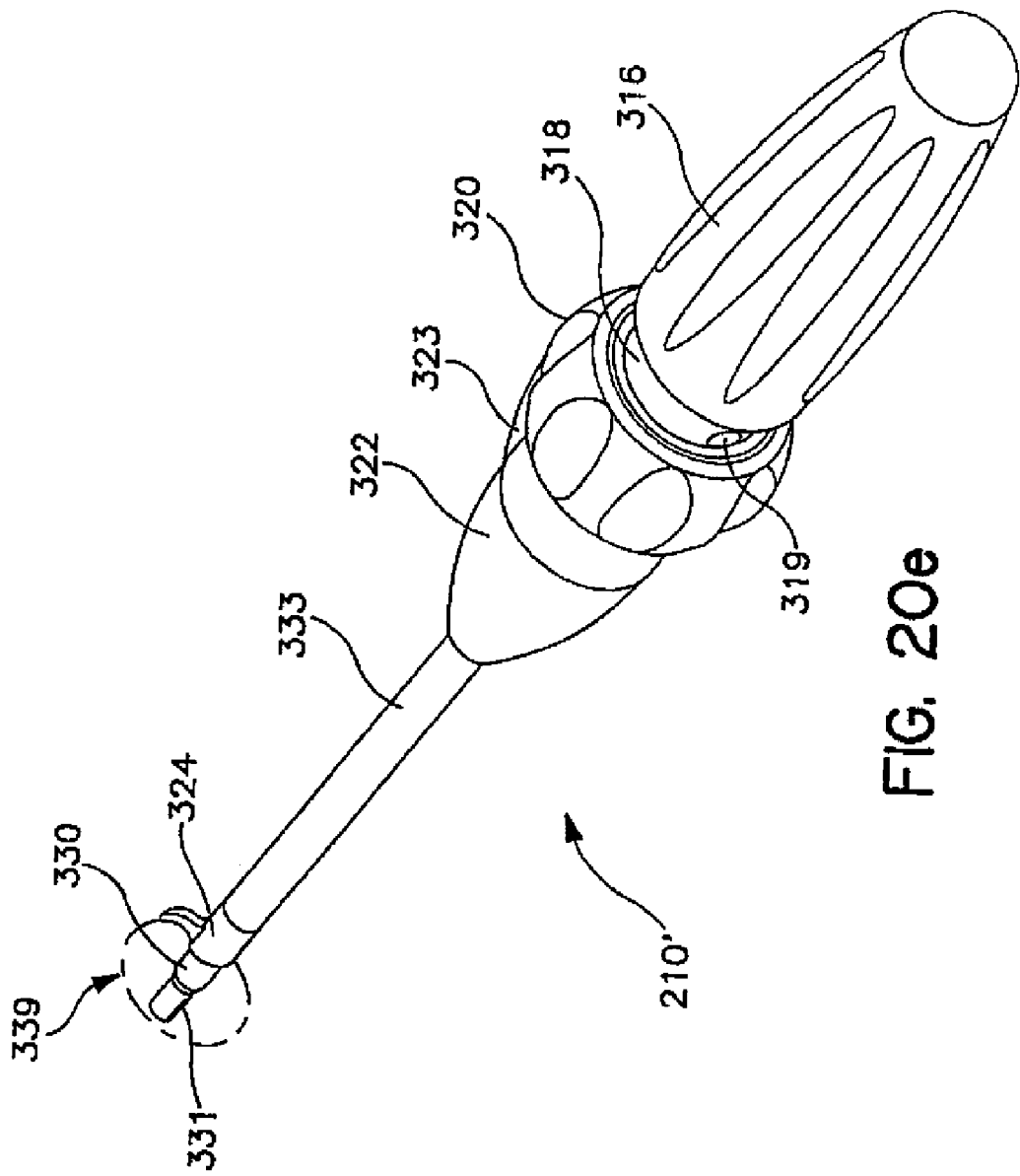
FIG. 20*e* is a perspective view of the exemplary measuring device of FIG. 20*d*, illustrating an exemplary scroll alignment feature, in one embodiment of the present invention.
Figure 20F:
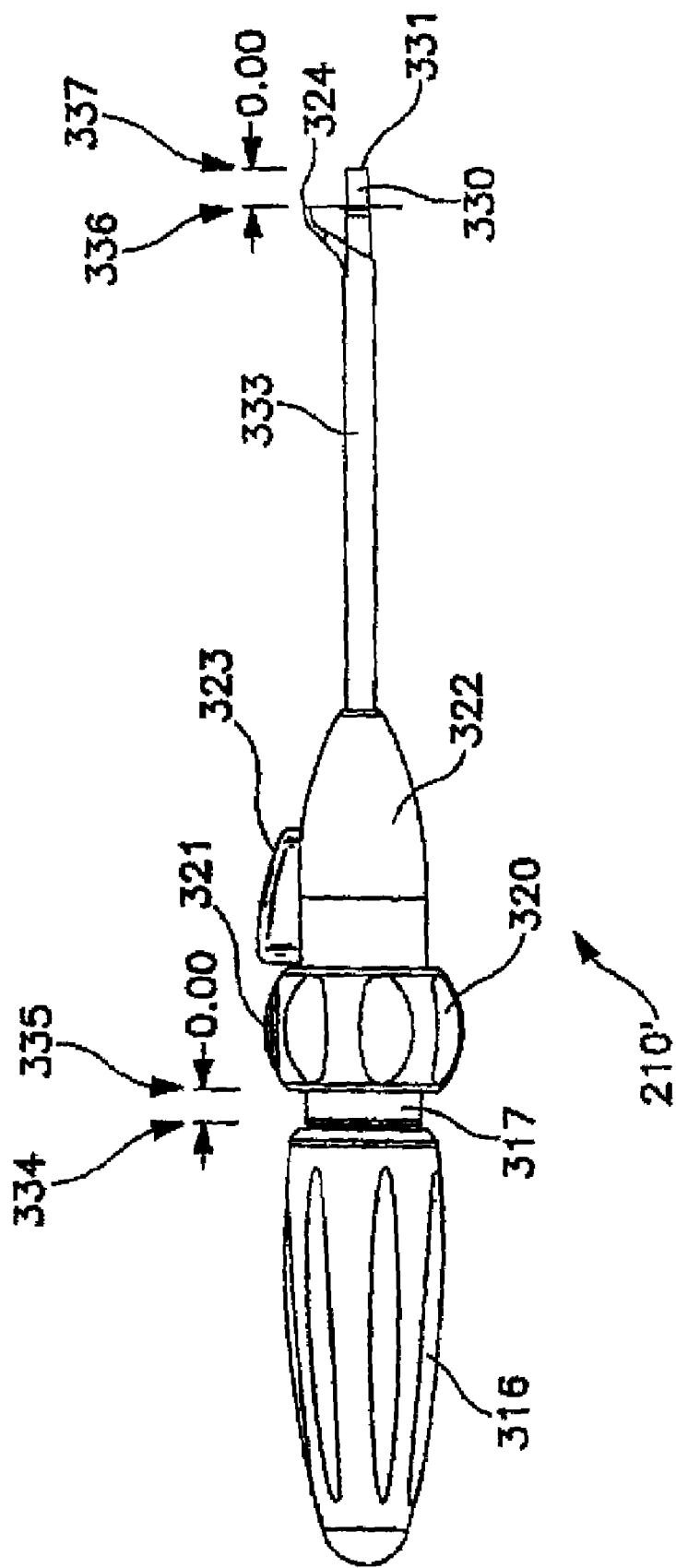
FIGS. 20*f* and 20*g* are side views of the exemplary measuring device of FIG. 20*d* illustrating the translational motion of the handle with respect to the tip of the device, in one embodiment of the present invention.
Figure 20G:
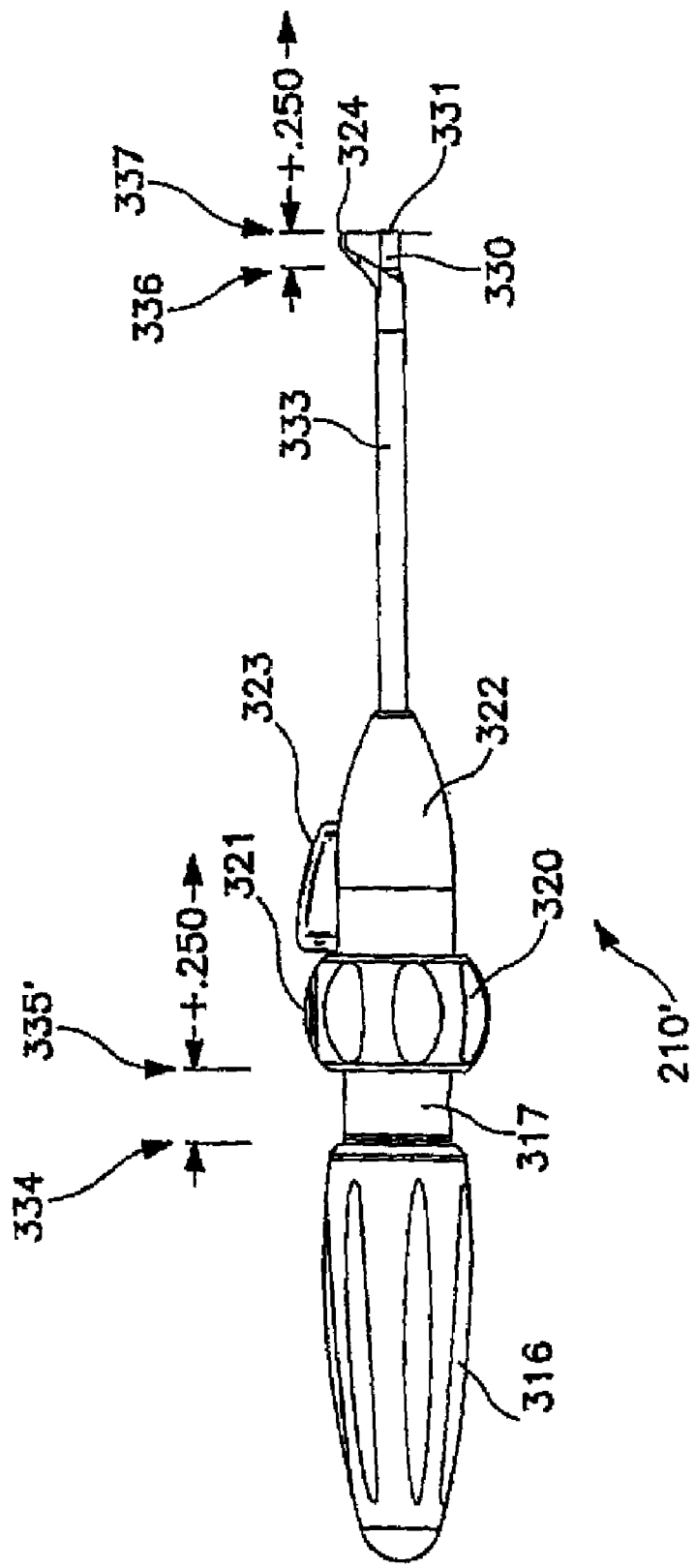

As shown in FIGS. 20f and 20g, outer shaft 333, which is fixedly coupled to rotating portion 322, outrigger 324 and ring 320, is freely rotatably disposed about inner shaft 330 and slidably disposed about inner shaft 330 within a range bounded by points 334 and 337. In FIG. 20f, the outrigger 324 is retracted, and outer shaft 333 is located at a position of origin along a z-axis parallel to the inner 330 and outer 333 shafts, such that the proximal end of the ring 320 is located at position 335. In FIG. 20g, the outrigger 324 is extended, and outer shaft 333 is located at a position 0.250 in. (0.64 cm.) from the origin of the z-axis parallel to the inner 330 and outer 333 shafts, such that the proximal end of the ring 320 is located at position 335'. The motion of the sliding of the outer shaft 333 about inner shaft 330 during marking is translated via the outer shaft 333, rotating portion 322 and ring 320 (including marking button 321 and marking point 326) to a location along the scroll 317. Thus, as the user rotates outrigger 324 by rotation of rotating portion 322, the outrigger moves along the articular surface proximally or distally with respect to the inner shaft, and the displacement of the outrigger 324 along a z-axis parallel to the inner 330 and outer 333 shafts may be marked on the scroll 317 by depression of the button 323 at various points along the rotation of the outrigger 324. The tactile feedback portion 318 has a series of depressions 319 or other tactile feedback means, e.g. spring ball plungers which engage in indentations (not shown) in the inner shaft 330, spaced at 90 degrees from one another, so that when the rotational lock 323 is engaged as rotating portion 322 is being rotated, the user feels a "click" or other tactile feedback to indicate to the user the rotational location of the rotating portion 322 at 90 degree intervals with respect to the handle 316, i.e., at 90 degrees, 180 degrees, 270 degrees, and 0 (or 360) degrees, for purposes of marking at those points. It is further noted that the starting point for marking may or may not be selected independent of the 90-degree rotational points, and that the rotating portion 322 may or may not be configured so that it is not tied to the 90-degree indexing until the scroll lock 323 is engaged.

Figure 20H:
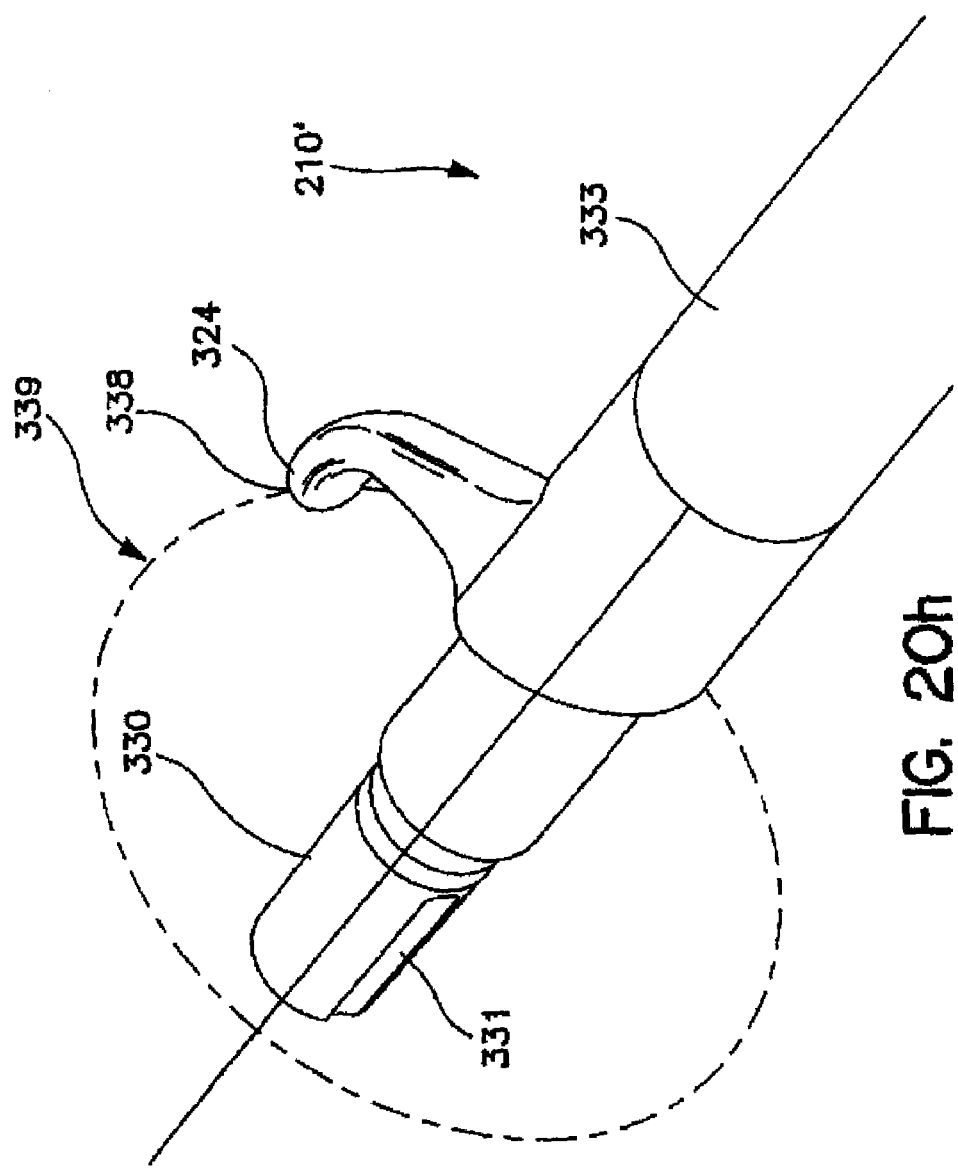
FIG. 20*h* is a perspective view of the distal end of the exemplary measuring device of FIG. 20*d*, in one embodiment of the present invention.
Figure 20I:
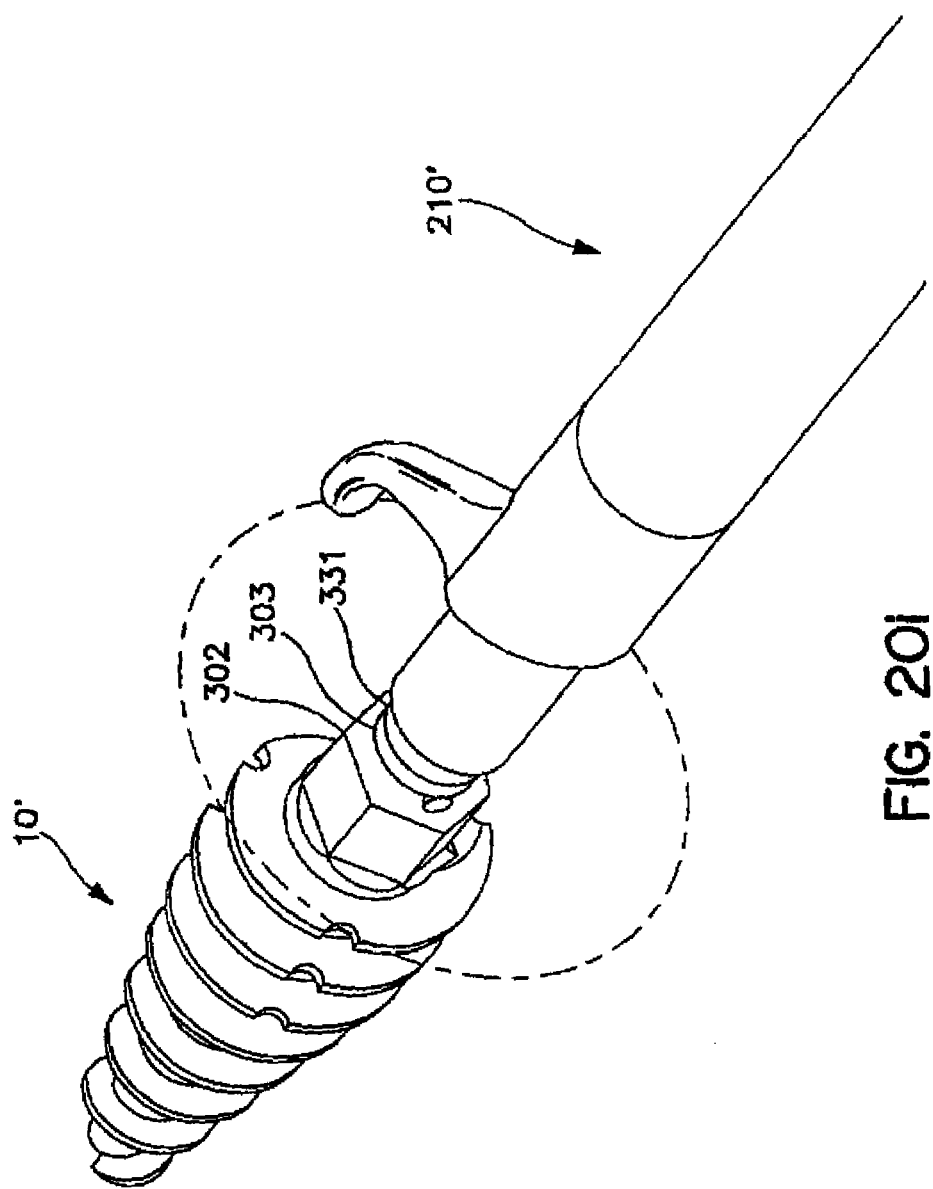
FIG. 20*i* is a perspective view of the distal end of the exemplary measuring device of FIG. 20*d* with outer element, disposed upon the inner element engaging a mating feature of the screw, in one embodiment of the present invention.

As shown in FIGS. 20e, 20h and 20i, a keyed mating feature 331 may be disposed at the distal end of the inner shaft 330 with respect to the outrigger portion, for mating with a key feature 315 on the screw 10' (as shown in FIGS. 9c and 20i), so as to locate properly the starting point of the measurements taken with respect to the screw, and the scroll 317. FIG. 20h illustrates a more detailed view of the distal end of the marking tool 210', with outer shaft 333, inner shaft 330 with keyed mating feature 331, and outrigger 324 with rounded end 338, which travels along the path of circle 339. FIG. 20i illustrates the measuring tool 210', with the keyed mating feature 331 inserted into the recessed portion 303 of the screw 10' at its fixation element 302.

Referring now to FIG. 14a, data recorded during the mapping procedure described above can then be entered into a known parametric engineering design software or similar algorithm, as four values, 85a, 85b, 85c, and 85d, corresponding to the four measured points, 81a, 81b, 82a and 82b, with the origin 80 defining a reference plane. These four values 85a, 85b, 85c and 85d, are represented by line elements that are geometrically constrained to lie upon a circle 90, which represents the diameter of the measuring tool 70. These line elements are also constrained to lie within planes that are perpendicular to one another. Of course, more than four points may be taken and used to map the articular surface, e.g., 8 points; however, a minimum of four points should be taken, so that two intersecting datum curves may be defined for purposes of mapping.

Datum curves 86 and 87, representing the medial-lateral ("ML") and anterior-posterior ("AP") curves, are constructed by connecting the end points of the line elements 81a and 81b, and 82a and 82b and the point of origin 80, which is common to both curves. These two datum curves 86 and 87 can be used to construct the articular or bottom surface 41 of the prosthetic implant 40. By sweeping datum curve 87 along a path defined by datum curve 86, a three dimensional surface is now defined.

By constructing this series of geometric relationships in a known parametric engineering model, patient-specific geometry can be input as values and the model algorithm can be run to reproduce the anatomic contours mapped in the patients within only a few moments. As a process, this generic model is the starting point for all patient treatments. Sterile pins, screws, and measuring devices that are all non-patient-specific may be stocked in the hospital and ready to use whenever an appropriate defect is diagnosed. Patient-specific data may be transmitted from the surgeon to the fabricating facility via an interface to the Internet or other network. Data input into the interface may be read directly into the generic parametric model to produce a viewable and even mappable patient-specific parametric model within moments. Confirmation by the surgeon could initiate a work order for the production of the patient specific device. Existing technology allows the parametric model to generate toolpaths and programming, e.g., to a CAD/CAM system comprising appropriate hardware and/or software coupled to appropriate data-driven tools, to fabricate the implant.

Defining two additional datum curves 88 and 89, at offset distances from datum curves 86 and 87, is performed to define the top or non-bearing surface 42 of the implant 40. This top surface 42 should be closely matched to the bearing surface geometry to be implanted without having to remove an excessive quantity of bone from the chondral surface.

Figure 19D:
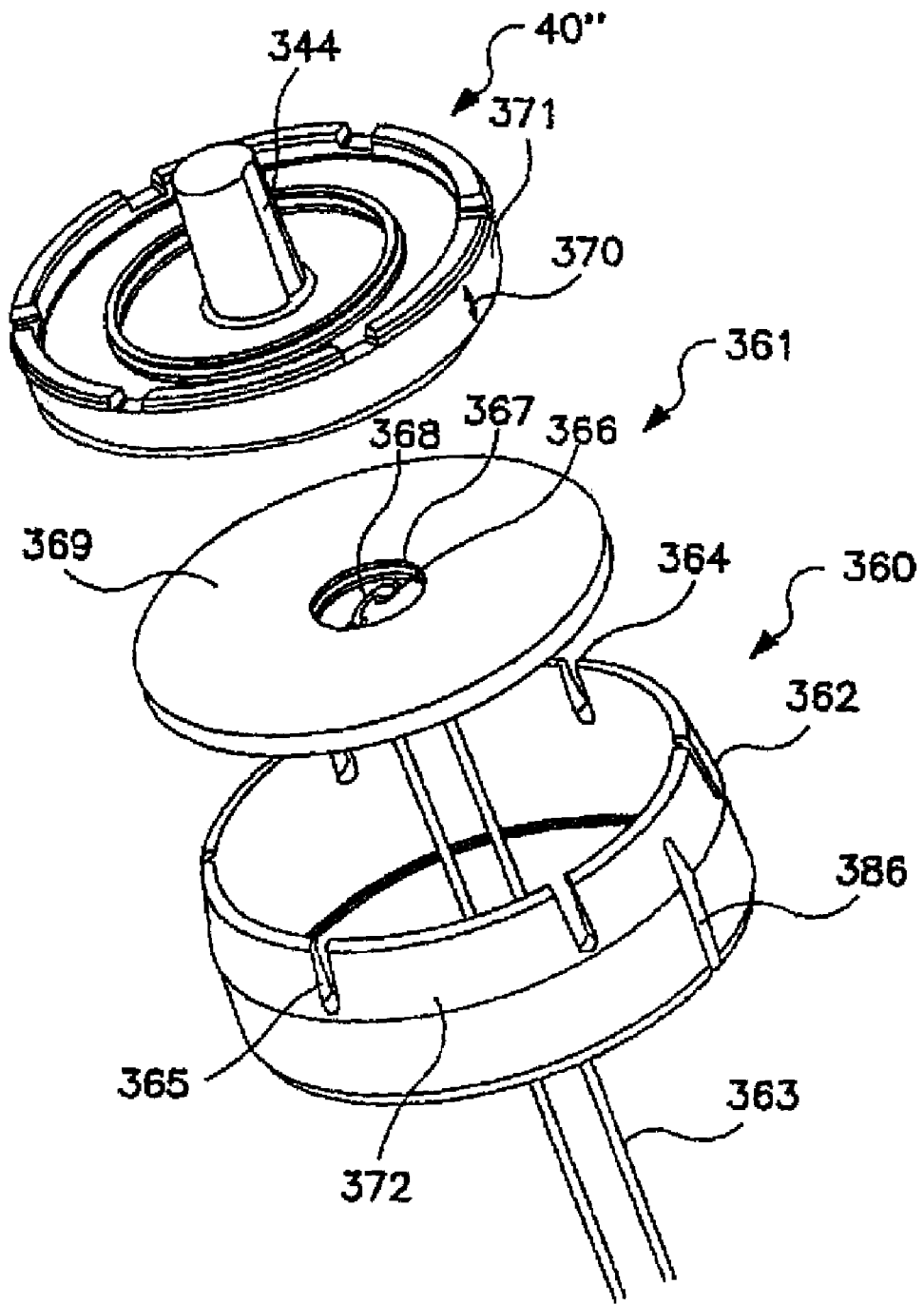
FIG. 19d is an exploded perspective view of another exemplary implant with taper lock ring, washer and suture, in one embodiment of the present invention.

Referring to FIGS. 14c and 19c, implant geometry may be defined whereby the top or bone contacting surface 42 of the implant 40 exhibits an axial symmetry. The central axis AA passes through the point of origin 80 of the implant 40 and when the implant is positioned at the target site, aligns with the original reference axis 20A as defined by the guide pin 20 and fixation screw 10. The central axis AA can then be used to define the preparation tools so that the bone contacting surfaces 42 of the implant 40 and the preparation tools can be matched in both configuration and dimension to create a mating fit between the surface of the prepared target site and the bone contacting surfaces 42 of the implant. For example, if the preparation tools can be fabricated using some of the same dimensions obtained during the articular surface mapping procedure, the implant geometry and corresponding preparation tool geometry can be mated and optimized so that a minimum vertical thickness of the implant as well as a minimum depth of bone removal is required. This may be advantageous in ensuring good long term clinical results with the implant, as poor quality of fit between bone surfaces and bone-contacting surfaces of traditional orthopedic prosthetic devices has been noted to contribute to early clinical failures.

For example, as shown in FIGS. 14c and 19c the top or bone contacting surface 42 of the implant 40, a series of radial cuts 198 may create surfaces that increase resistance of the implant to rotational forces. These features may be located at the outer diameter 190 of the implant 40 to increase their effectiveness. Additional contact surfaces may also be created by one or more protrusions 195 located on the bottom 42 of the implant. Similarly, surface treatments known in the field of orthopedic devices, such as porous and/or osteoconductive coatings, may be utilized on surface 42.

As shown in FIG. 19b, outer diameter 190 may include a slight outward taper or protrusion 197 along the diametrical surface to enhance load bearing or load transfer properties of the implant to surrounding bone. This feature may also increase the fixation strength of the implant. A fillet 199 (as shown in FIG. 19a) that runs around the implant at the intersection of the diametrical surface 190 and the bearing surface 41 is also useful in providing a smooth transition between the host articular cartilage and the implant surface.

However, if a greater depth of implant is needed as a result of the defect appearance the offset curves 88 and 89 (as shown in FIG. 14a) can be extended to increase the overall thickness of the implant 40 or the offset curves may be eliminated entirely so that the contoured surface is backed by a revolved geometry that is symmetrical to reference axis 20A. Turning to FIG. 19c, where the ML curve and AP curve (defined by the obtained measurements) are not axially symmetrical, the thickness of the implant 40 requires adjustment. At the same time, an unnecessarily thick implant requires a greater amount of bone to be removed at the target site. Therefore, the thickness of the implant may be determined by taking the largest obtained measurement and adding a minimal offset amount 208. (The implant is thinnest at the highest point on the ML curve.) This can be similarly accomplished by adjusting the angle Δ (FIG. 19a) of the bone-contacting surface 42 of the implant 40 and a corresponding angle of the preparation tool. This also allows for a correction of the implant geometry, to compensate for any non-perpendicular placement of the guide pin with respect to the articular surface.

Figure 25:
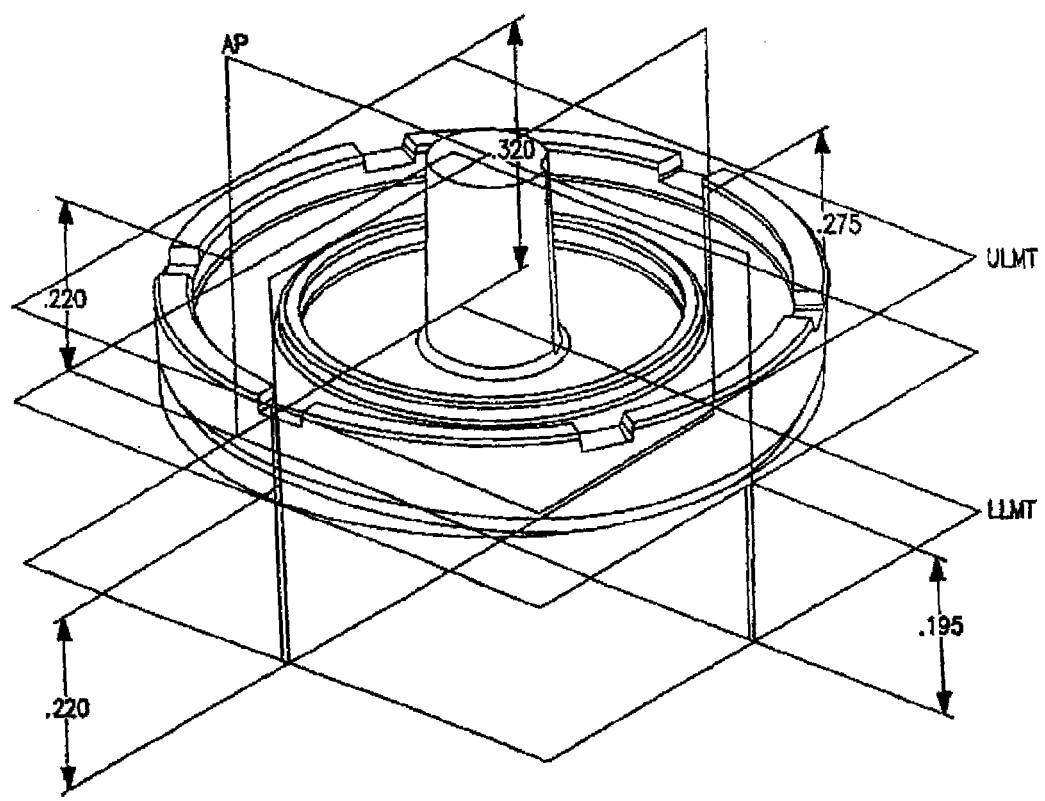
FIG. 25 is a perspective view of an exemplary implant illustrating the geometry of said implant for use in an algorithm for establishing minimum implant thickness, in one embodiment of the invention.
Figure 26:
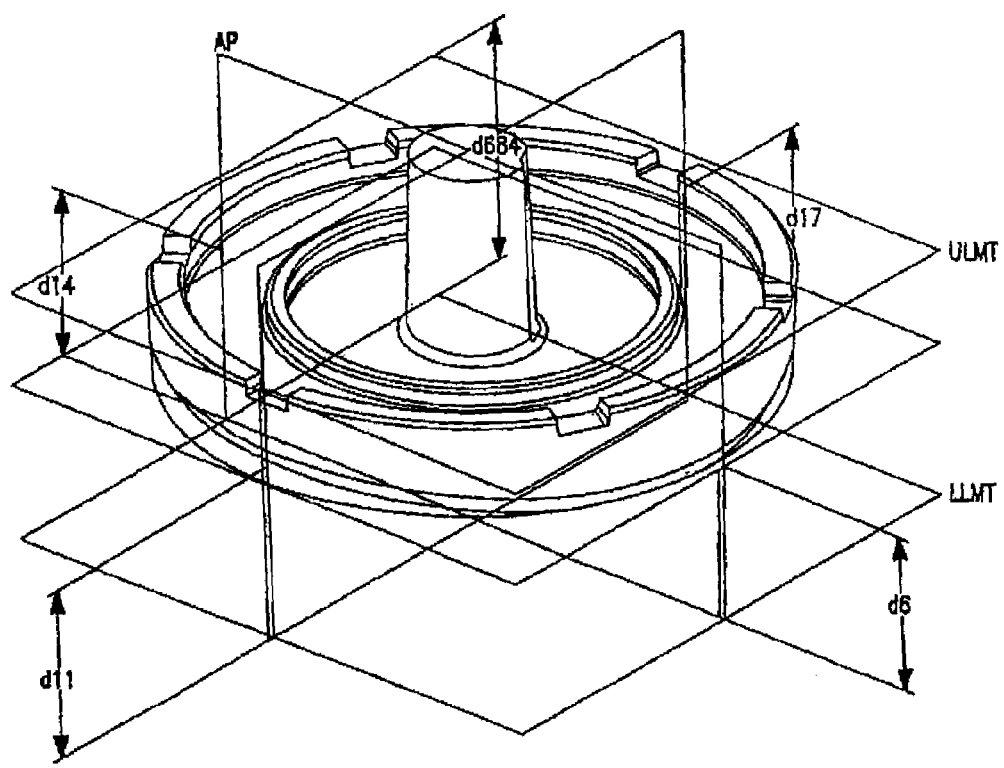
FIG. 26 is a perspective view of an exemplary implant illustrating the geometry of said implant for use in an algorithm for establishing minimum implant thickness, in one embodiment of the invention.

With reference now to FIGS. 25 and 26, an exemplary algorithm consistent with the invention establishes the minimum thickness of an implant necessary to include all patient data points, receiving as input all of the points measured (typically, four) and identifying the largest value. One such exemplary algorithm is as follows (and as shown in FIGS. 25 and 26):

```
maxval= D6
if maxval < D11
    maxval = D11
endif
if maxval < D14
maxval = D14
endif
D684 = maxval + .045
```

In the foregoing exemplary algorithm, a first data point D6 is initially assigned as the maximum value (maxval). If . . . then type statements are used to compare other data points (D11 and D14) to maxval. If other data points are greater than maxval, the algorithm reassigns maxval to the new larger data point. LLMT represents the height of the lower limit plane along the z-axis, and ULMT represents the height of the upper limit plane along the z-axis. D684 is a dimension that controls the ULMT plane, which is established in the model as the upper surface of the implant. ULMT is positioned as maxval plus an additional arbitrary and/or fixed material offset (0.045 in this case).

Figure 5C:
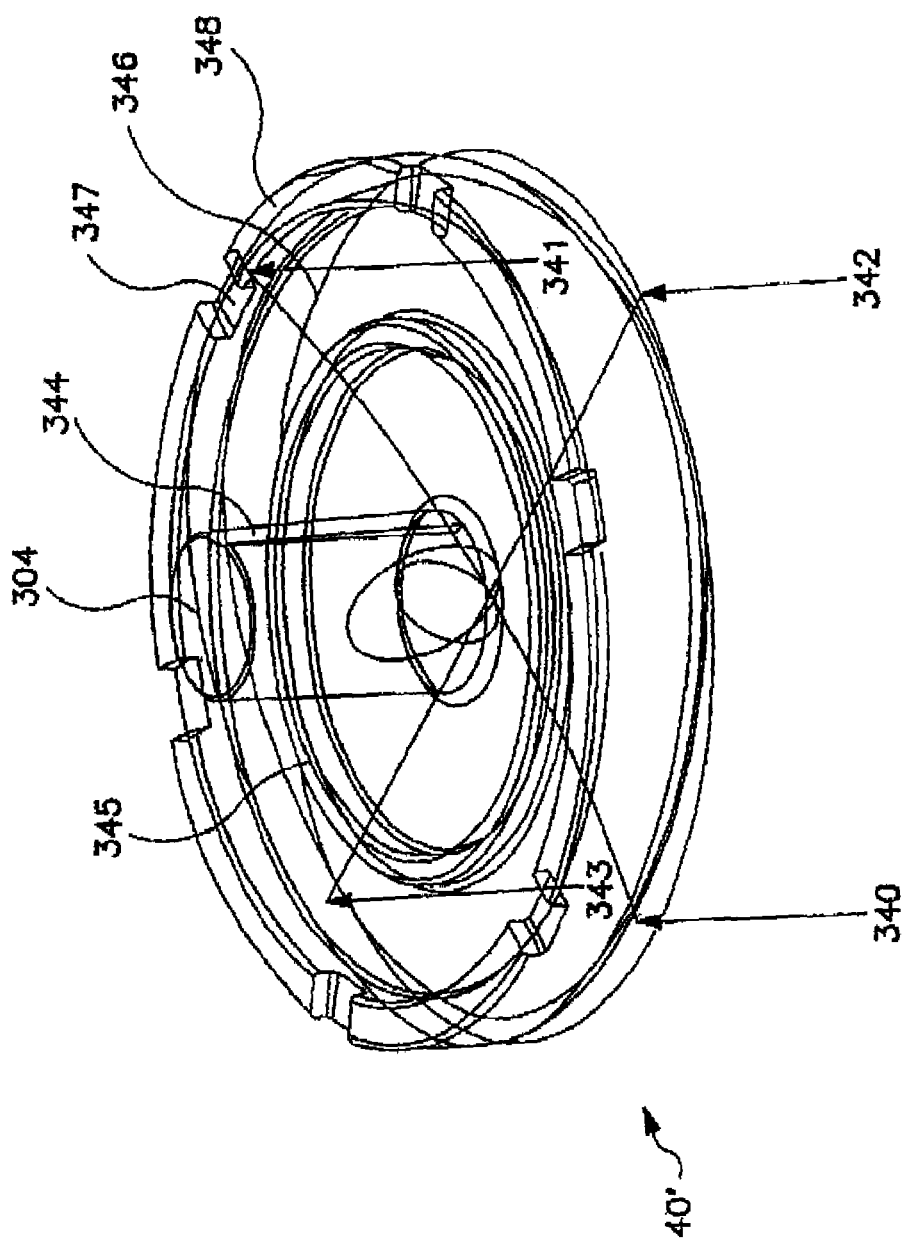
FIG. 5c is a perspective view of the upper surface of an exemplary implant, in one embodiment of the present invention.
Figure 5D:
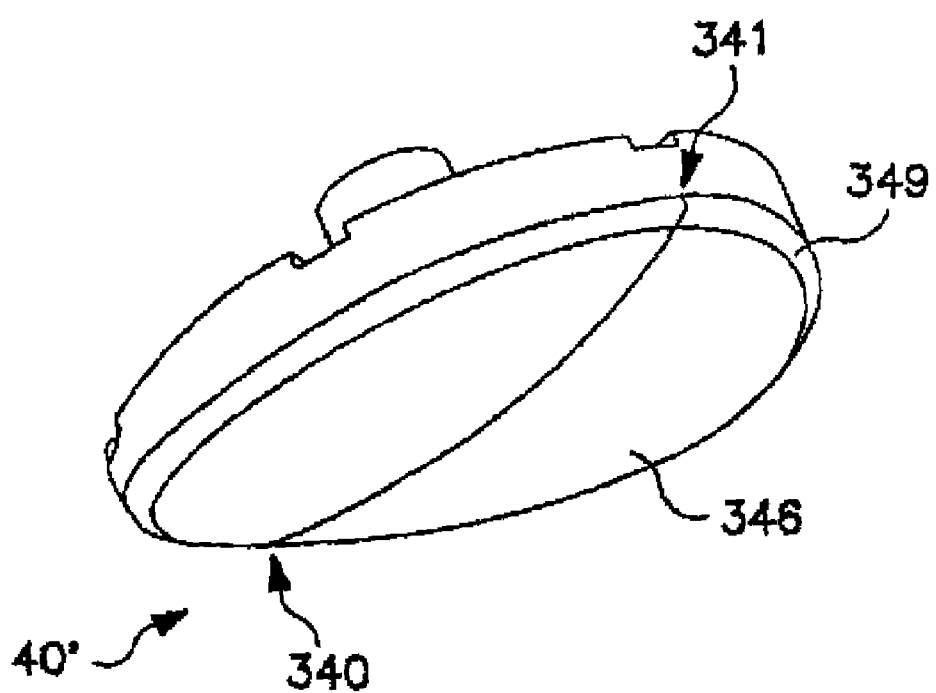
FIG. 5d is a perspective view of the lower surface of an exemplary implant, in one embodiment of the present invention.

FIGS. 5c and 5d illustrate an alternative embodiment of the implant 40', having a ML curve between data points 340 and 341 and an AP curve between data points 342 and 343, with male-shaped mating component 304 and key-shaped portion 344 for engagement with a reciprocal key-shaped surface in the proximal extension of a fixation screw, protrusions 345 (creating contact surfaces on the top 346 of the implant 40'), radial cuts 347 located at the outer diameter 348 of the implant 40', and radius 349 (which may be formed, e.g. using an abrasive wheel) around the intersection of the outer diameter at point 341 and the surface comprising the patient geometry.

Referring to FIGS. 18a and 18b, bone cutting or scoring instrument 250 includes a handle (not shown), a cannulated shaft 111 that extends through the handle, and offset arm 140 housing adjustable blades 141. In the embodiment shown, individual cutting blades 141 are attached to offset arm 140 either fixedly or removably, e.g. via threaded portions 142, into threaded recesses 342 of the offset arm 140, although other attachment means may be used. With guide pin 20 advanced through shaft 113 positioned on the reference axis 20A, a fixed distance from the rotational or references axis 20A to each of the cutting or scoring blades 141 is established. These lengths define the radii that are to be effected in the articular surface, as the scoring instrument 250 is rotated around the guide pin 20, corresponding to the protrusions 195 on the bone contacting surface 42 of the implant 40 creating a matching fit between the bone surfaces of the prepared target site and the bone contacting surfaces of the implant.

In an alternative embodiment, as shown in FIG. 18c, cutting blades are arranged on carrier 145, configured so that it can be mounted within the slotted surface 114 of offset arm 112, depicted in FIG. 17a. In another embodiment, as shown in FIG. 18d, cutting blades 141 can be fixedly positioned on offset arm 140. Using the same dimensions obtained during articular surface mapping procedure, the cutting and scoring device 250 can be fabricated to prepare the articular surface to correspond to the implant geometry to optimize fit. In another alternative embodiment, as shown in FIG. 18e, a bone cutting instrument 352 corresponds to the alternative embodiment of the implant 40' illustrated in FIGS. 5c and 5d. Instrument 352 has a handle (not shown), a cannulated shaft 353 that extends through the handle and through the cannulation 355, offset arm 354 with blades 350 and 351 corresponding to the protrusions 345 on the bone contacting surface 42 of the implant 40 creating a matching fit between the bone surfaces of the prepared target site and the bone contacting surfaces 346 of the implant 40'.

As shown in FIG. 14b, an angular dimension 95, relating some locating surface or feature on the hex-shaped cover 30 or on the fixation screw 10, to the four points 81a, 81b, 82a and 82b, may also be captured at the time of the initial procedure to assist in orientation of the implant 40 to the fixation screw 10. Guide aperture 46 in implant 40 is located off the reference axis 20A and may serve as the locating feature and/or as a suture passage way in the implantation procedure. Alternatively, a surface or feature created on the implant 40, may serve to reference or align to such locating surface on the hex-shaped cover 30 or the fixation screw 10.

Additional data can be taken at the time of the initial procedure, e.g., for fabricating a non-circular implant. Additional data curves can also be defined by measuring the offsets from the reference axis 20A and determining diameters at these offsets. The final implant geometry, although measured using circular techniques, need not be circular.

Referring to FIGS. 10a and 10b, following fabrication of the implant 40, a second procedure is performed. If a cover 30 (or plug) is in place, it is removed, exposing proximal extension 14 (or recess) or some other precision taper or engagement surface located at the proximal end 17 of the fixation screw 10 to which the implant 40 is to be affixed. A pin having a distally mounted element or barb 5 is placed through hole 16 running through the central lumen of the fixation screw 10 so that the distally mounted element 5 is secured into the screw. The distally mounted element 5 carries one or more suture strands 85 that now trail from the fixation screw 10. Alternatively, a pin, braided cable, or flexible wire may also be used. However, sutures may make passing the implant 40 through the incision 200 and subsequent handling easier.

Turning to FIGS. 11a and 11b, the sutures 85 are then threaded through guide aperture 46 of the implant 40 and a knot or bead 49 may be created proximal to the implant, so that tensing one of the free running sutures 85 helps to advance the implant 40 toward the proximal extension 14 (or recess) of the fixation screw 10. Alternatively, the suture strands 85 can be passed through the central lumen or shaft of a driving rod or other instrument to aid in seating the implant 40, and positioned in the fixation screw 10 thereafter.

If necessary, the arthroscopic wound 200 is expanded slightly in either a vertical or horizontal direction, so that the implant 40 may be passed through. A polymeric sleeve (not shown) positioned over the implant may prove helpful in passing the implant through the incision. As shown in FIG. 11b, based on the size of the implant 40, anatomy of the knee 50, and retraction of the knee, it may be necessary to position the implant in the interchondular notch 77 as a staging area prior to final placement. By continuing to manipulate and tension the suture strands 85, the implant 40 can be brought coaxial to the proximal extension 14 of the fixation screw 10.

As shown in FIGS. 15c and 15d, alternatively, driver 130 includes handle 110, a cannulated shaft 111 that extends through the handle and a cannulated seat portion 131 attached to the end of the shaft. Tether element 135, which may comprise sutures or wire, is passed through driver 130 and is threaded through implant 40 through guide aperture 46, connecting the implant to the driver toward seat portion 131. The implant 40 and the driver 130 are then inserted arthroscopically through incision 200 to the target site. By tensioning tether element 135 at the end 136 of handle 110, the implant 40 is drawn back into seat portion 131 of driver 130. By maintaining tension on tether element 135, the implant 40 can then be controllably delivered to the prepared target site. At least the inner surface of seat portion 131 comprises a material that can be impacted to seat the implant 40 without damaging the implant surface.

Referring to FIG. 12, once coaxial, the implant 40 can be aligned via engagement of the proximal extension 14 on fixation screw 10 and precisions taper 44 on the bottom surface 42 of the implant and any locating feature, and driven into place with a plastic driving rod 91 and mallet 95. A protrusion 92 of high strength material mounted at the distal tip 93 of the driving rod 91 may be necessary to ensure that the rod stays centered on the implant 40 during driving.

Finally, as shown in FIG. 13, through guide aperture 46 on the upper surface 41 of the implant 40, bone cement 300 may be injected to enhance the contact surface between the implant 40 and the subchondral bone 100. Vents, such as milled slots 13 in the fixation screw 10, and in the walls of the implant central protrusion may be desirable to facilitate the flow of such materials.

Figure 19E:
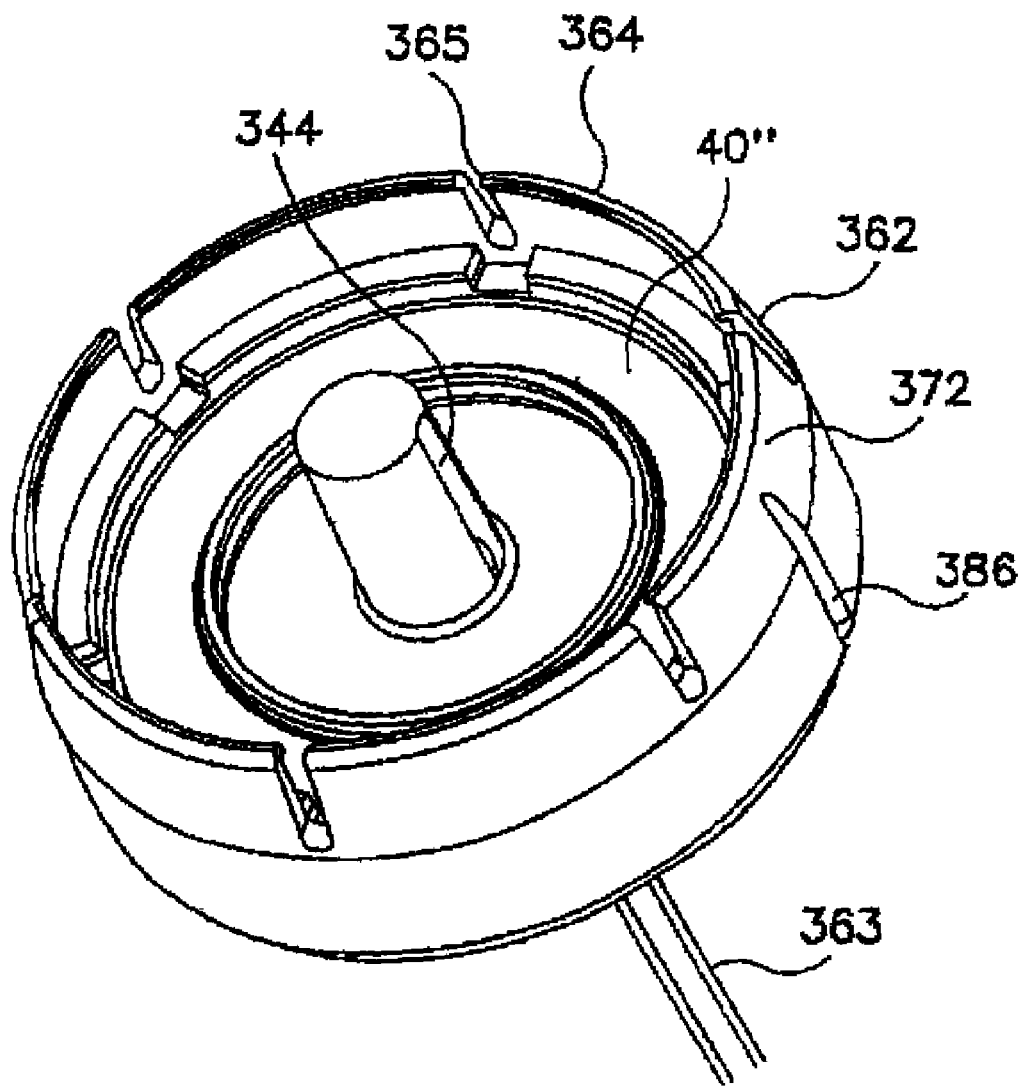
FIG. 19e is a top perspective view of the exemplary implant of FIG. 19d seated in the taper lock ring, in one embodiment of the present invention.

Alternatively, guide aperture 46 in the implant 40 may be altogether eliminated by using an alternative implant delivery system, as shown in FIGS. 19d through 19i, corresponding to an implant similar to that shown in FIGS. 5c and 5d. The alternative system comprises the implant 40" and a washer 361 for holding a suture 363, the washer 361 being adapted to fit into a taper lock ring 360. The ring 360 has a taper lock portion 362 having a series of notches 365 along its perimeter, creating flaps 372 that permit the taper lock portion 362 to flex somewhat. The taper lock portion 362 has a diameter gradually tapering from the middle to the proximal end 364 of the ring. The taper lock ring 360 may also have an alignment notch 386 or similar feature for properly aligning the taper lock ring 360 with respect to key-shaped portion 344 of the implant 40", which is to engage with a reciprocal key-shaped surface in the proximal extension of a fixation screw, so as to seat properly the implant rotationally with respect to the defect site when it is later seated thereon. A washer 361 is disposed between the ring 360 and the implant 40" and has two apertures 366 disposed in a recessed area 367 in the center of the washer. The suture 363 is threaded through the two apertures 366 to form a suture loop 368, which remains in the recessed area when the ends of the suture 363 are pulled, so as to keep the suture loop 368 below the top surface 369 of the washer 361. The implant 40" has a diameter at its center portion 370 that is approximately equal to the inner diameter of the ring 360 at its taper lock portion 362. Thus, when tension is applied to the ends of the suture 363, the taper lock portion 362 of the ring 360 may flex outward to receive slidably therein the implant 40" and washer 361, which subsequently lock into the taper lock portion 362 of the ring, once the center portion 370 of the sides of the implant 40" is seated within the proximal end 364 of the ring by friction fit, as shown in FIG. 19e. It is noted that the center portion 370 of the sides of the implant 40" to be of a width permitting the implant and washer to travel slidably within the ring 360 to some degree.

Figure 19H:
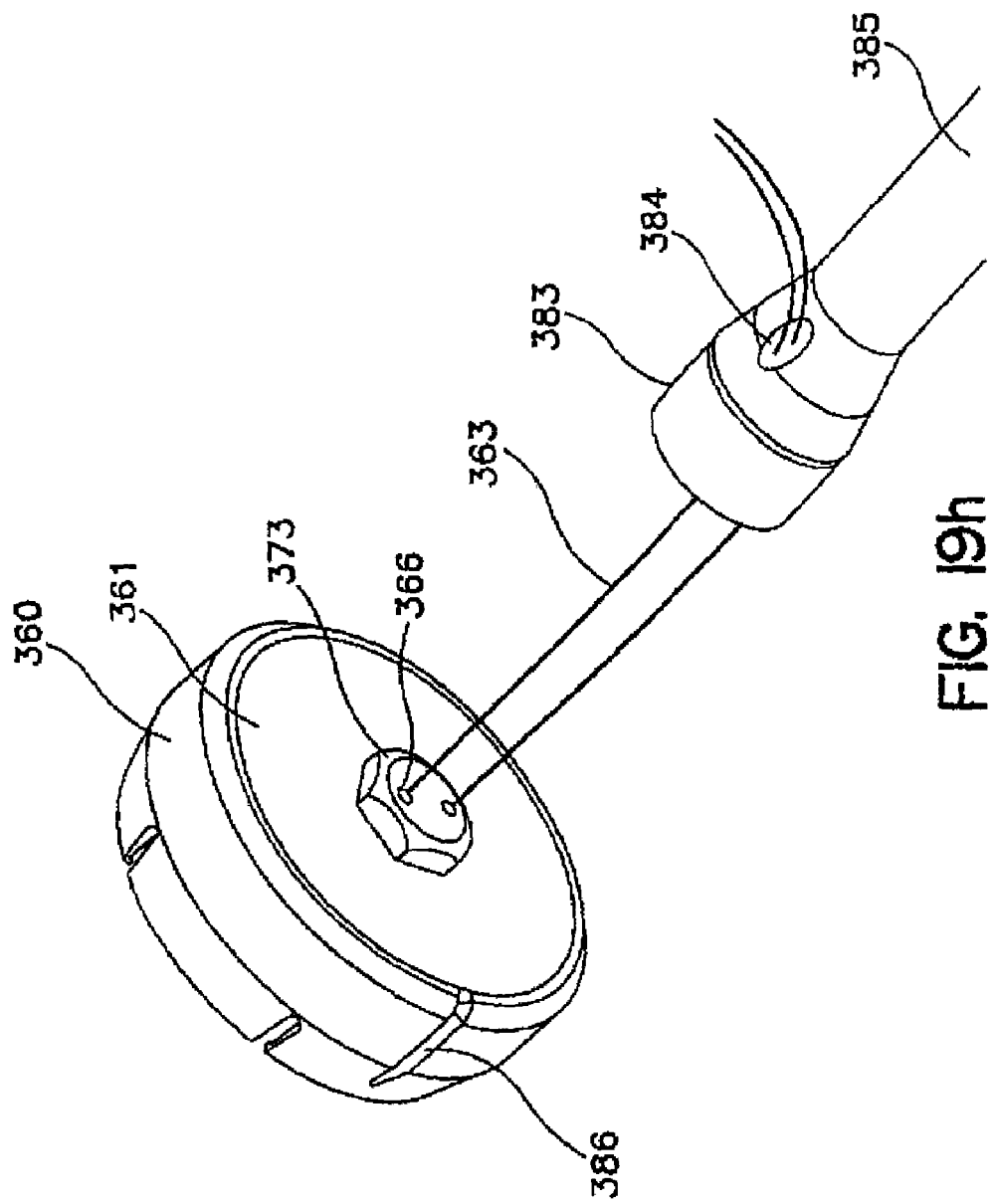
FIG. 19h is another perspective view of the exemplary implant of FIG. 19d seated in the taper lock ring, with washer and suture, wherein the suture is threaded through an aperture at the distal end of a seating tool, at a second point in time during the process of seating the implant into the defect site, in one embodiment of the present invention.
Figure 19I:
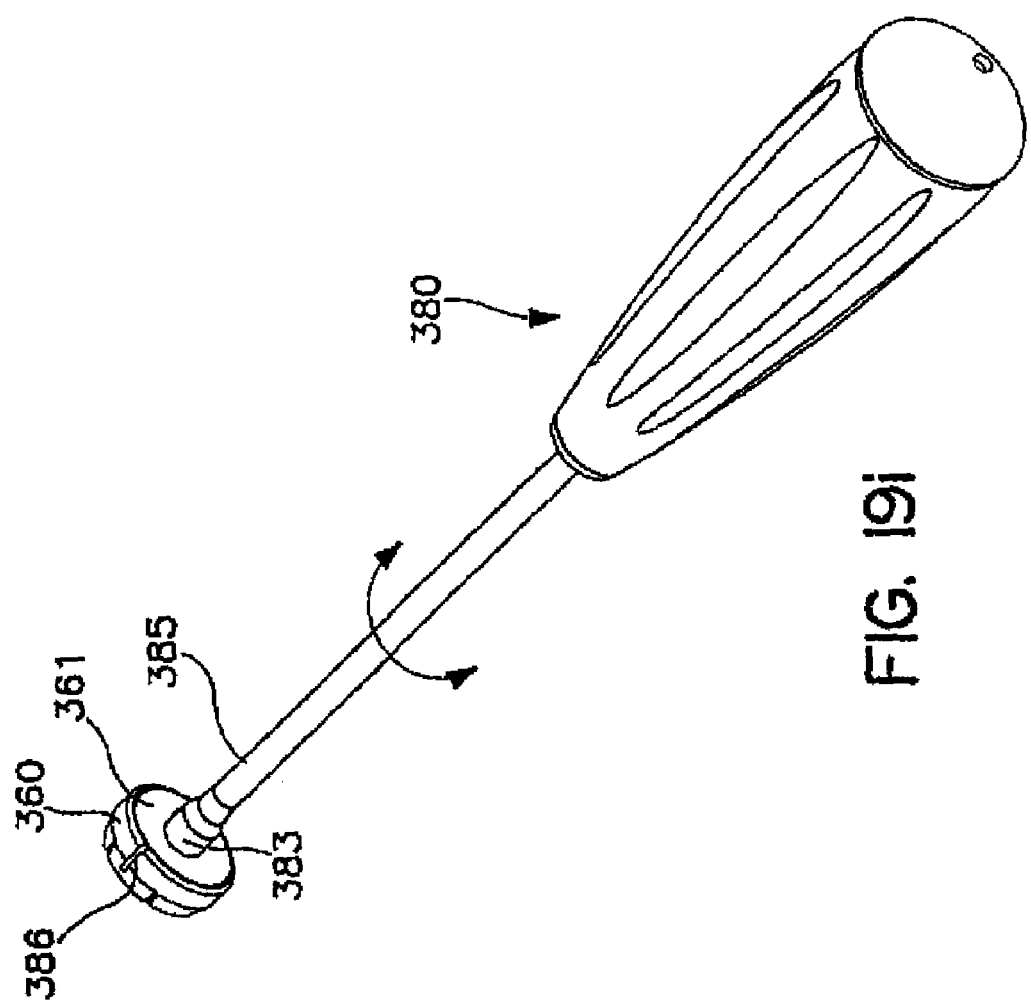
FIG. 19*i* is another perspective view of the exemplary implant of FIG. 19*d* seated in the taper lock ring, wherein the distal end of a seating tool is disposed onto the implant, at a third point in time during the process of seating the implant into the defect site, in one embodiment of the present invention.

As shown in FIG. 19f, a hex nut 373 may be integrally formed in the center of the washer 361 on its bottom side 374, for mating with an appropriately configured tool for seating the implant 40". As FIG. 19f illustrates, the implant 40", along with washer 361, ring 360, and sutures 363, is pushed through the incision 200 at the defect site. Next, as shown in FIGS. 19g-19i, illustrative of successive steps in the process of seating the implant, a seating tool 380 may be used to seat the implant. Seating tool 380 comprises a shaft 385, a handle 381 (which may have a through hole 382, if the same handle and/or shaft is used with interchangeable tips for performing various functions, although a through hole 382 is not integral to seating the implant), and tip 383 suitably configured to drive hex nut 373 (or other mating feature) and having an aperture 384 through which the ends of the suture 363 may be threaded. Once the tip 383 of the tool 380 is introduced into the incision 200, the sutures 363 may be used as a guide for seating the tip 383 of the tool 380 onto the hex nut 373, which may be accomplished by alternately pulling on each end of the suture 363 to toggle the tip 383 of the tool 380 back and forth. Once the tip 383 of the tool 380 is seated onto the hex nut 373, the tool 380 may be rotated in either direction to seat the implant assembly properly (comprising implant 40", taper lock ring 360, and washer 361) at the defect site. This may be effected by rotating tool 380 until alignment notch 386 and corresponding key-shaped portion 344 of the implant 40" are aligned with the corresponding reciprocal key-shaped surface in the proximal extension of the fixation screw, whereby the implant should slide into place, thereby properly seating the implant rotationally with respect to the defect site. As shown in FIG. 12 with respect to the prior described embodiment, once properly seated, the implant 40" can be driven into place with a plastic driving rod 91 and mallet 95, and as shown in FIG. 13 with respect to the prior described embodiment, bone cement 300 may also be placed prior to the final seating of the implant 40" to enhance the contact surface between the implant 40" and the subchondral bone 100. It should be understood that the taper lock ring 360, washer 361, and sutures 363 described with respect to this embodiment allow the implant to be noncannulated but still easily handled. These elements are not required to be constructed as illustrated herein, and may be replaced by adhesive components, suction components, or other components serving the same function.

Figure 21:
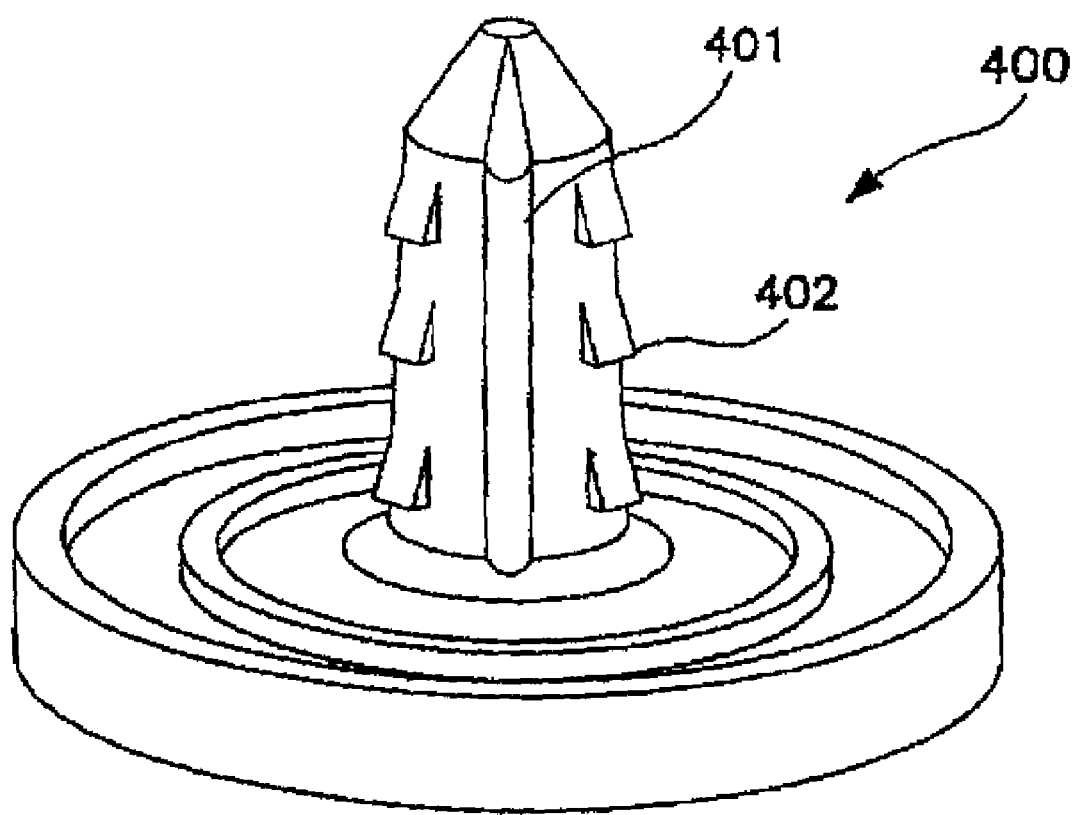
FIG. 21 is a perspective view of an exemplary unitary implant, in one embodiment of the present invention.
Figure 22:
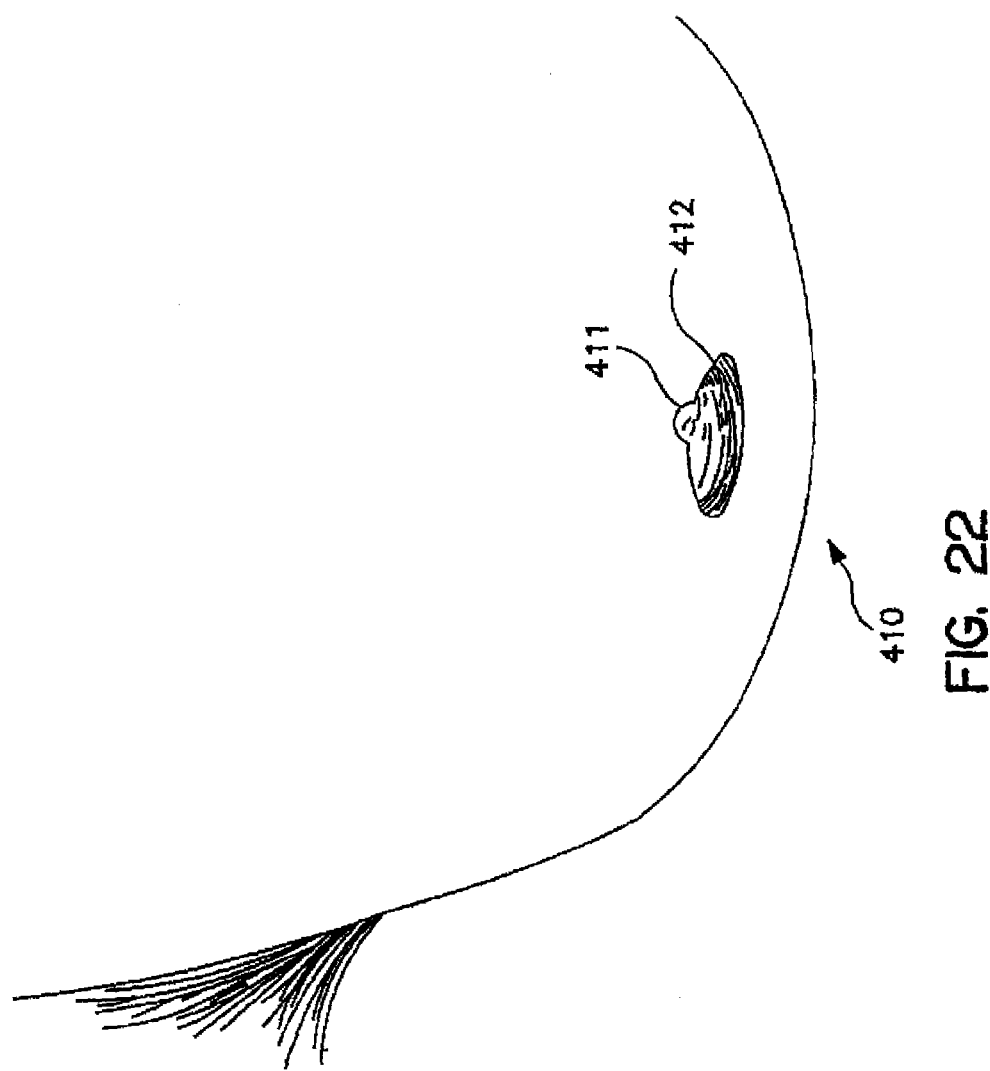
FIG. 22 is a perspective view of a defect site with a keyed aperture for receiving the exemplary unitary implant of FIG. 21, in one embodiment of the present invention.

As FIGS. 21 and 22 illustrate, a unitary (one-piece) implant 400 may also be constructed, thereby obviating the need for a fixation screw, taper lock ring, washer, and suture. In this embodiment, implant 400 has key-shaped portion 401 for engagement with a reciprocal key-shaped surface 411 in an aperture 412 at the defect site 410, a plurality of barbs 402 for producing outward tension within the aperture 412 at the defect site 410 and for increasing the contact surface area of the implant 400 with respect to the aperture 412 at the defect site 410. In this embodiment, an aperture 412 having a key-shaped surface 411 or other feature for mating with the implant is created directly in the defect site 410, by boring, abrasion, or other techniques for forming an appropriately shaped aperture in the chondral bone 410 for receiving an implant 400 having a corresponding key-shaped or other mating feature 401. It should also be recognized that, in this or other embodiments, the fixation screw could be replaced with a tensioned member attachment, e.g., anchored to the distal femoral cortex. Alternatively, the fixation screw could be configured as a guide wire, only to define the axis AA corresponding to an axis about the point of origin in the implant to be used (as shown in FIGS. 14c and 19c), but not to provide mechanical anchoring to or for the implant.

Figure 23:
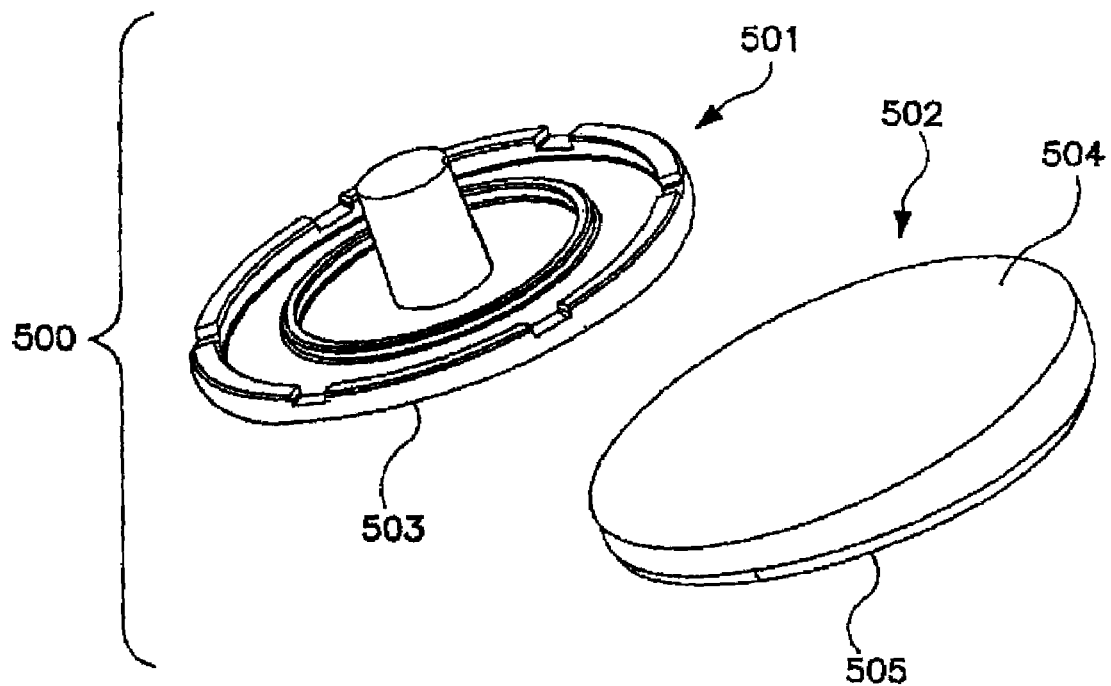
FIG. 23 is a perspective view of an exemplary composite implant, in one embodiment of the present invention.

FIG. 23 illustrates other alternative embodiments for an implant consistent with the invention, showing a perspective view of the components of an exemplary composite implant, in one embodiment of the present invention. As shown, implant 500 comprises top 501 and bottom 502 portions. Top portion 501 has a bottom surface 503 which may be glued, welded, bonded, or otherwise attached to top surface 504 of bottom portion 502, while bottom surface 505 of bottom portion 502 comprises the patient geometry and is the load-bearing surface of the implant, as set forth hereinabove. Top 504 and bottom 505 surfaces of the bottom portion 502 may comprise, in whole or in part, bioengineered material, while top portion 501 may comprise a material such as titanium. In such a configuration, top portion 501 may be fabricated and/or manufactured (e.g. in large quantities) as a universal, generic, standard supply item for medical practitioners, which merely needs to be attached to a custom-machined bottom portion 502 comprising the patient-specific geometry. Surfaces 503 and 504 may be flat or may comprise other mating features, shapes or configurations.

Figure 24:
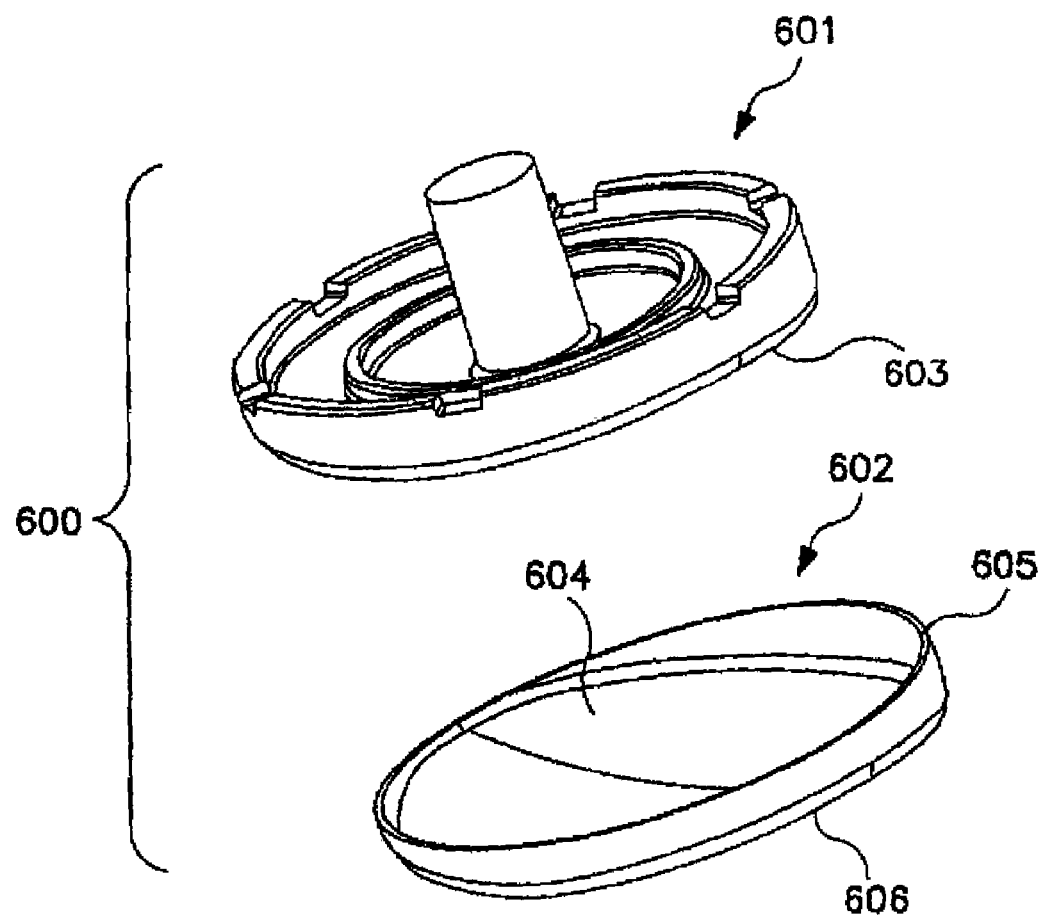
FIG. 24 is a perspective view of another exemplary composite implant, in one embodiment of the present invention.

Further composite implant embodiments are illustrated in FIG. 24, wherein implant 600 comprises the patient-specific geometry 606 and a uniform thickness material bottom portion 602 comprising the bottom or bearing surface 606. The bottom surface 603 of top portion 601 mates with the top surface 604 of bottom portion 602, and surfaces 603 and 604 may be flat or may comprise other mating features, shapes or configurations. Lip 605 of bottom portion 602 has an inside diameter substantially the same as the outside diameter of top portion 601, so that top portion 601 fits slidably into bottom portion 602, whereby the two portions 601 and 602 may be glued, welded, bonded, or otherwise attached to one another. Bottom surface 606, being of uniform thickness, reflects the patient-specific geometry which surface 603 comprises and is the load-bearing surface of the implant.

Other materials from which an implant consistent with the invention may be constructed, in whole or in part, include ceramic, e.g. aluminum oxide or zirconium oxide; metal and metal alloys, e.g. Co—Cr—W—Ni, Co—Cr—M, CoCr alloys, CoCr Molybdenum alloys, Cr—Ni—Mn alloys, powder metal alloys, 316L stainless steel, Ti 6Δ1-4V ELI; polymers, e.g., polyurethane, polyethylene (wear resistant and cross-linked), thermoplastic elastomers; biomaterials, e.g. polycaprolactone; and diffusion hardened materials, e.g. Ti-13-13, Zirconium and Niobium. Coatings used may include, e.g., porous coating systems on bone-contacting surfaces, hydrophilic coatings on load-bearing surfaces, hydroxyapatite coatings on bone-contacting surfaces, and tricalcium phosphate on bone-contacting surfaces. Additionally, components of the invention may be molded or cast, hand-fabricated, or machined.

Alternatively, measurement methods may be utilized whereby radius measurements are taken with respect to an axis AA corresponding to an axis about the point of origin in the implant to be used (as shown in FIGS. 14c and 19c). The technique is used in reverse, whereby aiming devices are used to place axis AA with respect to prefabricated generic-geometry implants.

It is noted that, although the invention is herein described as utilizing a single reference axis, multiple reference axes may be used for measuring, mapping, or cutting a single defect or an articular surface having multiple defects, as well as for fabricating a single implant, or multiple implants for a single articular surface, consistent with the invention. In other embodiments, methods for mapping the defect and/or articular surface other than those described hereinabove are possible, e.g., MRI or CT scanning.

It is further noted that, although the invention is described herein as utilizing the specific geometry of a patient's articular surface to fabricate an implant for that patient, it is contemplated that data from a plurality of patients may be analyzed statistically and utilized in fabricating and/or manufacturing (e.g. in large quantities) one or more universal, generic, or standard supply item type implants for medical practitioners to use in a procedure consistent with the invention. For such implants, as well as for patient-specific implants as described herein, pre- or post-implantation trimming may be required to correct for minor variations that may occur as between the implant and the subchondral bone (or other articular surface).

It should be understood that, although the various tools described hereinabove, e.g., for measuring, cutting, and seating, are described as separate devices, a single handle, shaft and/or instrument may be configured to serve as a universal mounting tool for a series of devices for performing various functions consistent with the invention.

Those skilled in the art will recognize that the present invention is subject to other modifications and/or alterations, all of which are deemed within the scope of the present invention, as defined in the hereinafter appended claims.

What is claimed is:

1. An implant system, comprising:
   a cannulated post comprising a threaded portion configured to engage bone beneath a patient's articular surface;
   an implant having a perimeter defining an outer bound of a continuous load bearing surface that substantially matches at least one curvature of said patient's articular surface;
   a fixation element configured to couple said post to said implant, wherein said fixation element is further configured to permit said implant to rotate with respect to said post; and
   a guide pin configured to engage said bone and provide an axis in said bone, wherein at least a portion of said guide pin is configured to be received only in said cannulated post of said implant.

2. The implant system according to claim 1, wherein said fixation element is further configured to secure said implant to said post.

3. The implant system according to claim 2, wherein implant is configured to be rotated to a predetermined alignment with respect to said articular surface before said implant is secured to said post.

4. The implant system according to claim 1, wherein said fixation element comprises a first fixation element coupled to said post and a second fixation element coupled to said implant.

5. The implant system according to claim 4, wherein at least one of said first or said second fixation elements includes a tapered surface.

6. The implant system according to claim 4, wherein said first fixation element comprises a male member and said second fixation element comprises a female member.

7. The implant system according to claim 6, wherein said male member comprises a generally cylindrical extension having a taper.

8. The implant system according to claim 7, wherein said female member comprises a protrusion extending generally outwardly from a bone-facing distal surface, said protrusion including a tapered recess.

9. The implant system according to claim 4, wherein said first fixation element comprises a female member and said second fixation element comprises a male member.

10. The implant system according to claim 9, wherein said female member comprises a tapered recess disposed proximate a proximal-most end of said post.

11. The implant system according to claim 10, wherein said male member comprises a protrusion extending generally outwardly from a bone-facing distal surface, at least a portion of an outer surface of said protrusion having a taper.

12. The implant system according to claim 4, wherein said first and said second fixation elements each include a tapered surface configured to engage each other in a snap-fit arrangement.

13. The implant system according to claim 4, wherein said first and said second fixation elements each include a tapered surface configured to engage each other in a press-fit arrangement.

14. The implant system according to claim 4, wherein said first and said second fixation elements each include a tapered surface configured to engage each other in a threaded arrangement.

15. The implant system according to claim 1, wherein said post comprises a tapered distal end and aggressive distal threads configured to dilate open and radially compress said bone.

16. The implant system according to claim 15, wherein a diameter of a center region of said post is substantially uniform along a longitudinal axis of said post.

17. The implant system of claim 1, wherein said implant defines a central passageway configured to be axially aligned with said cannulated post.

18. The implant system of claim 1, wherein said guide pin is configured to provide a working axis substantially normal to said patient's articular surface proximate a defect in said patient's articular surface.

19. The implant system of claim 18, wherein said guide pin comprises a shaft and a threaded region dispose about an end region of said shaft, said threaded region configured to engage with said bone beneath said patient's articular surface.

20. The implant system of claim 19, further comprising a driver configured to be coupled to a second end region of said shaft of said guide pin, said driver further configured to rotate said guide pin about a longitudinal axis of said guide pin to advance said guide pin into said bone.

21. The implant system of claim 18, wherein said guide pin is configured to be removed from said bone after said cannulated post engages said bone.

22. An implant system, comprising:
   an implant having a perimeter defining an outer bound of a continuous load bearing surface that substantially matches at least one curvature of a patient's articular surface, said implant further comprising a first fixation element disposed about a bottom surface;
   a cannulated post configured to engage bone beneath said patient's articular surface, said post further comprising a second a fixation element configured to rotatably couple said post to said first fixation element of said implant; and
   a guide pin configured to engage said bone and to provide an axis in said bone, wherein at least a portion of said guide pin is configured to be received only in said cannulated post of said implant.

23. The implant system of claim 22, wherein said post further comprises aggressive distal threads.

24. The implant system according to claim 22, wherein said post comprises a tapered distal end having aggressive distal threads configured to dilate open and radially compress said bone.

25. The implant system of claim 22, wherein said implant system comprises a CoCr molybdenum alloy.

26. The implant system of claim 22, wherein said implant system comprises Ti 6Al-4V ELI.

27. The implant system according to claim 22, wherein implant is configured to be rotated to a predetermined alignment with respect to said articular surface before said implant is secured to said post.

28. The implant system of claim 22, wherein said guide pin is configured to provide a working axis substantially normal to said patient's articular surface proximate a defect in said patient's articular surface.

29. The implant system of claim 28, wherein said guide pin comprises a shaft and a threaded region dispose about a first end region of said shaft, said threaded region configured to engage with said bone beneath said patient's articular surface.

30. The implant system of claim 29, further comprising a driver configured to be coupled to a second end region of said shaft of said guide pin, said driver further configured to rotate said guide pin about a longitudinal axis of said guide pin to advance said guide pin into said bone.

31. The implant system of claim 28, wherein said guide pin is configured to be removed from said bone after said cannulated post engages said bone.

* * * * *

UNITED STATES PATENT AND TRADEMARK OFFICE
CERTIFICATE OF CORRECTION

| | | |
|---|---|---|
| PATENT NO. | : 7,604,641 B2 | Page 1 of 1 |
| APPLICATION NO. | : 11/379151 | |
| DATED | : October 20, 2009 | |
| INVENTOR(S) | : Steven J. Tallarida et al. | |

It is certified that error appears in the above-identified patent and that said Letters Patent is hereby corrected as shown below:

In column 24, line 47, in Claim 22, delete "second a" and insert -- second --, therefor.

Signed and Sealed this

Twelfth Day of January, 2010

David J. Kappos
*Director of the United States Patent and Trademark Office*